United States Patent
Hafner et al.

(10) Patent No.: US 9,187,583 B2
(45) Date of Patent: Nov. 17, 2015

(54) CATALYSTS

(75) Inventors: Norbert Hafner, Linz (AT); Pascal Castro, Helsinki (FI); Pavel Sergeevich Kulyabin, Moscow (RU); Vyatcheslav Izmer, Moscow (RU); Alexander Voskoboynikov, Moscow (RU); Luigi Resconi, Ferrara (IT); Dmitry Kononovich, Moscow (RU); Ville Virkkunen, Helsinki (FI); Dmitry Uborsky, Moscow (RU)

(73) Assignee: BOREALIS AG, Vienna (AT)

( * ) Notice: Subject to any disclaimer, the term of this patent is extended or adjusted under 35 U.S.C. 154(b) by 9 days.

(21) Appl. No.: 14/131,588

(22) PCT Filed: Jul. 6, 2012

(86) PCT No.: PCT/EP2012/063288
§ 371 (c)(1),
(2), (4) Date: Apr. 14, 2014

(87) PCT Pub. No.: WO2013/007650
PCT Pub. Date: Jan. 17, 2013

(65) Prior Publication Data
US 2014/0221584 A1    Aug. 7, 2014

(30) Foreign Application Priority Data

Jul. 8, 2011    (EP) .................................... 11173344

(51) Int. Cl.
| | | |
|---|---|---|
| C07F 17/00 | (2006.01) | |
| C07F 7/08 | (2006.01) | |
| C08F 4/6592 | (2006.01) | |
| C08F 10/06 | (2006.01) | |
| C07C 13/465 | (2006.01) | |
| C08L 23/12 | (2006.01) | |
| C08F 110/06 | (2006.01) | |
| C08F 210/06 | (2006.01) | |
| C08F 4/659 | (2006.01) | |

(52) U.S. Cl.
CPC ........... *C08F 4/65927* (2013.01); *C07C 13/465* (2013.01); *C07F 7/0818* (2013.01); *C07F 17/00* (2013.01); *C08L 23/12* (2013.01); *C08F 4/65912* (2013.01); *C08F 4/65916* (2013.01); *C08F 110/06* (2013.01); *C08F 210/06* (2013.01); *C08L 2207/02* (2013.01); *C08L 2314/06* (2013.01)

(58) Field of Classification Search
CPC .. C07F 17/00; C08F 4/65927; C08F 4/65908; C08F 4/65912; C08F 10/00; C08F 10/06
See application file for complete search history.

(56) References Cited

U.S. PATENT DOCUMENTS 6,627,764 B1 * 9/2003 Schottek et al. ................ 556/11
7,834,205 B2 * 11/2010 Resconi et al. ................ 556/53
2003/0149199 A1 8/2003 Schottek et al.
2006/0020096 A1 1/2006 Schottek et al.

FOREIGN PATENT DOCUMENTS

| | | |
|---|---|---|
| CA | 2628442 A1 | 5/2007 |
| EP | 0834519 A1 | 4/1998 |
| EP | 1074577 A1 | 2/2001 |
| EP | 1640377 A1 | 3/2006 |
| WO | 9840331 A1 | 9/1998 |
| WO | 0148034 A2 | 7/2001 |
| WO | 03050131 A1 | 6/2003 |
| WO | 03051934 A2 | 6/2003 |
| WO | 2003045551 A1 | 6/2003 |
| WO | 2004106351 A1 | 12/2004 |
| WO | 2006069733 A1 | 7/2006 |
| WO | 2006134046 A1 | 12/2006 |
| WO | 2007051612 A1 | 5/2007 |
| WO | 2007107448 A1 | 9/2007 |
| WO | 2007116034 A1 | 10/2007 |
| WO | 2009054833 A2 | 4/2009 |
| WO | 2011135004 A2 | 11/2011 |

OTHER PUBLICATIONS

International Search Report and Written Opinion mailed Oct. 18, 2012 (PCT/EP2012/063288); ISA/EP.
Spaleck et al., Journal of Molecular catalysis A, 1998, vol. 128, p. 279.
Miyake et al, Macromolecules 1995, vol. 28, p. 3074.
Elder et al., Kin. Cat. 2006, vol. 47(2), p. 192.

* cited by examiner

*Primary Examiner* — Caixia Lu
(74) *Attorney, Agent, or Firm* — Banner & Witcoff, Ltd.

(57) ABSTRACT

A racemic complex of formula (I), wherein M is zirconium or hafnium; each X is a sigma ligand; L is a divalent bridge selected from —R'$_2$C—, —R'$_2$C—CR'$_2$, —R'$_2$Si—, —R'$_2$Si—SiR'$_2$—, —R'$_2$Ge—, wherein each R' is independently a hydrogen atom, C$_{1-20}$-hydrocarbyl, tri(C$_{1-20}$-alkyl)silyl, C$_{6-20}$-aryl, C$_{7-20}$-arylalkyl or C$_{7-20}$-alkylaryl; R$^2$ and R$^{2'}$ are each independently a C$_{1-20}$ hydrocarbyl radical optionally containing one or more heteroatoms from groups 14-16; R$^{5'}$ is a C$_{1-20}$ hydrocarbyl group optionally containing one or more heteroatoms from groups 14-16 and optionally substituted by one or more halo atoms.

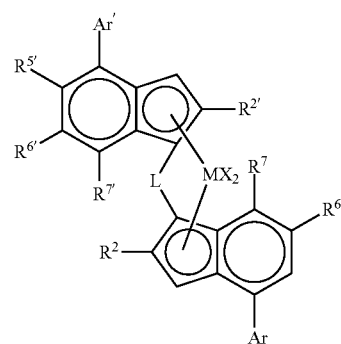

18 Claims, No Drawings

CATALYSTS

The present application is a U.S. National Phase filing of International Application No. PCT/EP2012/063288, filed on Jul. 6, 2012, designating the United States of America and claiming priority to European patent application No. 11173344.0, filed Jul. 8, 2011, and this application claims priority to and the benefit of the above-identified applications, which are both incorporated by reference herein in their entireties.

This invention relates to new asymmetrical bisindenyl ligands, complexes thereof and catalysts comprising those complexes. The invention also relates to the use of the new bisindenyl metallocene catalysts for the production of polypropylene with high molecular weight at good activity levels.

Metallocene catalysts have been used to manufacture polyolefins for many years. Countless academic and patent publications describe the use of these catalysts in olefin polymerisation. Metallocenes are now used industrially and polyethylenes and polypropylenes in particular are often produced using cyclopentadienyl based catalyst systems with different substitution patterns.

The present inventors sought new metallocenes, which provide high molecular weight capability, especially in the case of copolymerization between ethylene and propylene or other alpha olefins. In the case of existing catalysts, the copolymer molecular weight is often strongly reduced by ethylene incorporation or higher molecular weights are obtained at the expense of catalyst activity. In addition, the overall productivity of the existing catalysts still needs to be improved.

The present inventors have found a new class of asymmetric, chiral, racemic, anti, bridged bisindenyl metallocenes which are simple to synthesize despite their asymmetry and which are readily separable from their syn (meso-like) isomers. The two indenyl ligands are different from each other, that is, each indenyl ligand bears a set of substituents that are either chemically different, or located in different positions with respect to the other indenyl ligand. For the purpose of this invention, anti means that the two indenyl ligands are oriented in opposite directions with respect to the cyclopentadienyl-metal-cyclopentadienyl plane, while syn means that the two indenyl ligands are oriented in the same direction with respect to the cyclopentadienyl-metal-cyclopentadienyl plane.

They have high catalyst productivity and improved performance in the production of high molecular weight polypropylene homopolymers, especially those of $MFR_2 < 1$ and in the production of propylene copolymers. During copolymer manufacture, the metallocenes of the invention possess reduced chain transfer to ethylene, enabling the production of high molecular weight random and heterophasic copolymers.

$C_2$-symmetric metallocenes similar to those claimed below are disclosed for example in WO2007/116034. This document reports the synthesis and characterisation of the metallocene rac-Me$_2$Si(2-Me-4-Ph-5-OMe-6-tBuInd)$_2$ZrCl$_2$ and the use of it as a polymerisation catalyst after activation with MAO for the homopolymerisation of propylene and copolymerisation of propylene with ethylene and higher alpha-olefins in solution polymerisation. This metallocene is symmetrical and the synthesis of this metallocene gives a final yield of 35% and requires a tedious purification procedure.

WO2007/107448 describes the synthesis and polymerization performance of MAO-activated metallocene rac-Me$_2$Si(2-Me-4-(p-tBu-Ph)-6-tBuInd)$_2$ZrCl$_2$ in solution. Again, this is a symmetrical metallocene and the synthesis of this metallocene requires a tedious purification procedure and gives a very low final yield (<5%).

WO1998/040331 concerns a process for the preparation of substituted indanones but mentions rac-Me$_2$Si(2-Me-4-(p-tBu-Ph)Ind)$_2$ZrCl$_2$.

These metallocenes are shown below.

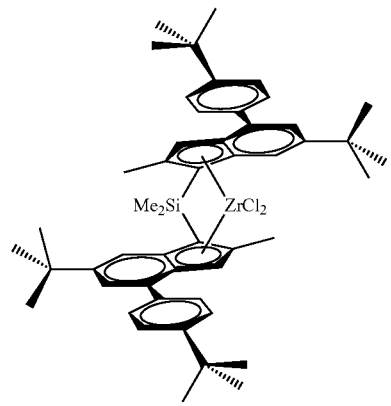

rac-Me$_2$Si(2-Me-4-(p-tBu—Ph)-6-tBuInd)$_2$ZrCl$_2$
WO 2007/107448

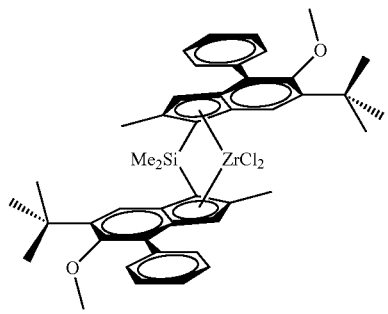

rac-Me$_2$Si(2-Me-4-Ph-5-OMe-6-tBuInd)$_2$ZrCl$_2$
WO 2007/116034

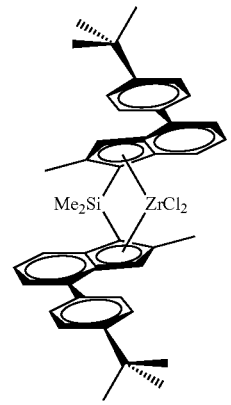

rac-Me$_2$Si(2-Me-4-(p-tBu—Ph)Ind)$_2$ZrCl$_2$
WO 1998/040331

Asymmetrical metallocenes able to produce isotactic polypropylene have been described in the literature, such as for example in Spaleck et al., Journal of Molecular catalysis A, 1998, vol. 128, p. 279, or Miyake et al., Macromolecules 1995, vol. 28, p. 3074. The performance of these metallocenes was, however, far from satisfactory. New, asymmetric metallocenes have been described in the patent and scientific literature, for example EP-A-0834519, WO2001/048034, WO2003/045551, EP-A-1074577, and Elder et al., Kin. Cat. 2006, vol 47(2), p. 192. Here as well, the synthesis of the ligands is highly complicated and the performance of the catalysts not fully satisfactory, especially concerning either molecular weight or catalyst activity.

Our invention concerns the use of asymmetrical metallocenes, especially the anti-isomers thereof, bearing as Π-ligands two indenyls which are different in their substitution pattern while still being relatively simple to synthesize, in particular where the 5 position of one ligand carries a hydrogen atom and the 5-position of the other ring is substituted by a non hydrogen group. These metallocenes have surprisingly been found to possess higher activities than previously reported asymmetric catalysts, as well as higher activities compared to their symmetrical analogues.

SUMMARY

Thus, viewed from one aspect the invention provides a racemic complex of formula (I)

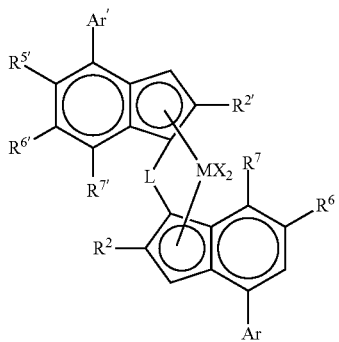

wherein
M is zirconium or hafnium;
each X is a sigma ligand;
L is a divalent bridge selected from —R'$_2$C—, —R'$_2$C—CR'$_2$—, —R'$_2$Si—, —R'$_2$Si—SiR'$_2$—, —R'$_2$Ge—, wherein each R' is independently a hydrogen atom, $C_1$-$C_{20}$-hydrocarbyl, tri($C_1$-$C_{20}$-alkyl)silyl, $C_6$-$C_{20}$-aryl, $C_7$-$C_{20}$-arylalkyl or $C_7$-$C_{20}$-alkylaryl;
$R^2$ and $R^{2'}$ are each independently a $C_1$-$C_{20}$ hydrocarbyl radical optionally containing one or more heteroatoms from groups 14-16;
$R^{5'}$ is a $C_{1-20}$ hydrocarbyl group optionally containing one or more heteroatoms from groups 14-16 and optionally substituted by one or more halo atoms;
$R^6$ and $R^{6'}$ are each independently hydrogen or a $C_{1-20}$ hydrocarbyl group optionally containing one or more heteroatoms from groups 14-16;
$R^7$ and $R^{7'}$ are each independently hydrogen or $C_{1-20}$ hydrocarbyl group optionally containing one or more heteroatoms from groups 14-16;
Ar is independently an aryl or heteroaryl group having up to 20 carbon atoms optionally substituted by one or more groups $R^1$;
Ar' is independently an aryl or heteroaryl group having up to 20 carbon atoms optionally substituted by one or more groups $R^1$;
each $R^1$ is a $C_{1-20}$ hydrocarbyl group or two $R^1$ groups on adjacent carbon atoms taken together can form a fused 5 or 6 membered non aromatic ring with the Ar group, said ring being itself optionally substituted with one or more groups $R^4$; and
each $R^4$ is a $C_{1-20}$ hydrocarbyl group.

Viewed from another aspect the invention provides a catalyst comprising a complex of formula (I)

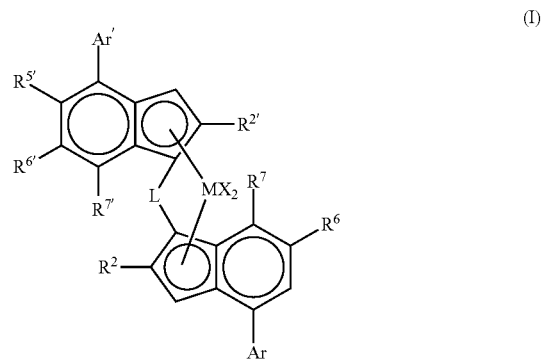

wherein
M is zirconium or hafnium;
each X is a sigma ligand;
L is a divalent bridge selected from —R'$_2$C—, —R'$_2$C—CR'$_2$—, —R'$_2$Si—, —R'$_2$Si—SiR'$_2$—, —R'$_2$Ge—, wherein each R' is independently a hydrogen atom, $C_1$-$C_{20}$-hydrocarbyl, tri($C_1$-$C_{20}$-alkyl)silyl, $C_6$-$C_{20}$-aryl, $C_7$-$C_{20}$-arylalkyl or $C_7$-$C_{20}$-alkylaryl;
$R^2$ and $R^{2'}$ are each independently a $C_1$-$C_{20}$ hydrocarbyl radical optionally containing one or more heteroatoms from groups 14-16;
$R^{5'}$ is a $C_{1-20}$ hydrocarbyl group containing one or more heteroatoms from groups 14-16 optionally substituted by one or more halo atoms;
$R^6$ and $R^{6'}$ are each independently hydrogen or a $C_{1-20}$ hydrocarbyl group optionally containing one or more heteroatoms from groups 14-16;
$R^7$ and $R^{7'}$ are each independently hydrogen or $C_{1-20}$ hydrocarbyl group optionally containing one or more heteroatoms from groups 14-16;
Ar is independently an aryl or heteroaryl group having up to 20 carbon atoms optionally substituted by one or more groups $R^1$;
Ar' is independently an aryl or heteroaryl group having up to 20 carbon atoms optionally substituted by one or more groups $R^1$;
each $R^1$ is a $C_{1-20}$ hydrocarbyl group or two $R^1$ groups on adjacent carbon atoms taken together can form a fused 5 or 6 membered non aromatic ring with the Ar group, said ring being itself optionally substituted with one or more groups $R^4$;
each $R^4$ is a $C_{1-20}$ hydrocarbyl group;
and (ii) a cocatalyst comprising a compound of a group 13 metal, e.g. Al or boron.

The catalyst may be used in non-supported form or in solid form. The catalyst may be used as a homogeneous catalyst or heterogeneous catalyst.

The catalyst of certain examples in solid form, preferably in solid particulate form can be either supported on an external carrier material, like silica or alumina, or, in a particularly preferred embodiment, is free from an external carrier, however still being in solid form. For example, the solid catalyst is obtainable by a process in which (a) a liquid/liquid emulsion system is formed, said liquid/liquid emulsion system comprising a solution of the catalyst components (i) and (ii) dispersed in a solvent so as to form dispersed droplets; and (b) solid particles are formed by solidifying said dispersed droplets.

Viewed from another aspect the invention provides a process for the manufacture of a catalyst as hereinbefore defined comprising obtaining a complex of formula (I) and a cocatalyst as hereinbefore described;

forming a liquid/liquid emulsion system, which comprises a solution of catalyst components (i) and (ii) dispersed in a solvent, and solidifying said dispersed droplets to form solid particles.

Viewed from another aspect the invention provides the use in olefin polymerisation of a catalyst as hereinbefore defined, especially for the formation of a polyolefin, especially a polyethylene or polypropylene, such as a polypropylene homopolymer or copolymer.

Viewed from another aspect the invention provides a process for the polymerisation of at least one olefin comprising reacting said at least one olefin with a catalyst as hereinbefore described, especially for the formation of polypropylene.

DEFINITIONS

Throughout the description the following definitions are employed.

By free from an external carrier is meant that the catalyst does not contain an external support, such as an inorganic support, for example, silica or alumina, or an organic polymeric support material.

The term $C_{1-20}$ hydrocarbyl group therefore includes $C_{1-20}$ alkyl, $C_{2-20}$ alkenyl, $C_{2-20}$ alkynyl, $C_{3-20}$ cycloalkyl, $C_{3-20}$ cycloalkenyl, $C_{6-20}$ aryl groups, $C_{7-20}$ alkylaryl groups or $C_{7-20}$ arylalkyl groups or of course mixtures of these groups such as cycloalkyl substituted by alkyl. Linear and branched hydrocarbyl groups cannot contain cyclic units. Aliphatic hydrocarbyl groups cannot contain aryl rings.

Unless otherwise stated, preferred $C_{1-20}$ hydrocarbyl groups are $C_{1-20}$ alkyl, $C_{4-20}$ cycloalkyl, $C_{5-20}$ cycloalkylalkyl groups, $C_{7-20}$ alkylaryl groups, $C_{7-20}$ arylalkyl groups or $C_{6-20}$ aryl groups, especially $C_{1-10}$ alkyl groups, $C_{6-10}$ aryl groups, or $C_{7-12}$ arylalkyl groups, e.g. $C_{1-8}$ alkyl groups. Most especially preferred hydrocarbyl groups are methyl, ethyl, propyl, isopropyl, tertbutyl, isobutyl, $C_{5-6}$-cycloalkyl, cyclohexylmethyl, phenyl or benzyl.

The term halo includes fluoro, chloro, bromo and iodo groups, especially chloro groups, when relating to the complex definition.

The oxidation state of the metal ion is governed primarily by the nature of the metal ion in question and the stability of the individual oxidation states of each metal ion.

It will be appreciated that in the complexes of the invention, the metal ion M is coordinated by ligands X so as to satisfy the valency of the metal ion and to fill its available coordination sites. The nature of these σ-ligands can vary greatly.

Catalyst activity is defined in this application to be the amount of polymer produced/g catalyst/h. Catalyst metal activity is defined here to be the amount of polymer produced/g Metal/h. The term productivity is also sometimes used to indicate the catalyst activity although herein it designates the amount of polymer produced per unit weight of catalyst.

DETAILED DESCRIPTION

The complexes of certain examples are asymmetrical. That means simply that the two indenyl ligands forming the metallocene are different, that is, each indenyl ligand bears a set of substituents that are either chemically different, or located in different positions with respect to the other indenyl ligand. More precisely, they are chiral, racemic bridged bisindenyl metallocenes. Whilst the complexes may be in their syn configuration ideally, they are in their anti configuration. For the purpose of this invention, racemic-anti means that the two indenyl ligands are oriented in opposite directions with respect to the cyclopentadienyl-metal-cyclopentadienyl plane, while racemic-syn means that the two indenyl ligands are oriented in the same direction with respect to the cyclopentadienyl-metal-cyclopentadienyl plane, as shown in the Figure below.

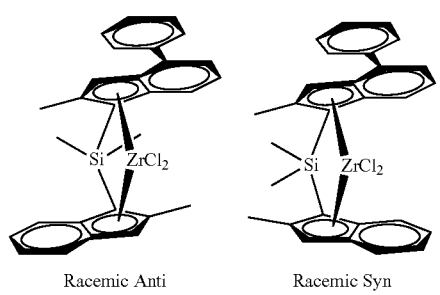

Racemic Anti          Racemic Syn

Formula (I) is intended to cover both syn and anti configurations, preferably anti. It is required in addition, that the group $R^{5'}$ is not hydrogen where the 5-position in the other ligand carries a hydrogen.

In fact, the metallocenes of certain examples are $C_1$-symmetric but they maintain a pseudo-$C_2$-symmetry since they maintain $C_2$-symmetry in close proximity of the metal center, although not at the ligand periphery. As will be seen, the use of two different indenyl ligands as described in this invention allows for a much finer structural variation, hence a more precise tuning of the catalyst performance, compared to the typical $C_2$-symmetric catalysts. By nature of their chemistry, both anti and syn enantiomer pairs are formed during the synthesis of the complexes. However, by using the ligands of this invention, separation of the preferred anti isomers from the syn isomers is straightforward.

It is preferred if the metallocenes of the invention are employed as the rac anti isomer. Ideally therefore at least 95% mol, such as at least 98% mol, especially at least 99% mol of the metallocene is in the racemic anti isomeric form.

In the catalysts of some examples:

M is preferably Zr.

Each X, which may be the same or different, is preferably a hydrogen atom, a halogen atom, a R, OR, $OSO_2CF_3$, OCOR, SR, $NR_2$ or $PR_2$ group wherein R is a linear or branched, cyclic or acyclic, $C_{1-20}$ alkyl, $C_{2-20}$ alkenyl, $C_{2-20}$ alkynyl, $C_{6-20}$ aryl, $C_{7-20}$ alkylaryl or $C_{7-20}$ arylalkyl radical; optionally containing heteroatoms belonging to groups 14-16. R is preferably a $C_{1-6}$ alkyl, phenyl or benzyl group.

Most preferably each X is independently a hydrogen atom, a halogen atom, $C_{1-6}$ alkoxy group or an R group, e.g. preferably a $C_{1-6}$ alkyl, phenyl or benzyl group. Most preferably X is chlorine or a methyl radical. Preferably both X groups are the same.

L is preferably an alkylene linker or a bridge comprising a heteroatom, such as silicon or germanium, e.g. —$SiR^8_2$—, wherein each $R^8$ is independently $C_{1-20}$ alkyl, $C_{3-10}$ cycloakyl, $C_{6-20}$ aryl or tri($C_{1-20}$ alkyl)silyl, such as trimethylsilyl. More preferably $R^8$ is $C_{1-6}$ alkyl, especially methyl or $C_{3-7}$ cycloalkyl, such as cyclohexyl. Most preferably, L is a dimethylsilyl or a methylcyclohexylsilyl bridge (i.e. Me-Si-cyclohexyl). It may also be an ethylene bridge.

$R^2$ and $R^{2'}$ can be different but they are preferably the same. $R^2$ and $R^{2'}$ are preferably a $C_{1-10}$ hydrocarbyl group such as $C_{1-6}$ hydrocarbyl group. More preferably it is a linear or branched $C_{1-10}$ alkyl group. More preferably it is a linear or branched $C_{1-6}$ alkyl group, especially linear $C_{1-6}$ alkyl group such as methyl or ethyl.

The $R^2$ and $R^{2'}$ groups can be interrupted by one or more heteroatoms, such as 1 or 2 heteroatoms, e.g. one heteroatom, selected from groups 14 to 16 of the periodic table. Such a heteroatom is preferably O, N or S, especially O. More preferably however the $R^2$ and $R^{2'}$ groups are free from heteroatoms. Most especially $R^2$ and $R^{2'}$ are methyl, especially both methyl.

The two Ar groups Ar and Ar' can be the same or different. It is preferred however if the Ar groups are different. The Ar' group may be unsubstituted. The Ar' is preferably a phenyl based group optionally substituted by groups $R^1$, especially an unsubstituted phenyl group.

The Ar group is preferably a $C_{6-20}$ aryl group such as a phenyl group or naphthyl group. Whilst the Ar group can be a heteroaryl group, such as carbazolyl, it is preferable that Ar is not a heteroaryl group. The Ar group can be unsubstituted or substituted by one or more groups $R^1$, more preferably by one or two $R^1$ groups, especially in position 4 of the aryl ring bound to the indenyl ligand or in the 3,5-positions.

In one embodiment both Ar and Ar' are unsubstituted. In another embodiment Ar' is unsubstituted and Ar is substituted by one or two groups $R^1$.

$R^1$ is preferably a $C_{1-20}$ hydrocarbyl group, such as a $C_{1-20}$ alkyl group. $R^1$ groups can be the same or different, preferably the same. More preferably, $R^1$ is a $C_{2-10}$ alkyl group such as $C_{3-8}$ alkyl group. Highly preferred groups are tert butyl or isopropyl groups. It is preferred if the group $R^1$ is bulky, i.e. is branched. Branching might be alpha or beta to the ring. Branched $C_{3-8}$ alkyl groups are also favoured therefore.

In a further embodiment, two $R^1$ groups on adjacent carbon atoms taken together can form a fused 5 or 6 membered non aromatic ring with the Ar group, said ring being itself optionally substituted with one or more groups $R^4$. Such a ring might form a tetrahydroindenyl group with the Ar ring or a tetrahydronaphthyl group.

If an $R^4$ group is present, there is preferably only 1 such group. It is preferably a $C_{1-10}$ alkyl group.

It is preferred if there is one or two $R^1$ groups present on the Ar group. Where there is one $R^1$ group present, the group is preferably para to the indenyl ring (4-position). Where two $R^1$ groups are present these are preferably at the 3 and 5 positions.

$R^{5'}$ is preferably a $C_{1-20}$ hydrocarbyl group containing one or more heteroatoms from groups 14-16 and optionally substituted by one or more halo atoms or $R^{5'}$ is a $C_{1-10}$ alkyl group, such as methyl but most preferably it is a group $Z'R^{3'}$.

$R^6$ and $R^{6'}$ may be the same or different. In one preferred embodiment one of $R^6$ and $R^{6'}$ is hydrogen, especially $R^6$. It is preferred if $R^6$ and $R^{6'}$ are not both hydrogen. If not hydrogen, it is preferred if each $R^6$ and $R^{6'}$ is preferably a $C_{1-20}$ hydrocarbyl group, such as a $C_{1-20}$ alkyl group or $C_{6-10}$ aryl group. More preferably, $R^6$ and $R^{6'}$ are a $C_{2-10}$ alkyl group such as $C_{3-8}$ alkyl group. Highly preferred groups are tert-butyl groups. It is preferred if $R^6$ and $R^{6'}$ are bulky, i.e. are branched. Branching might be alpha or beta to the ring. Branched $C_{3-8}$ alkyl groups are also favoured therefore.

The $R^7$ and $R^{7'}$ groups can be the same or different. Each $R^7$ and $R^{7'}$ group is preferably hydrogen, a $C_{1-6}$ alkyl group or is a group $ZR^3$. It is preferred if $R^7$ is hydrogen. It is preferred if $R^{7'}$ is hydrogen, $C_{1-6}$ alkyl or $ZR^3$. The combination of both $R^7$ and $R^{7'}$ being hydrogen is most preferred. It is also preferred if $ZR^3$ represents $OC_{1-6}$ alkyl, such as methoxy. It is also preferred is $R^{7'}$ represents $C_{1-6}$ alkyl such as methyl.

Z and Z' are O or S, preferably O.

$R^3$ is preferably a $C_{1-10}$ hydrocarbyl group, especially a $C_{1-10}$ alkyl group, or aryl group optionally substituted by one or more halo groups. Most especially $R^3$ is a $C_{1-6}$ alkyl group, such as a linear $C_{1-6}$ alkyl group, e.g. methyl or ethyl $R^{3'}$ is preferably a $C_{1-10}$ hydrocarbyl group, especially a $C_{1-10}$ alkyl group, or aryl group optionally substituted by one or more halo groups. Most especially $R^{3'}$ is a $C_{1-6}$ alkyl group, such as a linear $C_{1-6}$ alkyl group, e.g. methyl or ethyl or it is a phenyl based radical optionally substituted with one or more halo groups such as Ph or $C_6F_5$.

Thus, preferred complexes of the invention are of formula (II') or (II)

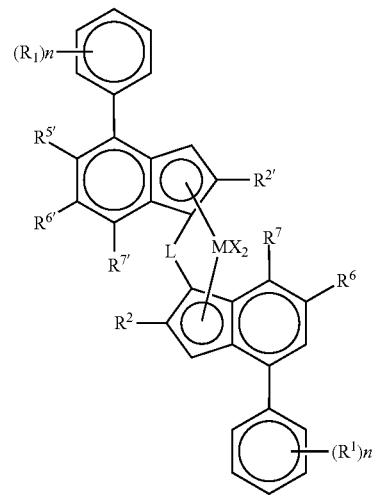

(II')

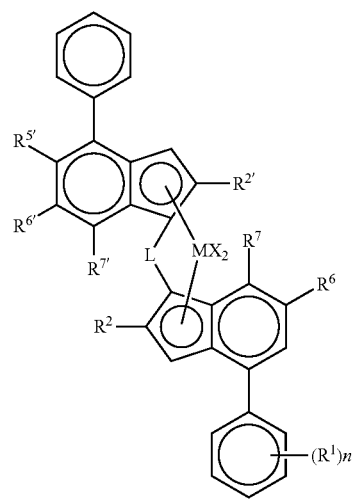

(II)

wherein

M is zirconium or hafnium;

each X is a sigma ligand, preferably each X is independently a hydrogen atom, a halogen atom, $C_{1-6}$ alkoxy group, $C_{1-6}$ alkyl, phenyl or benzyl group;

L is a divalent bridge selected from —R'$_2$C—, —R'$_2$C—CR'$_2$—, —R'$_2$Si—, —R'$_2$Si—SiR'$_2$—, —R'$_2$Ge—, wherein each R' is independently a hydrogen atom, $C_{1-20}$ alkyl, $C_{3-10}$ cycloalkyl, tri($C_{1-20}$-alkyl)silyl, $C_{6-20}$-aryl, $C_{7-20}$ arylalkyl or $C_{7-20}$ alkylaryl;

each $R^2$ or $R^{2'}$ is a $C_{1-10}$ alkyl group;

$R^{5'}$ is a $C_{1-10}$ alkyl group or $Z'R^{3'}$ group;

$R^6$ is hydrogen or a $C_{1-10}$ alkyl group;

$R^{6'}$ is a $C_{1-10}$ alkyl group or $C_{6-10}$ aryl group;

$R^7$ is hydrogen, a $C_{1-6}$ alkyl group or $ZR^3$ group;

$R^{7'}$ is hydrogen or a $C_{1-10}$ alkyl group;

Z and Z' are independently O or S;

$R^{3'}$ is a $C_{1-10}$ alkyl group, or a $C_{6-10}$ aryl group optionally substituted by one or more halo groups;

$R^3$ is a $C_{1-10}$-alkyl group;

each n is independently 0 to 4, e.g. 0, 1 or 2; and each $R^1$ is independently a $C_{1-20}$ hydrocarbyl group, e.g. $C_{1-10}$ alkyl group.

Viewed from another aspect the invention provides a complex of formula (III') or (III):

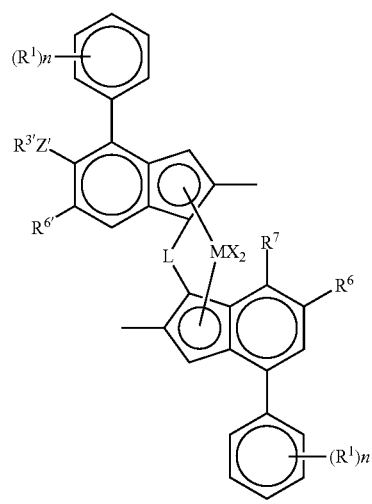

(III')

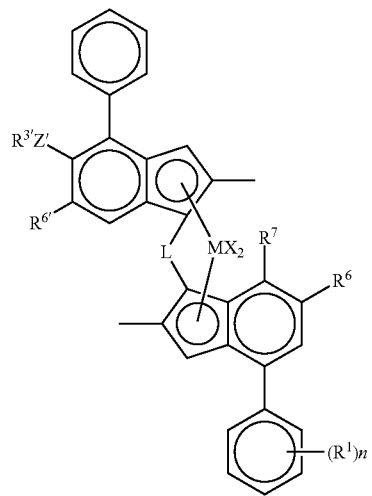

(III)

M is zirconium or hafnium;

each X is a sigma ligand, preferably each X is independently a hydrogen atom, a halogen atom, $C_{1-6}$ alkoxy group, $C_{1-6}$ alkyl, phenyl or benzyl group;

L is a divalent bridge selected from —$R'_2C$— or —$R'_2Si$— wherein each R' is independently a hydrogen atom, $C_{1-20}$ alkyl or $C_{3-10}$ cycloalkyl;

$R^6$ is hydrogen or a $C_{1-10}$ alkyl group;

$R^{6'}$ is a $C_{1-10}$ alkyl group or $C_{6-10}$ aryl group;

$R^7$ is hydrogen, $C_{1-6}$ alkyl or $OC_{1-6}$ alkyl;

Z' is O or S;

$R^{3'}$ is a $C_{1-10}$ alkyl group, or $C_{6-10}$ aryl group optionally substituted by one or more halo groups;

n is independently 0 to 4, e.g. 0, 1 or 2; and each $R^1$ is independently a $C_{1-10}$ alkyl group.

Viewed from a further preferred aspect the invention provides a complex of formula (IV') or (IV):

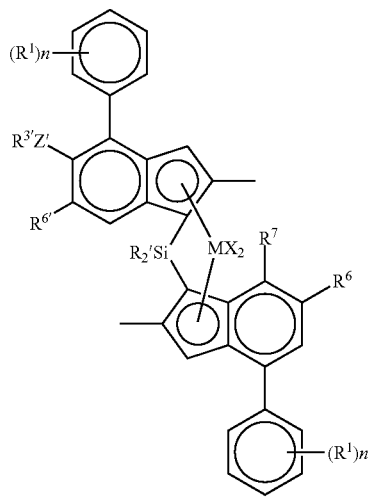

(IV')

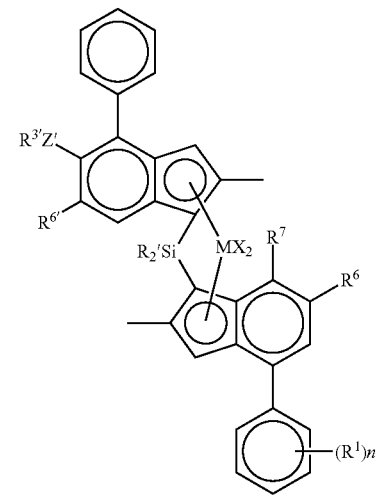

(IV)

M is zirconium or hafnium;

each X is a sigma ligand, preferably each X is independently a hydrogen atom, a halogen atom, $C_{1-6}$-alkoxy group, $C_{1-6}$-alkyl, phenyl or benzyl group;

each R' is independently a hydrogen atom, $C_{1-20}$ alkyl or $C_{3-7}$ cycloalkyl;

$R^6$ is hydrogen or a $C_{1-10}$ alkyl group;

$R^{6'}$ is a $C_{1-10}$ alkyl group or $C_{6-10}$ aryl group;

$R^7$ is hydrogen, $C_{1-6}$ alkyl or $OC_{1-6}$ alkyl;

Z' is O or S;

R$^{3'}$ is a C$_{1-10}$ alkyl group, or C$_{6-10}$ aryl group optionally substituted by one or more halo groups;

n is independently 0, 1 to 2; and each R$^1$ is independently a C$_{3-8}$ alkyl group.

Most especially, the preferred complex of the invention is of formula (V') or (V):

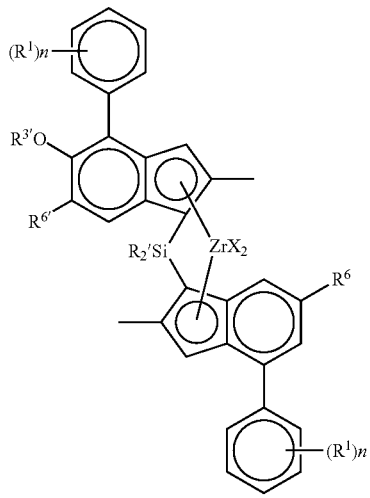

(V')

(V)

wherein each X is a sigma ligand, preferably each X is independently a hydrogen atom, a halogen atom, C$_{1-6}$-alkoxy group, C$_{1-6}$-alkyl, phenyl or benzyl group;

R' is independently a C$_{1-6}$ alkyl or C$_{3-10}$ cycloalkyl;

R$^1$ is independently C$_{3-8}$ alkyl;

R$^6$ is hydrogen or a C$_{3-8}$ alkyl group;

R$^{6'}$ is a C$_{3-8}$ alkyl group or C$_{6-10}$ aryl group;

R$^{3'}$ is a C$_{1-6}$ alkyl group, or C$_{6-10}$ aryl group optionally substituted by one or more halo groups; and n is independently 0, 1 or 2.

Particular compounds of the invention include:

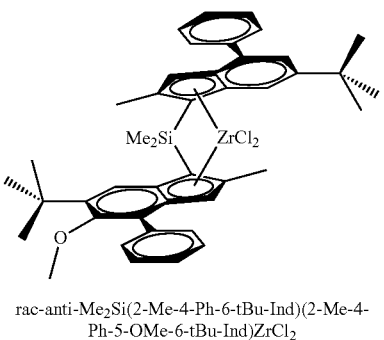

rac-anti-Me$_2$Si(2-Me-4-Ph-6-tBu-Ind)(2-Me-4-Ph-5-OMe-6-tBu-Ind)ZrCl$_2$

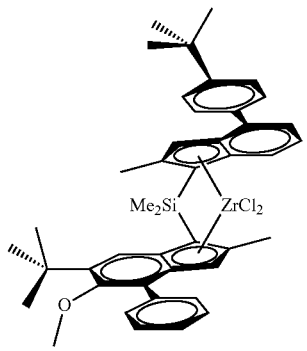

rac-anti-Me$_2$Si(2-Me-4-(p-tBuPh)-Ind)(2-Me-4-Ph-5-OMe-6-tBu-Ind)ZrCl$_2$

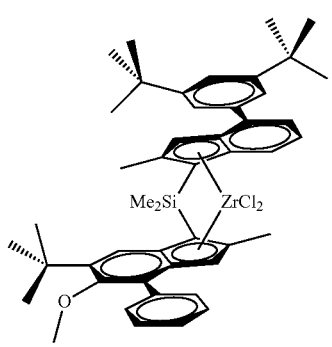

rac-anti-Me$_2$Si(2-Me-4-(3,5-di-tBuPh)-6-tBu-Ind)(2-Me-4-Ph-5-OMe-6-tBu-Ind)ZrCl$_2$

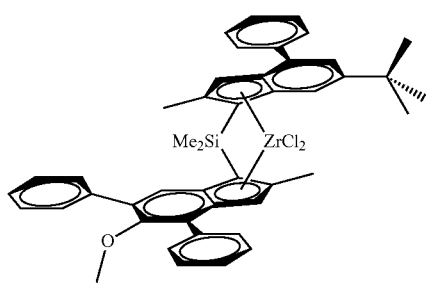
rac-anti-Me₂Si(2-Me-4-Ph-6-tBu-Ind)(2-Me-4,6-di-Ph-5-OMe-Ind)ZrCl₂
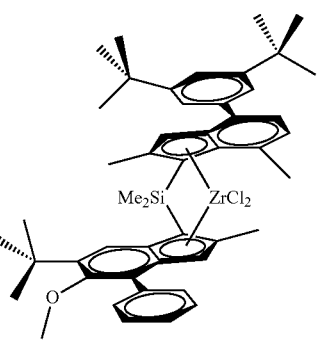
rac-anti-Me₂Si(2-Me-4-(3,5-di-tBuPh)-7-Me-Ind)(2-Me-4-Ph-5-OMe-6-tBu-Ind)ZrCl₂
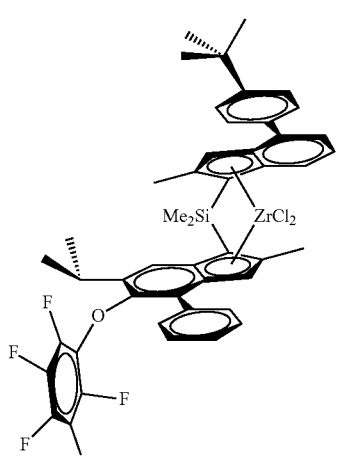
rac-anti-Me₂Si(2-Me-4-(p-tBuPh)-Ind)(2-Me-4-Ph-5-OC₆F₅)-6-iPr-Ind)ZrCl₂
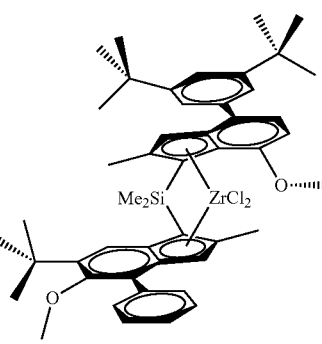
rac-anti-Me₂Si(2-Me-4-(3,5-di-tBuPh)-7-OMe-Ind)(2-Me-4-Ph-5-OMe-6-tBu-Ind)ZrCl₂
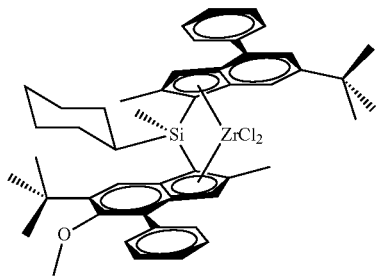
rac-anti-Me(CyHex)Si(2-Me-4-Ph-6-tBu-Ind)(2-Me-4-Ph-5-OMe-6-tBu-Ind)ZrCl₂
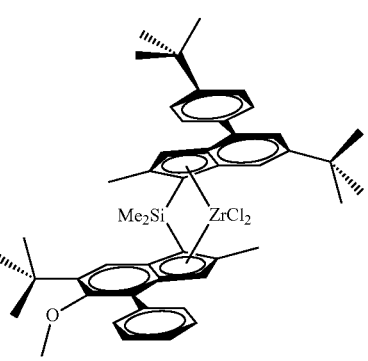
rac-anti-Me₂Si(2-Me-4-(p-tBuPh)-6-tBu-Ind)(2-Me-4-Ph-5-OMe-6-tBu-Ind)ZrCl₂

-continued

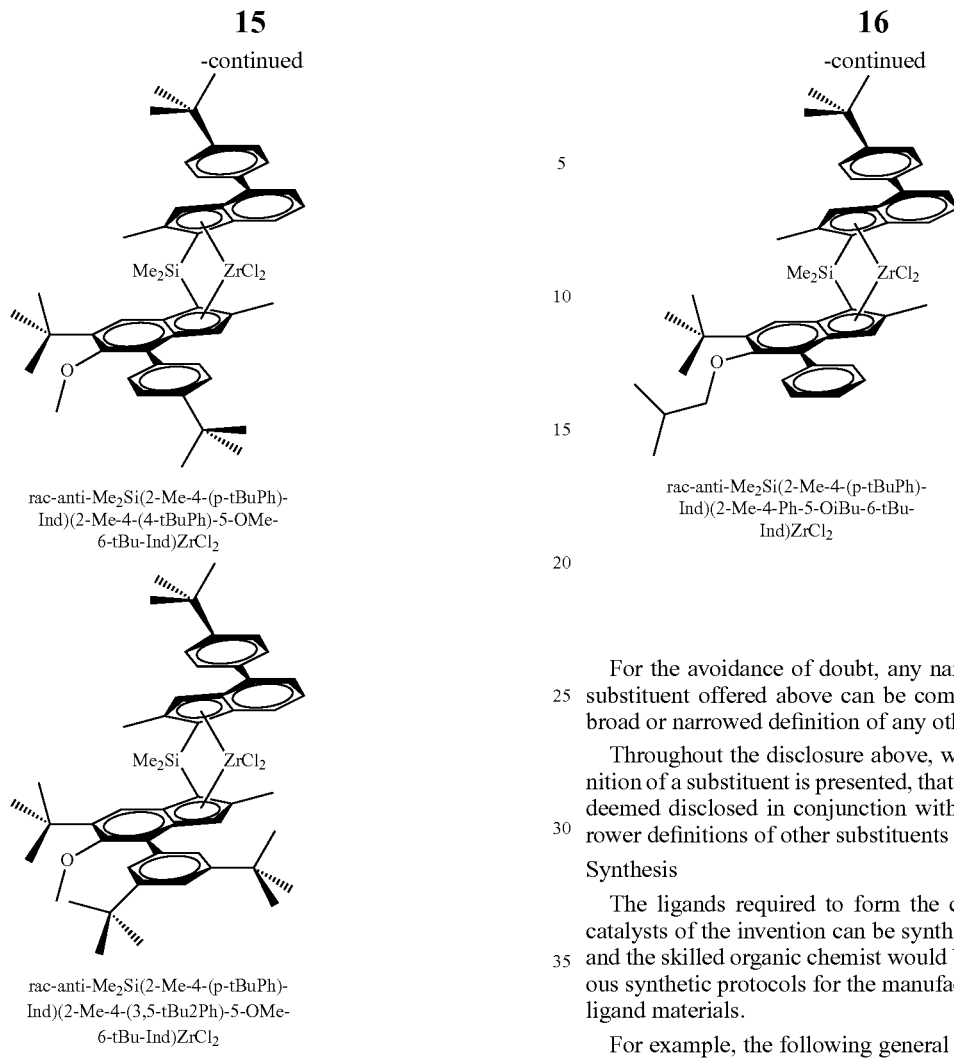

rac-anti-Me₂Si(2-Me-4-(p-tBuPh)-
Ind)(2-Me-4-(4-tBuPh)-5-OMe-
6-tBu-Ind)ZrCl₂ rac-anti-Me₂Si(2-Me-4-(p-tBuPh)-
Ind)(2-Me-4-Ph-5-OiBu-6-tBu-
Ind)ZrCl₂ rac-anti-Me₂Si(2-Me-4-(p-tBuPh)-
Ind)(2-Me-4-(3,5-tBu2Ph)-5-OMe-
6-tBu-Ind)ZrCl₂

For the avoidance of doubt, any narrower definition of a substituent offered above can be combined with any other broad or narrowed definition of any other substituent.

Throughout the disclosure above, where a narrower definition of a substituent is presented, that narrower definition is deemed disclosed in conjunction with all broader and narrower definitions of other substituents in the application.

Synthesis

The ligands required to form the complexes and hence catalysts of the invention can be synthesised by any process and the skilled organic chemist would be able to devise various synthetic protocols for the manufacture of the necessary ligand materials.

For example, the following general synthetic scheme can be used:

Scheme 1

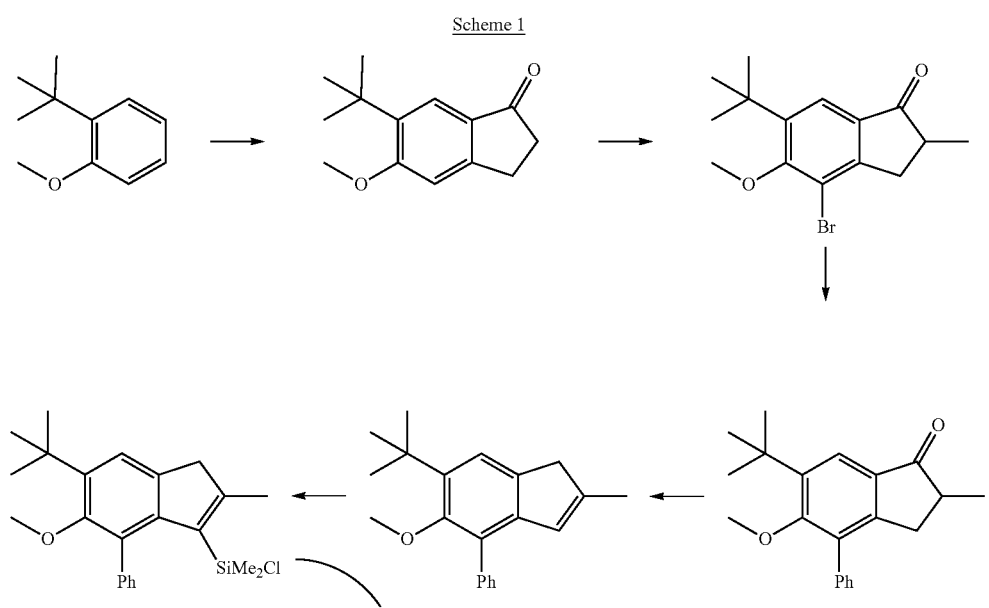

-continued

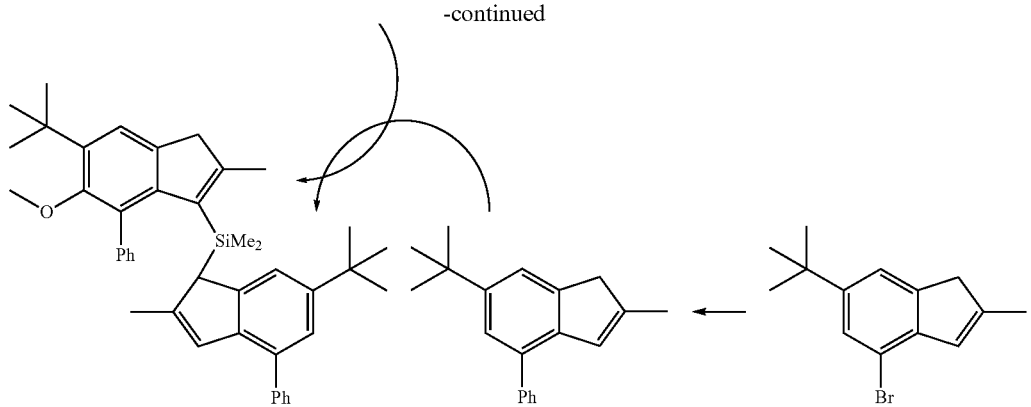

Suitable reagents for this transformation are given in the examples section. Whilst this scheme refers to specific compounds, the general principles displayed here apply to the metallocenes of the invention. The important point to remember is that as the ligands are asymmetric, a conventional reaction with $SiMe_2Cl_2$ cannot be effected to bridge two ligands as that leads to symmetrical products. Instead, each ligand has to be attached to the bridge stepwise with control over the reaction stoichiometry.

Of particular interest is the synthesis of compounds having an alkoxy group at the 7-position of the eventual metallocene. The present inventors have devised a new process for the synthesis of the precursors needed to make such 7 substituted materials.

The process starts from the intermediate:

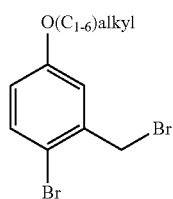

where the alkyl is preferably methyl. This intermediate is readily prepared and the examples offer various options for its preparation. This intermediate can then be reacted with diethyl methylmalonate and cyclised in this process:

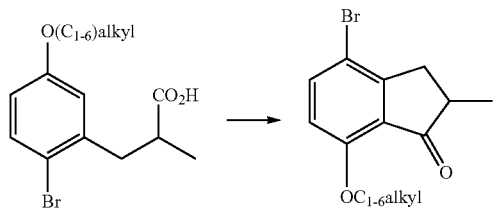

Reduction of the carbonyl and alkylation to form an alkoxide and subsequent grignard chemistry at the 4-position introduces therefore the Ar type substituent group whilst also eliminating the alkoxide group to form a double bond at the "1-2" position of the 5-membered ring:

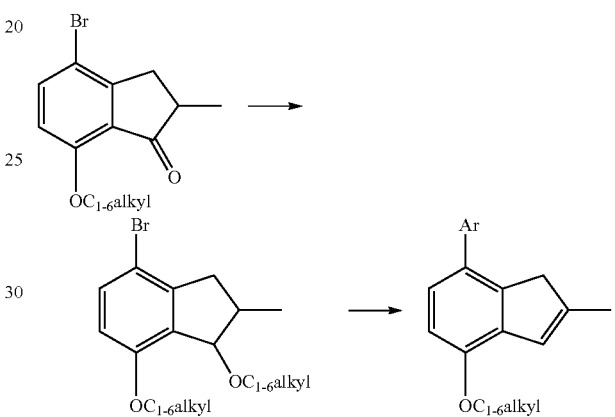

Reaction with a bridging group precursor (L) such as $SiMe_2Cl_2$ in the presence of base affords preferentially the compounds in which the L group binds at the 1-position with the double bond shifted to the 2-3 position of the ring. This intermediate can then be used in the further metallocene preparation as is well known. Note therefore that the method provides a 7-position alkoxy group.

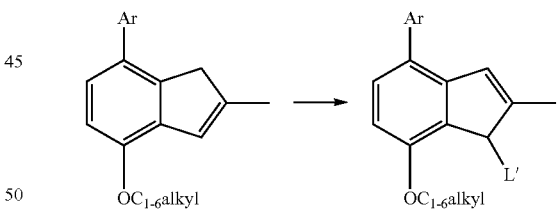

The key to the presence of the 7-position alkoxy group is the formation of the bicyclic ring system in the presence of the "7-position" alkoxide group and this forms a further aspect of the invention.

Thus viewed from another aspect the invention provides a process for the preparation of a compound of formula (VI)

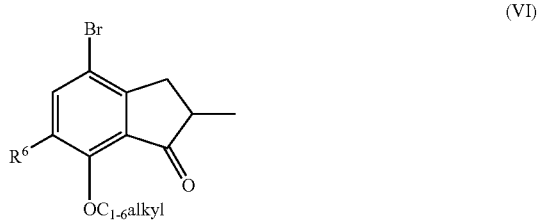

(VI)

wherein R⁶ is as hereinbefore defined, preferably H, comprising cyclising a compound

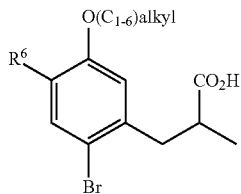

preferably in the presence of $P_4O_{10}$ and $MeSO_3H$. (Eatons reagent).

In a further embodiment the compound of formula (VI) is reduced, e.g. in the presence of sodium borohydride and reacted with an alkylating agent such as MeI to form the compound (VII)

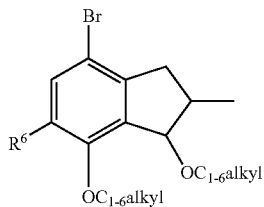

(VII)

In a further embodiment the compound of formula (VII) is converted to

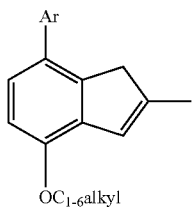

where Ar is as hereinbefore defined.

Intermediates

Whilst the invention primarily relates to catalysts, it will be appreciated that the complexes of the invention and the ligands used to form those complexes are also new. The invention further relates therefore to complexes, including the examples of formula (I) and ligands of formula (I') from which the $MX_2$ coordination has been removed and the proton returned to the indenyl.

Ligands of interest are therefore of formula (I')

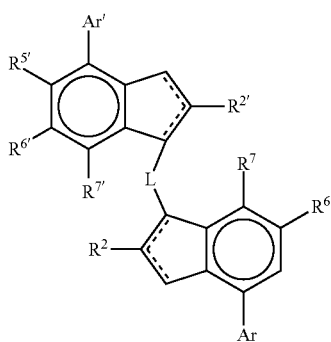

(I')

wherein the substituents are as hereinbefore defined and the dotted lines represent a double bond present in between carbons 1 and 2 or 2 and 3 of the indenyl ring. It will be appreciated therefore that this molecule contains double bond isomers. By double bond isomers is meant the compounds where the double bond is positioned between the 2 and 3 atoms rather than 1 and 2 atoms of the bicyclic ring. It may be that more than one double bond isomer is present in a sample. Preferred ligands are analogues of the complexes described above from which $MX_2$ coordination has been removed and the proton returned to the indenyl.

Cocatalyst

To form an active catalytic species it is normally necessary to employ a cocatalyst as is well known in the art. Cocatalysts comprising one or more compounds of Group 13 metals, like organoaluminium compounds or borates used to activate metallocene catalysts are suitable for use in certain examples.

The olefin polymerisation catalyst system may comprise (i) a complex in which the metal ion is coordinated by a ligand; and normally (ii) an aluminium alkyl compound (or other appropriate cocatalyst), or the reaction product thereof. Thus the cocatalyst is preferably an alumoxane, like MAO or an alumoxane other than MAO.

Borate cocatalysts can also be employed. It will be appreciated by the skilled man that where boron based cocatalysts are employed, it is normal to preactivate the complex by reaction thereof with an aluminium alkyl compound, such as TIBA. This procedure is well known and any suitable aluminium alkyl, e.g. $Al(C_{1-6}\text{-alkyl})_3$, can be used.

Boron based cocatalysts of interest include those of formula $$BY_3$$

wherein Y is the same or different and is a hydrogen atom, an alkyl group of from 1 to about 20 carbon atoms, an aryl group of from 6 to about 15 carbon atoms, alkylaryl, arylalkyl, haloalkyl or haloaryl each having from 1 to 10 carbon atoms in the alkyl radical and from 6-20 carbon atoms in the aryl radical or fluorine, chlorine, bromine or iodine. Preferred examples for Y are methyl, propyl, isopropyl, isobutyl or trifluoromethyl, unsaturated groups such as aryl or haloaryl like phenyl, tolyl, benzyl groups, p-fluorophenyl, 3,5-difluorophenyl, pentachlorophenyl, pentafluorophenyl, 3,4,5-trifluorophenyl and 3,5-di(trifluoromethyl)phenyl. Preferred options are trifluoroborane, triphenylborane, tris(4-fluorophenyl)borane, tris(3,5-difluorophenyl)borane, tris(4-fluoromethylphenyl)borane, tris(2,4,6-trifluorophenyl)borane, tris(penta-fluorophenyl)borane, tris(tolyl)borane, tris(3,5-dimethyl-phenyl)borane, tris(3,5-difluorophenyl)borane and/or tris(3,4,5-trifluorophenyl)borane.

Particular preference is given to tris(pentafluorophenyl)borane.

It is preferred however is borates are used, i.e. compounds containing a borate 3+ ion. Such ionic cocatalysts preferably contain a non-coordinating anion such as tetrakis(pentafluorophenyl)borate and tetraphenylborate. Suitable counterions are protonated amine or aniline derivatives such as methylammonium, anilinium, dimethylammonium, diethylammonium, N-methylanilinium, diphenylammonium, N,N-dimethylanilinium, trimethylammonium, triethylammonium, tri-n-butylammonium, methyl diphenyl ammonium, pyridinium, p-bromo-N,N-dimethylanilinium or p-nitro-N, N-dimethylanilinium. Preferred ionic compounds which can be used according to the present invention include: triethylammoniumtetra(phenyl)borate, tributylammoniumtetra(phenyl)borate, trimethylammoniumtetra(tolyl)borate, tributylammoniumtetra(tolyl)borate, tributylammoniumtetra(pentafluorophenyl)borate, tripropylammoniumtetra(dimethylphenyl)borate, tributylammoniumtetra(trifluoromethylphenyl)borate, tributylammoniumtetra(4-fluorophenyl)borate, N,N- dimethylcyclohexylammoniumtetrakis(pentafluorophenyl) borate, N,N-dimethylbenzylammoniumtetrakis(pentafluorophenyl)borate, N,N-dimethylaniliniumtetra(phenyl)borate, N,N-diethylaniliniumtetra(phenyl)borate, N,N-dimethylaniliniumtetrakis(pentafluorophenyl)borate, N,N-di(propyl)ammoniumtetrakis(pentafluorophenyl)borate, di(cyclohexyl)ammoniumtetrakist(pentafluorophenyl)borate, triphenylphosphoniumtetrakis(phenyl)borate, triethylphosphoniumtetrakis(phenyl)borate, diphenylphosphoniumtetrakis(phenyl)borate, tri(methylphenyl)phosphoniumtetrakis(phenyl)borate, tri(dimethylphenyl)phosphoniumtetrakis(phenyl)borate, triphenylcarbeniumtetrakis(pentafluorophenyl)borate, or ferroceniumtetrakis(pentafluorophenyl)borate. Preference is given to triphenylcarbeniumtetrakis(pentafluorophenyl)borate, N,N-dimethylcyclohexylammoniumtetrakis(pentafluorophenyl)borate or N,N-dimethylbenzylammoniumtetrakis(pentafluorophenyl)borate.

The use of $B(C_6F_5)_3$, $C_6H_5N(CH_3)_2H:B(C_6F_5)_4$, $(C_6H_5)_3C:B(C_6F_5)_4$ or $Ni(CN)_4[B(C_6F_5)_3]_4{}^{2-}$ is especially preferred.

Suitable amounts of cocatalyst will be well known to the skilled man.

Catalyst Manufacture

The metallocene complex of the present invention can be used in combination with a suitable cocatalyst as a catalyst for the polymerization of olefins, e.g. in a solvent such as toluene or an aliphatic hydrocarbon, (i.e. for polymerization in solution), as it is well known in the art. Preferably, polymerization of olefins, especially propylene, takes place in the condensed phase or in gas phase.

The catalyst may be used in supported or unsupported form. The particulate support material used is preferably an organic or inorganic material, such as silica, alumina or zirconia or a mixed oxide such as silica-alumina, in particular silica, alumina or silica-alumina. The use of a silica support is preferred. The skilled man is aware of the procedures required to support a metallocene catalyst.

Especially preferably the support is a porous material so that the complex may be loaded into the pores of the support, e.g. using a process analogous to those described in WO94/14856 (Mobil), WO95/12622 (Borealis) and WO2006/097497. The particle size is not critical but is preferably in the range 5 to 200 μm, more preferably 20 to 80 μm. The use of these supports is routine in the art.

In an alternative embodiment, no support is used at all. Such a catalyst can be prepared in solution, for example in an aromatic solvent like toluene, by contacting the metallocene (as a solid or as a solution) with the cocatalyst, for example methylaluminoxane or a borane or a borate salt previously dissolved in an aromatic solvent, or can be prepared by sequentially adding the dissolved catalyst components to the polymerization medium. In a preferred embodiment, the metallocene (when X differs from alkyl or hydrogen) is prereacted with an aluminum alkyl, in a ratio metal/aluminum of from 1:1 up to 1:500, preferably from 1:1 up to 1:250, and then combined with a solution of the borane or borate cocatalyst dissolved in an aromatic solvent, either in a separate vessel or directly into the polymerization reactor. Preferred metal/boron ratios are between 1:1 and 1:100, more preferably 1:1 to 1:10.

In one particularly preferred embodiment, no external carrier is used but the catalyst is still presented in solid particulate form. Thus no external support material such as inert organic or inorganic carrier, such as for example silica as described above is employed.

In order to provide the catalyst of the invention in solid form but without using an external carrier, it is preferred if a liquid/liquid emulsion system is used. The process involves forming dispersing catalyst components (i) and (ii) in a solvent, and solidifying said dispersed droplets to form solid particles.

In particular, the method involves preparing a solution of one or more catalyst components; dispersing said solution in an solvent to form an emulsion in which said one or more catalyst components are present in the droplets of the dispersed phase; immobilising the catalyst components in the dispersed droplets, in the absence of an external particulate porous support, to form solid particles comprising the said catalyst, and optionally recovering said particles.

This process enables the manufacture of active catalyst particles with improved morphology, e.g. with a predetermined spherical shape, surface properties and particle size and without using any added external porous support material, such as an inorganic oxide, e.g. silica. By the term "preparing a solution of one or more catalyst components" is meant that the catalyst forming compounds may be combined in one solution which is dispersed to the immiscible solvent, or, alternatively, at least two separate catalyst solutions for each part of the catalyst forming compounds may be prepared, which are then dispersed successively to the solvent.

In a preferred method for forming the catalyst at least two separate solutions for each or part of said catalyst may be prepared, which are then dispersed successively to the immiscible solvent.

More preferably, a solution of the complex comprising the transition metal compound and the cocatalyst is combined with the solvent to form an emulsion wherein that inert solvent forms the continuous liquid phase and the solution comprising the catalyst components forms the dispersed phase (discontinuous phase) in the form of dispersed droplets. The droplets are then solidified to form solid catalyst particles, and the solid particles are separated from the liquid and optionally washed and/or dried. The solvent forming the continuous phase may be immiscible to the catalyst solution at least at the conditions (e.g. temperatures) used during the dispersing step.

The term "immiscible with the catalyst solution" means that the solvent (continuous phase) is fully immiscible or partly immiscible i.e. not fully miscible with the dispersed phase solution.

Preferably said solvent is inert in relation to the compounds of the catalyst system to be produced. Full disclosure of the necessary process can be found in WO03/051934 which is herein incorporated by reference.

The inert solvent must be chemically inert at least at the conditions (e.g. temperature) used during the dispersing step. Preferably, the solvent of said continuous phase does not contain dissolved therein any significant amounts of catalyst forming compounds. Thus, the solid particles of the catalyst are formed in the droplets from the compounds which originate from the dispersed phase (i.e. are provided to the emulsion in a solution dispersed into the continuous phase).

The terms "immobilisation" and "solidification" are used herein interchangeably for the same purpose, i.e. for forming free flowing solid catalyst particles in the absence of an external porous particulate carrier, such as silica. The solidification happens thus within the droplets. Said step can be effected in various ways as disclosed in said WO03/051934 Preferably solidification is caused by an external stimulus to the emulsion system such as a temperature change to cause the solidification. Thus in said step the catalyst component (s) remain "fixed" within the formed solid particles. It is also possible that one or more of the catalyst components may take part in the solidification/immobilisation reaction.

Accordingly, solid, compositionally uniform particles having a predetermined particle size range can be obtained.

Furthermore, the particle size of the catalyst particles of the invention can be controlled by the size of the droplets in the solution, and spherical particles with a uniform particle size distribution can be obtained.

The invention is also industrially advantageous, since it enables the preparation of the solid particles to be carried out as a one-pot procedure. Continuous or semicontinuous processes are also possible for producing the catalyst.

Dispersed Phase

The principles for preparing two phase emulsion systems are known in the chemical field. Thus, in order to form the two phase liquid system, the solution of the catalyst component (s) and the solvent used as the continuous liquid phase have to be essentially immiscible at least during the dispersing step. This can be achieved in a known manner e.g. by choosing said two liquids and/or the temperature of the dispersing step/solidifying step accordingly.

A solvent may be employed to form the solution of the catalyst component (s). Said solvent is chosen so that it dissolves said catalyst component (s). The solvent can be preferably an organic solvent such as used in the field, comprising an optionally substituted hydrocarbon such as linear or branched aliphatic, alicyclic or aromatic hydrocarbon, such as a linear or cyclic alkane, an aromatic hydrocarbon and/or a halogen containing hydrocarbon.

Examples of aromatic hydrocarbons are toluene, benzene, ethylbenzene, propylbenzene, butylbenzene and xylene. Toluene is a preferred solvent. The solution may comprise one or more solvents. Such a solvent can thus be used to facilitate the emulsion formation, and usually does not form part of the solidified particles, but e.g. is removed after the solidification step together with the continuous phase.

Alternatively, a solvent may take part in the solidification, e.g. an inert hydrocarbon having a high melting point (waxes), such as above 40° C., suitably above 70° C., e.g. above 80° C. or 90° C., may be used as solvents of the dispersed phase to immobilise the catalyst compounds within the formed droplets.

In another embodiment, the solvent consists partly or completely of a liquid monomer, e.g. liquid olefin monomer designed to be polymerised in a "prepolymerisation" immobilisation step.

Continuous Phase

The solvent used to form the continuous liquid phase is a single solvent or a mixture of different solvents and may be immiscible with the solution of the catalyst components at least at the conditions (e.g. temperatures) used during the dispersing step. Preferably said solvent is inert in relation to said compounds.

The term "inert in relation to said compounds" means herein that the solvent of the continuous phase is chemically inert, i.e. undergoes no chemical reaction with any catalyst forming component. Thus, the solid particles of the catalyst are formed in the droplets from the compounds which originate from the dispersed phase, i.e. are provided to the emulsion in a solution dispersed into the continuous phase.

It is preferred that the catalyst components used for forming the solid catalyst will not be soluble in the solvent of the continuous liquid phase. Preferably, said catalyst components are essentially insoluble in said continuous phase forming solvent.

Solidification takes place essentially after the droplets are formed, i.e. the solidification is effected within the droplets e.g. by causing a solidifying reaction among the compounds present in the droplets. Furthermore, even if some solidifying agent is added to the system separately, it reacts within the droplet phase and no catalyst forming components go into the continuous phase.

The term "emulsion" used herein covers both bi- and multiphasic systems.

In a preferred embodiment said solvent forming the continuous phase is an inert solvent including a halogenated organic solvent or mixtures thereof, preferably fluorinated organic solvents and particularly semi, highly or perfluorinated organic solvents and functionalised derivatives thereof. Examples of the above-mentioned solvents are semi, highly or perfluorinated hydrocarbons, such as alkanes, alkenes and cycloalkanes, ethers, e.g. perfluorinated ethers and amines, particularly tertiary amines, and functionalised derivatives thereof. Preferred are semi, highly or perfluorinated, particularly perfluorinated hydrocarbons, e.g. perfluorohydrocarbons of e.g. C3-C30, such as C4-C10. Specific examples of suitable perfluoroalkanes and perfluorocycloalkanes include perfluoro-hexane, -heptane, -octane and -(methylcyclohexane). Semi fluorinated hydrocarbons relates particularly to semifluorinated n-alkanes, such as perfluoroalkyl-alkane.

"Semi fluorinated" hydrocarbons also include such hydrocarbons wherein blocks of —C—F and —C—H alternate. "Highly fluorinated" means that the majority of the —C—H units are replaced with —C—F units. "Perfluorinated" means that all —C—H units are replaced with —C—F units. See the articles of A. Enders and G. Maas in "Chemie in unserer Zeit", 34. Jahrg. 2000, Nr. 6, and of Pierandrea Lo Nostro in "Advances in Colloid and Interface Science", 56 (1995) 245-287, Elsevier Science.

Dispersing Step

The emulsion can be formed by any means known in the art: by mixing, such as by stirring said solution vigorously to said solvent forming the continuous phase or by means of mixing mills, or by means of ultra sonic wave, or by using a so called phase change method for preparing the emulsion by first forming a homogeneous system which is then transferred by changing the temperature of the system to a biphasic system so that droplets will be formed.

The two phase state is maintained during the emulsion formation step and the solidification step, as, for example, by appropriate stirring.

Additionally, emulsifying agents/emulsion stabilisers can be used, preferably in a manner known in the art, for facilitating the formation and/or stability of the emulsion. For the said purposes e.g. surfactants, e.g. a class based on hydrocarbons (including polymeric hydrocarbons with a molecular weight e.g. up to 10 000 and optionally interrupted with a heteroatom(s)), preferably halogenated hydrocarbons, such as semi- or highly fluorinated hydrocarbons optionally having a functional group selected e.g. from —OH, —SH, NH$_2$, NR"$_2$. —COOH, —COONH$_2$, oxides of alkenes, —CR"=CH$_2$, where R" is hydrogen, or C1-C20 alkyl, C2-20-alkenyl or C2-20-alkynyl group, oxo-groups, cyclic ethers and/or any reactive derivative of these groups, like alkoxy, or carboxylic acid alkyl ester groups, or, preferably semi-, highly- or perfluorinated hydrocarbons having a functionalised terminal, can be used. The surfactants can be added to the catalyst solution, which forms the dispersed phase of the emulsion, to facilitate the forming of the emulsion and to stabilize the emulsion.

Alternatively, an emulsifying and/or emulsion stabilising aid can also be formed by reacting a surfactant precursor bearing at least one functional group with a compound reactive with said functional group and present in the catalyst solution or in the solvent forming the continuous phase. The obtained reaction product acts as the actual emulsifying aid and or stabiliser in the formed emulsion system.

Examples of the surfactant precursors usable for forming said reaction product include e.g. known surfactants which bear at least one functional group selected e.g. from —OH, —SH, $NH_2$, $NR''_2$. —COOH, —$COONH_2$, oxides of alkenes, —CR''=$CH_2$, where R'' is hydrogen, or C1-C20 alkyl, C2-20-alkenyl or C2-20-alkynyl group, oxo-groups, cyclic ethers with 3 to 5 ring atoms, and/or any reactive derivative of these groups, like alkoxy or carboxylic acid alkyl ester groups; e.g. semi-, highly or perfluorinated hydrocarbons bearing one or more of said functional groups. Preferably, the surfactant precursor has a terminal functionality as defined above.

The compound reacting with such surfactant precursor is preferably contained in the catalyst solution and may be a further additive or one or more of the catalyst forming compounds. Such compound is e.g. a compound of group 13 (e.g. MAO and/or an aluminium alkyl compound and/or a transition metal compound).

If a surfactant precursor is used, it is preferably first reacted with a compound of the catalyst solution before the addition of the transition metal compound. In one embodiment e.g. a highly fluorinated C1-n (suitably C4-30- or C5-15) alcohol (e.g. highly fluorinated heptanol, octanol or nonanol), oxide (e.g. propenoxide) or acrylate ester is reacted with a cocatalyst to form the "actual" surfactant. Then, an additional amount of cocatalyst and the transition metal compound is added to said solution and the obtained solution is dispersed to the solvent forming the continuous phase. The "actual" surfactant solution may be prepared before the dispersing step or in the dispersed system. If said solution is made before the dispersing step, then the prepared "actual" surfactant solution and the transition metal solution may be dispersed successively (e.g. the surfactant solution first) to the immiscible solvent, or be combined together before the dispersing step.

Solidification

The solidification of the catalyst component(s) in the dispersed droplets can be effected in various ways, e.g. by causing or accelerating the formation of said solid catalyst forming reaction products of the compounds present in the droplets. This can be effected, depending on the used compounds and/or the desired solidification rate, with or without an external stimulus, such as a temperature change of the system.

In a particularly preferred embodiment, the solidification is effected after the emulsion system is formed by subjecting the system to an external stimulus, such as a temperature change. Temperature differences of e.g. 5 to 100° C., such as 10 to 100° C., or 20 to 90° C., such as 50 to 90° C.

The emulsion system may be subjected to a rapid temperature change to cause a fast solidification in the dispersed system. The dispersed phase may e.g. be subjected to an immediate (within milliseconds to few seconds) temperature change in order to achieve an instant solidification of the component (s) within the droplets. The appropriate temperature change, i.e. an increase or a decrease in the temperature of an emulsion system, required for the desired solidification rate of the components cannot be limited to any specific range, but naturally depends on the emulsion system, i.a. on the used compounds and the concentrations/ratios thereof, as well as on the used solvents, and is chosen accordingly. It is also evident that any techniques may be used to provide sufficient heating or cooling effect to the dispersed system to cause the desired solidification.

In one embodiment the heating or cooling effect is obtained by bringing the emulsion system with a certain temperature to an inert receiving medium with significantly different temperature, e.g. as stated above, whereby said temperature change of the emulsion system is sufficient to cause the rapid solidification of the droplets. The receiving medium can be gaseous, e.g. air, or a liquid, preferably a solvent, or a mixture of two or more solvents, wherein the catalyst component (s) is (are) immiscible and which is inert in relation to the catalyst component (s). For instance, the receiving medium comprises the same immiscible solvent used as the continuous phase in the first emulsion formation step.

Said solvents can be used alone or as a mixture with other solvents, such as aliphatic or aromatic hydrocarbons, such as alkanes. Preferably a fluorinated solvent as the receiving medium is used, which may be the same as the continuous phase in the emulsion formation, e.g. perfluorinated hydrocarbon.

Alternatively, the temperature difference may be effected by gradual heating of the emulsion system, e.g. up to 10° C. per minute, preferably 0.5 to 6° C. per minute and more preferably in 1 to 5° C. per minute.

In case a melt of e.g. a hydrocarbon solvent is used for forming the dispersed phase, the solidifcation of the droplets may be effected by cooling the system using the temperature difference stated above.

Preferably, the "one phase" change as usable for forming an emulsion can also be utilised for solidifying the catalytically active contents within the droplets of an emulsion system by, again, effecting a temperature change in the dispersed system, whereby the solvent used in the droplets becomes miscible with the continuous phase, preferably a fluorous continuous phase as defined above, so that the droplets become impoverished of the solvent and the solidifying components remaining in the "droplets" start to solidify. Thus the immisciblity can be adjusted with respect to the solvents and conditions (temperature) to control the solidification step.

The miscibility of e.g. organic solvents with fluorous solvents can be found from the literature and be chosen accordingly by a skilled person. Also the critical temperatures needed for the phase change are available from the literature or can be determined using methods known in the art, e.g. the Hildebrand-Scatchard-Theorie. Reference is also made to the articles of A. Enders and G. and of Pierandrea Lo Nostro cited above.

Thus according to the invention, the entire or only part of the droplet may be converted to a solid form. The size of the "solidified" droplet may be smaller or greater than that of the original droplet, e.g. if the amount of the monomer used for the prepolymerisation is relatively large.

The solid catalyst particles recovered can be used, after an optional washing step, in a polymerisation process of an olefin. Alternatively, the separated and optionally washed solid particles can be dried to remove any solvent present in the particles before use in the polymerisation step. The separation and optional washing steps can be effected in a known manner, e.g. by filtration and subsequent washing of the solids with a suitable solvent.

The droplet shape of the particles may be substantially maintained. The formed particles may have an average size range of 1 to 500 μm, e.g. 5 to 500 μm, advantageously 5 to 200 μm or 10 to 150 μm. Even an average size range of 5 to 60 μm is possible. The size may be chosen depending on the polymerisation the catalyst is used for. Advantageously, the particles are essentially spherical in shape, they have a low porosity and a low surface area.

The formation of solution can be effected at a temperature of 0-100° C., e.g. at 20-80° C. The dispersion step may be effected at −20° C.-100° C., e.g. at about −10-70° C., such as at −5 to 30° C., e.g. around 0° C.

To the obtained dispersion an emulsifying agent as defined above, may be added to improve/stabilise the droplet formation. The solidification of the catalyst component in the droplets is preferably effected by raising the temperature of the mixture, e.g. from 0° C. temperature up to 100° C., e.g. up to 60-90° C., gradually. E.g. in 1 to 180 minutes, e.g. 1-90 or 5-30 minutes, or as a rapid heat change. Heating time is dependent on the size of the reactor.

During the solidification step, which is preferably carried out at about 60 to 100° C., preferably at about 75 to 95° C., (below the boiling point of the solvents) the solvents may preferably be removed and optionally the solids are washed with a wash solution, which can be any solvent or mixture of solvents such as those defined above and/or used in the art, preferably a hydrocarbon, such as pentane, hexane or heptane, suitably heptane. The washed catalyst can be dried or it can be slurried into an oil and used as a catalyst-oil slurry in polymerisation process.

All or part of the preparation steps can be done in a continuous manner. Reference is made to WO2006/069733 describing principles of such a continuous or semicontinuous preparation methods of the solid catalyst types, prepared via emulsion/solidification method.

Polymerisation

The olefin polymerized using the catalyst of the invention is preferably propylene or a higher alpha-olefin. It may also be ethylene or a mixture of ethylene and an α-olefin. Alternatively, it may also be mixture of alpha olefins, for example $C_{2-20}$ olefins, e.g. ethylene, propylene, 1-butene, 1-hexene, 4-methyl-1-pentene, 1-octene etc. The olefins polymerized in the method of the invention may include any compound which includes unsaturated polymerizable groups. Thus for example unsaturated compounds, such as $C_{6-20}$ olefins (including cyclic and polycyclic olefins (e.g. norbornene)), and polyenes, especially $C_{4-20}$ dienes, may be included in a comonomer mixture with lower olefins, e.g. $C_{2-5}$ α-olefins. Diolefins (i.e. dienes) are suitably used for introducing long chain branching into the resultant polymer. Examples of such dienes include α,ω linear dienes such as 1,5-hexadiene, 1,6-heptadiene, 1,8-nonadiene, 1,9-decadiene, etc.

The catalysts of the present invention are particularly suited for use in the manufacture of polypropylene polymers, either copolymers or homopolymers thereof.

As comonomers to propylene are preferably used ethylene, or higher olefins, e.g. C4-C12 olefins, like 1-butene, 1-hexene, 1-octene or any mixtures thereof, preferably ethylene. It is especially preferred if the copolymer is a propylene ethylene copolymer. That copolymer may be a random copolymer or a heterophasic copolymer. The ethylene content in such a polymer may be up to 50 wt %, e.g. 0.5 to 20 wt %, depending on the desired properties of the polymer. Especially, the catalysts are used to manufacture polypropylene homopolymers, random polypropylene copolymers or heterophasic polypropylene copolymers, preferably with ethylene as comonomer. Heterophasic copolymers may contain a propylene homopolymer or copolymer matrix with an amorphous propylene copolymer component. Such polymers are typically made in a multistep process well known in the art.

Polymerization in the method of the invention may be effected in one or more, e.g. 1, 2 or 3, polymerization reactors, using conventional polymerization techniques, e.g. gas phase, solution phase, slurry or bulk polymerization.

In general, a combination of slurry (or bulk) and at least one gas phase reactor is often preferred, particularly with the reactor order being slurry (or bulk) then one or more gas phase reactors.

In case of propylene polymerisation for slurry reactors, the reaction temperature will generally be in the range 60 to 110° C. (e.g. 60-90° C.), the reactor pressure will generally be in the range 5 to 80 bar (e.g. 20-60 bar), and the residence time will generally be in the range 0.1 to 5 hours (e.g. 0.3 to 2 hours). The monomer is usually used as reaction medium.

For gas phase reactors, the reaction temperature used will generally be in the range 60 to 115° C. (e.g. 70 to 110° C.), the reactor pressure will generally be in the range 10 to 25 bar, and the residence time will generally be 0.5 to 8 hours (e.g. 0.5 to 4 hours). The gas used will be the monomer optionally as mixture with a non-reactive gas such as nitrogen or propane. In addition to actual polymerisation steps and reactors, the process can contain any additional polymerisation steps, like prepolymerisation step, and any further after reactor handling steps as known in the art.

For solution polymerization, an aliphatic or aromatic solvent can be used to dissolve the monomer and the polymer, and the polymerization temperature will generally be in the range 80 to 200° C. (e.g. 90 to 150° C.)

Generally the quantity of catalyst used will depend upon the nature of the catalyst, the reactor types and conditions and the properties desired for the polymer product. As is well known in the art hydrogen can be used for controlling the molecular weight of the polymer.

The metallocene catalysts of certain examples possess excellent catalyst activity and good hydrogen response. The catalysts are also able to provide polymers of high weight average molecular weight Mw.

Moreover, the random copolymerisation behaviour of metallocene catalysts of some examples shows comparable polymerisation activity and decay of activity with increase of ethylene feed as a symmetrical analogue but importantly the weight average molecular weight Mw does not show a negative correlation with increasing ethylene feed as it is witnessed with symmetrical catalysts. This indicates a reduced tendency of chain transfer to ethylene.

Another significant difference is the superior conversion of ethylene with metallocenes of certain examples.

Polymers obtained with the metallocenes of some examples have normal particle morphologies.

Heterophasic copolymers can be prepared with example catalysts and the activity of this catalyst in both liquid and gas phase is much better than that obtained with a standard symmetrical metallocene. The higher activity in bulk and gas phase makes those examples the preferred catalyst over symmetrical ones.

In general therefore example catalysts can provide:
high activity in bulk propylene polymerisation;
very high molecular weight capability (Mw>900 kg/mol);
improved ethylene incorporation in propylene copolymers;
high activity obtained in C2/C3 copolymerization in gas phase;
higher molecular weight of the C2/C3 copolymer produced in gas phase;
good polymer morphology.

It is a feature of certain examples that the claimed catalysts enable the formation of polymers with high molecular weight. These features can be achieved at commercially interesting polymerisation temperatures, e.g. 60° C. or more. It is a preferred feature of some examples that the catalysts are used to polymerise propylene at a temperature of at least 60° C., preferably at least 65° C., such as at least 70° C.

The Mw of the polymers made using the catalysts of the invention may exceed 200,000, preferably at least 250,000, e.g. at least 350,000. Values of more than 500,000 have also been achieved. Mw/Mn values are generally low, e.g. less than 4, such as less than 3.5 or even less than 3.

Polypropylenes made by the metallocenes of the invention can be made with $MFR_{21}$ values in the range of 0.1 to 100 g/10 min depending on the amount of comonomer content and/or use and amount of hydrogen used as MFR regulating agent.

The polymers made by the catalysts of the invention are useful in all kinds of end articles such as pipes, films (cast, blown or BOPP films, such as for example BOPP for capacitor film), fibers, moulded articles (e.g. injection moulded, blow moulded, rotomoulded articles), extrusion coatings and so on.

The invention will now be illustrated by reference to the following non-limiting examples.

Analytical Tests

Measurement Methods:

Al and Zr Determination (ICP-method)

The elementary analysis of a catalyst was performed by taking a solid sample of mass, M, cooling over dry ice. Samples were diluted up to a known volume, V, by dissolving in nitric acid ($HNO_3$, 65%, 5% of V) and freshly deionised (DI) water (5% of V). The solution was then added to hydrofluoric acid (HF, 40%, 3% of V), diluted with DI water up to the final volume, V, and left to stabilise for two hours.

The analysis was run at room temperature using a Thermo Elemental iCAP 6300 Inductively Coupled Plasma—Optical Emmision Spectrometer (ICP-OES) which was calibrated using a blank (a solution of 5% $HNO_3$, 3% HF in DI water), and 6 standards of 0.5 ppm, 1 ppm, 10 ppm, 50 ppm, 100 ppm and 300 ppm of Al, with 0.5 ppm, 1 ppm, 5 ppm, 20 ppm, 50 ppm and 100 ppm of Hf and Zr in solutions of 5% HNO3, 3% HF in DI water.

Immediately before analysis the calibration is 'resloped' using the blank and 100 ppm Al, 50 ppm Hf, Zr standard, a quality control sample (20 ppm Al, 5 ppm Hf, Zr in a solution of 5% HNO3, 3% HF in DI water) is run to confirm the reslope. The QC sample is also run after every 5th sample and at the end of a scheduled analysis set.

The content of hafnium was monitored using the 282.022 nm and 339.980 nm lines and the content for zirconium using 339.198 nm line. The content of aluminium was monitored via the 167.079 nm line, when Al concentration in ICP sample was between 0-10 ppm (calibrated only to 100 ppm) and via the 396.152 nm line for Al concentrations above 10 ppm.

The reported values are an average of three successive aliquots taken from the same sample and are related back to the original catalyst by inputting the original mass of sample and the dilution volume into the software.

DSC Analysis

The melting point ($T_m$) and crystallization temperature ($T_c$) were determined on a DSC200 TA instrument, by placing a 5-7 mg polymer sample, into a closed DSC aluminum pan, heating the sample from −10° C. to 210° C. at 10° C./min, holding for 5 min at 210° C., cooling from 210° C. to −10° C., holding for 5 min at −10° C., heating from −10° C. to 210° C. at 10° C./min. The reported $T_m$ is the maximum of the curve from the second heating scan and $T_c$ is the maximum of the curve of the cooling scan.

Melt Flow Rate

The melt flow rate (MFR) is determined according to ISO 1133 and is indicated in g/10 min. The MFR is an indication of the flowability, and hence the processability, of the polymer. The higher the melt flow rate, the lower the viscosity of the polymer. The MFR is determined at 230° C. and may be determined at different loadings such as 2.16 kg ($MFR_2$) or 21.6 kg ($MFR_{21}$).

Intrinsic viscosity is measured according to DIN ISO 1628/1, October 1999 (in Decalin at 135° C.).

GPC: Molecular weight averages, molecular weight distribution, and polydispersity index ($M_n$, $M_w$, $M_w/M_n$)

Molecular weight averages (Mw, Mn), Molecular weight distribution (MWD) and its broadness, described by polydispersity index, PDI=Mw/Mn (wherein Mn is the number average molecular weight and Mw is the weight average molecular weight) were determined by Gel Permeation Chromatography (GPC) according to ISO 16014-4:2003 and ASTM D 6474-99. A Waters GPCV2000 instrument, equipped with differential refractive index detector and online viscosimeter was used with 2×GMHXL-HT and 1×G7000HXL-HT TSK-gel columns from Tosoh Bioscience and 1,2,4-trichlorobenzene (TCB, stabilized with 250 mg/L 2,6-Di tert butyl-4-methyl-phenol) as solvent at 140° C. and at a constant flow rate of 1 mL/min. 209.5 μL of sample solution were injected per analysis. The column set was calibrated using universal calibration (according to ISO 16014-2:2003) with at least 15 narrow MWD polystyrene (PS) standards in the range of 1 kg/mol to 12 000 kg/mol. Mark Houwink constants for PS, PE and PP used are as per ASTM D 6474-99. All samples were prepared by dissolving 0.5-4.0 mg of polymer in 4 mL (at 140° C.) of stabilized TCB (same as mobile phase) and keeping for max. 3 hours at max. 160° C. with continuous gentle shaking prior sampling into the GPC instrument.

Determination of Xylene Soluble Fraction (XS):

2.0 g of polymer is dissolved in 250 ml p-xylene at 135° C. under agitation. After 30 minutes the solution is allowed to cool for 15 minutes at ambient temperature and then allowed to settle for 30 minutes at 25° C. The solution is filtered with filter paper into two 100 ml flasks.

The solution from the first 100 ml vessel is evaporated in nitrogen flow and the residue is dried under vacuum at 90° C. until constant weight is reached.

XS %=(100·m·Vo)/(mo·v); mo=initial polymer amount (g); m=weight of residue (g); Vo=initial volume (ml); v=volume of analysed sample (ml).

Ethylene Content (FTIR $C_2$)

Ethylene content was measured with Fourier transform infrared spectroscopy (FTIR) calibrated to results obtained by $^{13}C$ NMR spectroscopy using a method which accounts for regio-irregular propene insertion. When measuring the ethylene content in polypropylene, a thin film of the sample (thickness about 0.220 to 0.250 mm) was prepared by hotpressing at 230° C. (preheat 5 min., press 1 min., cooling (cold water) 5 min.) using a Graseby Specac press. The FTIR spectra of the sample was recorded immediately with Nicolet Protégé 460 spectrometer from 4000 to 400 $cm^{-1}$, resolution 4 $cm^{-1}$, scans 64. The area of absorption peak at 733 $cm^{-1}$ (baseline from 700 $cm^{-1}$ to 760 $cm^{-1}$) and height of reference peak at 809 $cm^{-1}$ (baseline from 780 $cm^{-1}$ to 880 $cm^{-1}$) were evaluated. The result was calculated using the following formula $$E_{tot}=a \times A/R+b$$

where

A=area of absorption peak at 733 $cm^{-1}$

R=height of reference peak at 809 $cm^{-1}$ $E_{tot}$=C2 content (wt.-%)

a, b are calibration constants determined by correlation of multiple calibration standards of know ethylene content as determined by $^{13}C$ NMR spectroscopy to A/R.

The result was reported as an average of two measurements.

DMTA

The dynamic-mechanical analysis (DMTA) data are obtained according to ISO 6721-1 (General principles) & 6721-7 (Torsional vibration—Non-resonance method)

Experimental Setup:

A Rheometric scientific ARES rheometer, equipped with a liquid nitrogen unit and an oven (convection and radiation heating), a standard torsion rectangular tool and a software orchestrator V6.5.8, or Anton Paar MCR301 rheometer with a TC30 temperature control unit combined with a liquid nitrogen unit and an CTD600 oven (convection and radiation heating) a standard torsion rectangular tool and a software RHEOPLUS/32 v3.40 are used.

Sample Preparation

Stabilized dry pellets are compression molded at 210° C. (gel time 5 min, pressure time 25 bar/3 min, cooling rate 25 bar/15K/min, de-molding temperature 40° C.) in a 100*100*1 mm mould. Only from homogeneous, bubble free plates are punched to 50×10×1 mm stripes and are conditioned at least 96 hours at room temperature.

Conducting the Experiment:

The device is cooled with the clamped sample to the initial temperature (standard −130° C.). After 5 min delay time the experiment is started with a test frequency of 1 Hz, a heating rate of 2K/min and a strain $\epsilon$ of 0.1%.

The measurements are carried out under inert atmosphere (nitrogen) and a tension (vertically) force of 50 g(+/−20 g).

Temperature dependence of storage modulus G', loss modulus G", and loss angle tangent tan($\delta$) are used for evaluations.

Determinations of transition sections (e.g. glass transition temperature, $T_g$) is based on the loss tangent tan($\delta$) vs. temperature curve (peak of the curve). Number of specimen: 1. Precision: +/−5%, temperature values: +/−1.5K

EXAMPLES

Chemicals

All the chemicals and chemical reactions were handled under an inert gas atmosphere using Schlenk and glovebox techniques, with oven-dried glassware, syringes, needles or cannulas.

MAO was purchased from Albermarle and used as a 30 wt-% solution in toluene. Perfluoroalkylethyl acrylate ester mixture (CAS number 65605-70-1) was purchased from the Cytonix corporation, dried over activated molecular sieves (2 times) and degassed by argon bubbling prior to use. Hexadecafluoro-1,3-dimethylcyclohexane (CAS number 335-27-3) was obtained from commercial sources and dried over activated molecular sieves (2 times) and degassed by argon bubbling prior to use. Triethylaluminum was purchased from Crompton and used in pure form. Hydrogen is provided by AGA and purified before use. Propylene is provided by Borealis and adequately purified before use.

1-tert-Butyl-2-methoxybenzene was synthesized via alkylation of 2-tert-butylphenol (Acros) by dimethylsulfate (Merck) in the presence of aqueous NaOH (Reachim, Russia) as described in [Stork, G.; White, W. N. *J. Am. Chem. Soc.* 1956, 78, 4604.]. 2-Methyl-4-bromo-6-tert-butylindanone-1 was obtained as described in the literature [Resconi, L.; Nifant'ev, I. E.; Ivchenko, P. V.; Bagrov, V.; Focante, F.; Moscardi, G. Int. Pat. Appl. WO2007/107448 Al].

7-Bromo-5-tert-butyl-2-methyl-1H-indene was obtained from 2-methyl-4-bromo-6-tert-butylindanone-1 as described in [Voskoboynikov, A. Z.; Asachenko, A. F.; Kononovich, D. S.; Nikulin M. V.; Tsarev, A. A.; Maaranen, J.; Vanne, T.; Kauhanen, J.; Mansner, E.; Kokko, E.; Saarinen, L. Int. Pat. Appl. WO2009/027075].

Bis(2,6-diisopropylphenyl)imidazolium chloride, i.e. IPr (HCl), and (IPr)NiCl$_2$(PPh$_3$) were synthesized as described in [Hintermann, L. *Beilstein J. Org. Chem.* 2007, 3, 1.] and [Matsubara, K.; Ueno, K.; Shibata, Y. *Organometallics* 2006, 25, 3422.], respectively.

4/7-Bromo-2-methyl-3/1H-indene was obtained as described in [Izmer, V. V.; Lebedev, A. Y.; Nikulin, M. V.; Ryabov, A. N.; Asachenko, A. F.; Lygin, A. V.; Sorokin, D. F.; Voskoboynikov, A. Z. *Organometallics* 2006, 25, 1217.].

Anisole (Acros), 3-methylanisole (Acros), tert-Butyltoluene (Aldrich), 1-Bromo-4-tert-butylbenzene (Acros), P$_4$O$_{10}$ (Reachim), Pd(P$^t$Bu$_3$)$_2$ (Strem), 1.0 M ZnCl$_2$ in THF (Aldrich), 1.0 M 3,5-di-tert-butylphenylmagnesium bromide in THF (Aldrich), hexanes (Reachim, Russia), N-bromosuccinimide (Acros), diethyl methylmalonate (Aldrich), methyl iodide (Acros), acetone (Reachim, Russia), tetraethylammonium iodide (Acros), triphenylphosphine (Acros), CuCN (Merck), methanesulfonic acid (Aldrich), sodium tetraphenylborate (Aldrich), palladium acetate (Aldrich), copper cyanide (Merck), magnesium turnings (Acros), lithium aluminiumhydride (Aldrich), bromobenzene (Acros), 2.5 M $^n$BuLi in hexanes (Chemetall), ZrCl$_4$(THF)$_2$ (Aldrich), NaBH$_4$ (Aldrich), Ni(OAc)$_2$ (Aldrich), silica gel 60 (40-63 um, Merck), AlCl$_3$ (Merck), bromine (Merck), benzoyl peroxide (Aldrich), iodine (Merck), NaHCO$_3$ (Merck), Na$_2$CO$_3$ (Merck), K$_2$CO$_3$ (Merck), Na$_2$SO$_4$ (Merck), Na$_2$SO$_3$ (Merck), sodium metal (Merck), thionyl chloride (Merck), sodium acetate, trihydrate (Merck), tetraethylammonium iodide (Acros), triphenylphosphine (Acros), KOH (Merck), Na$_2$SO$_4$ (Akzo Nobel), TsOH (Aldrich), 12 M HCl (Reachim, Russia), methanol (Merck), anhydrous ethanol (Merck), CDCl$_3$ and DMSO-d$_6$ (Deutero GmbH) as well as hexanes (Merck), carbon tetrachloride (Merck), ether (Merck), ethyl acetate (Merck), toluene (Merck) and CH$_2$Cl$_2$ (Merck) for extractions were used as received.

Tetrahydrofurane (Merck), ether (Merck), and dimethoxyethane (Acros) freshly distilled from benzophenone ketyl were used. Dichloromethane (Merck) for organometallic synthesis as well as CD$_2$Cl$_2$ (Deutero GmbH) for NMR experiments were dried and kept over CaH$_2$. Toluene (Merck), n-octane (Merck), and hexanes (Merck) for organometallic synthesis were kept and distilled over Na/K alloy. Dichlorodimethylsilane (Merck) and methacrylic acid (Acros) were distilled before use.

Rac-methyl(cyclohexyl)silanediylbis[2-methyl-4-(4-tert-butylphenyl)indenyl]zirconium dichloride (C1):

was purchased from a commercial source.

Rac-dimethylsilanediylbis(2-methyl-4-phenyl-5-methoxy-6-tert-butylindenyl) zirconium dichloride (C2):

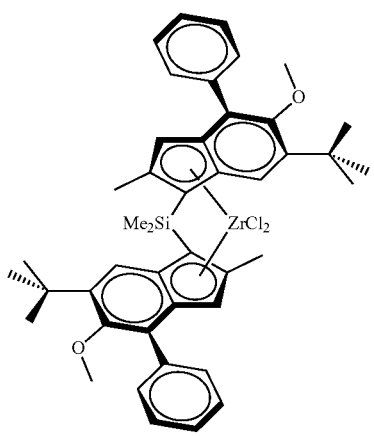

was synthesized as described in WO 2007/116034.
Preparation of Example Metallocene Complexes Synthesis of anti-Dimethylsilylene(2-methyl-4-phenyl-5-methoxy-6-tert-butyl-indenyl)(2-methyl-4-phenyl-6-tert-butyl-indenyl)zirconium dichloride (Metallocene E1)

6-tert-Butyl-5-methoxy-2-methylindan-1-one

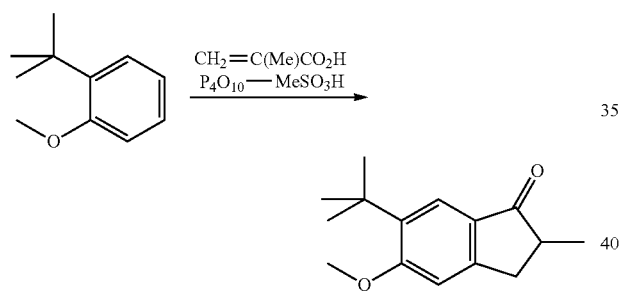

To an Eaton's reagent obtained from 110 g of $P_4O_{10}$ and 560 ml of methanesulfonic acid a mixture of 65.6 g (0.399 mol) of 1-tert-butyl-2-methoxybenzene and 43.0 g (0.50 mol) of methacrylic acid was added for ca. 1 h at 50-55° C. The resulting mixture was stirred for 1 h at this temperature, then cooled to room temperature, and poured on a mixture of 1 liter of cold water and 1 kg of ice. The crude product was extracted with 3×500 ml of dichloromethane. The combined organic extract was washed by aqueous $K_2CO_3$ and then evaporated to dryness. Fractional rectification of the residue gave 64.9 g of yellowish oil which crystallizes at room temperature. On the evidence of NMR spectroscopy, this product includes ca. 90% of the target material. Further on, this product was dissolved in 180 ml of hot hexanes. Crystals precipitated from this solution at room temperature were collected, washed by 100 ml of cold hexanes, and dried in vacuum. This procedure gave 39.6 g (43%) of the analytically pure substituted indanone.

Anal. calc. for $C_{15}H_{20}O_2$: C, 77.55; H, 8.68. Found: C, 77.48; H, 8.79.

$^1$H NMR (CDCl$_3$): δ 7.68 (s, 1H, 7-H in indanone), 6.87 (s, 1H, 4-H in indanone), 3.93 (s, 3H, OMe), 3.32 (m, 1H, 3-H in indanone), 2.69 (m, 1H, 2-H in indanone), 2.64 (m, 1H, 3'-H in indanone), 1.37 (s, 9H, tu), 1.29 (d, J=7.3 Hz, 3H, 2-Me in indanone). $^{13}$C{$^1$H} NMR (CDCl$_3$): δ 208.1, 164.6, 154.4, 138.8, 128.7, 122.1, 107.8, 55.2, 42.1, 35.0, 34.7, 29.6, 16.6.

6-tert-Butyl-5-methoxy-2-methylindan-1-one
(Second Experiment)

To Eaton's reagent obtained from 118 g of $P_4O_{10}$ and 600 ml of methanesulfonic acid a mixture of 70.3 g (0.428 mol) of 1-tert-butyl-2-methoxybenzene and 295.0 g (3.43 mol, 8 eqv.) of methacrylic acid was added for ca. 1 h at 50-55° C. The resulting mixture was stirred for 0.5 h at this temperature, then cooled to room temperature, and poured on a mixture of 1.5 liter of cold water and 2 kg of ice. After the ice melts, the precipitated crude 6-tert-butyl-5-methoxy-2-methylindan-1-one was filtered off and then washed with 2×100 ml of cold water. The crude product was dissolved in 500 ml of dichloromethane, and this solution was washed by aqueous $K_2CO_3$, dried over anhydrous $K_2CO_3$, and then evaporated on Rotavap. The residue was distilled in vacuum to give 70.6 g of crude 6-tert-butyl-5-methoxy-2-methylindan-1-one, b.p. 155-165° C./5 mm Hg. This product was dissolved in 200 ml of hot hexanes. Crystals precipitated from this solution at 5° C. were collected, washed by 50 ml of cold hexanes, and dried in vacuum. This procedure gave 64.1 g (65%) of the analytically pure substituted indanone.

4-Bromo-6-tert-butyl-5-methoxy-2-methylindan-1-one

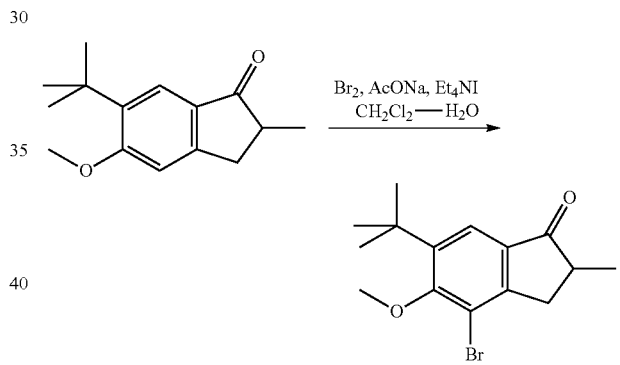

To a mixture of 60.0 g (0.258 mol) of 6-tert-butyl-5-methoxy-2-methylindan-1-one, 130 g of NaOAc(H$_2$O)$_3$, 1.5 g of Et$_4$NI, 220 ml of dichloromethane, and 450 ml of water cooled to 5° C. 45.0 g (0.282 mol) of bromine was added for ca. 5 min by vigorous stirring. This mixture was stirred for 1 h at 5° C., and then a solution of 60.0 g of NaOAc(H$_2$O)$_3$ in 200 ml of water was added. To the resulting mixture 23.5 (0.147 mmol) of bromine was added at 5° C. The resulting solution was stirred for 30 min and then Na$_2$SO$_3$ was added by small portions to remove an excess of bromine. The CH$_2$Cl$_2$-layer was separated from the top aqueous one and the latter was extracted with 2×300 ml of dichloromethane. The combined organic extract was dried over K$_2$CO$_3$, passed through a short layer of silica gel 60 (40-63 um) and then evaporated to dryness. The residue was dried in vacuum to give 79.9 g (99%) of the title compound which was further used without an additional purification.

Anal. calc. for $C_{15}H_{19}BrO_2$: C, 57.89; H, 6.15. Found: C, 57.70; H, 6.08.

$^1$H NMR (CDCl$_3$): δ 7.70 (s, 1H, 7-H in indanone), 4.03 (s, 3H, OMe), 3.31 (dd, J=17.4 Hz, J=7.8 Hz, 1H, 3-H in indanone), 2.72 (m, 1H, 2-H in indanone), 2.62 (dd, J=17.4 Hz, J=3.8 Hz, 1H, 3'-H in indanone), 1.40 (s, 9H, $^t$Bu), 1.32

(d, J=7.6 Hz, 3H, 2-Me in indanone). $^{13}$C{$^1$H} NMR (CDCl$_3$): δ 208.0, 162.8, 154.0, 145.5, 132.7, 121.5, 116.7, 61.7, 42.2, 36.1, 35.7, 30.6, 16.4.

6-tert-Butyl-5-methoxy-2-methyl-4-phenylindan-1-one

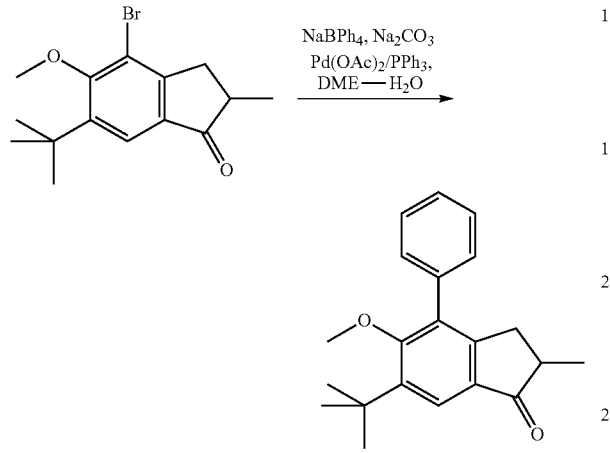

To a mixture of 46.7 g (0.150 mol) of 4-bromo-6-tert-butyl-5-methoxy-2-methylindan-1-one, 44.0 g (0.415 mol) of Na$_2$CO$_3$, 25.7 g (0.075 mol) of NaBPh$_4$, 600 ml of DME, and 240 ml of water 1.01 g (4.50 mmol) of Pd(OAc)$_2$ and 2.36 g (9.00 mmol) of PPh$_3$ were added. The resulting mixture was refluxed for 12 h, cooled to room temperature, and then evaporated to dryness. To the residue 1 liter of cold water was added, and the crude product was extracted with 3×300 ml of dichloromethane. The combined organic extract was dried over K$_2$CO$_3$ and then evaporated to dryness. The product was isolated by flash chromatography on silica gel 60 (40-63 um; eluent: hexanes-dichloromethane-ether=20:10:1, vol.). Yield 46.0 g (99%) of yellowish crystalline solid.

Anal. calc. for C$_{21}$H$_{24}$O$_2$: C, 81.78; H, 7.84. Found: C, 81.90; H, 7.93.

$^1$H NMR (CDCl$_3$): δ 7.76 (s, 1H, 7-H in indanone), 7.47 (m, 2H, 3,5-H in Ph), 7.42 (m, 2H, 2,6-H in Ph), 7.39 (m, 1H, 4-H in Ph), 3.29 (s, 3H, OMe), 3.13 (dd, J=17.4 Hz, J=7.8 Hz, 1H, 3-H in indanone), 2.63 (m, 1H, 2-H in indanone), 2.47 (dd, J=17.4 Hz, J=3.8 Hz, 1H, 3'-H in indanone), 1.43 (s, 9H, $^t$Bu), 1.25 (d, J=7.3 Hz, 3H, 2-Me in indanone). $^{13}$C{$^1$H} NMR (CDCl$_3$): δ 208.7, 163.5, 152.7, 143.5, 136.4, 132.5, 131.0, 129.5, 128.7, 127.5, 121.6, 60.5, 42.2, 35.4, 34.3, 30.5, 16.4.

6-tert-Butyl-5-methoxy-2-methyl-4-phenylindan-1-one (Second Experiment)

To a mixture of 46.7 g (0.150 mol) of 4-bromo-6-tert-butyl-5-methoxy-2-methylindan-1-one, 44.5 g (0.420 mol) of Na$_2$CO$_3$, 22.0 g (0.180 mol) of PhB(OH)$_2$, 570 ml of DME, and 195 ml of water 0.674 g (3.0 mmol) of Pd(OAc)$_2$ and 1.58 g (6.00 mmol) of PPh$_3$ were added. The resulting mixture was refluxed for 12 h, cooled to room temperature, and then DME was evaporated on Rotavap. To the residue 1 liter of cold water was added, and the crude product was extracted with 3×300 ml of dichloromethane. The combined organic extract was dried over K$_2$CO$_3$ and then evaporated to dryness. The residue after evaporation was extracted with hot hexane (500 ml, then 3×250 ml) and this extracts while hot were passed through a short pad of silicagel, evaporated on Rotavap to yield 45.1 g (98%) of 6-tert-butyl-5-methoxy-2-methyl-4-phenylindan-1-one as a slightly yellowish crystalline solid which was further used without an additional purification.

5-tert-Butyl-6-methoxy-2-methyl-7-phenyl-1H-indene

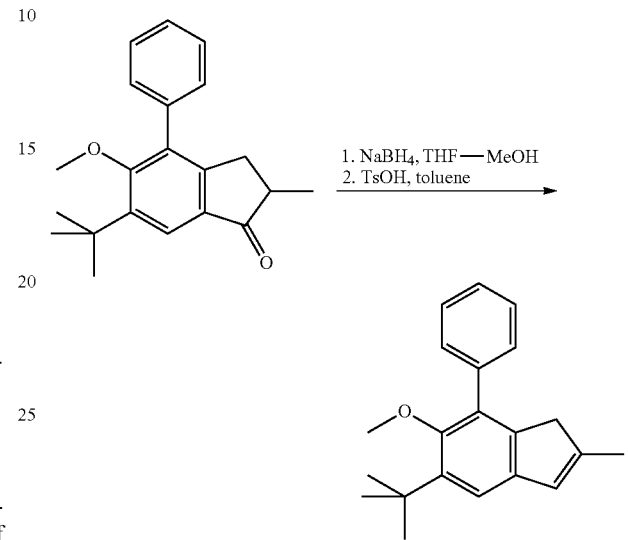

To a solution of 45.9 g (0.149 mmol) of 6-tert-butyl-5-methoxy-2-methyl-4-phenylindan-1-one in 300 ml of THF cooled to 5° C. 8.51 g (0.225 mol) of NaBH$_4$ was added. Further on, 150 ml of methanol was added dropwise to this mixture by vigorous stirring for ca. 7 h at 5° C. The resulting mixture was stirred overnight at room temperature, and then 1 liter of cold water and 12 M HCl to pH~1 were added. The crude product was extracted with 3×200 ml of dichloromethane, the combined organic extract was dried over K$_2$CO$_3$ and then evaporated to dryness. To a solution of the residue in 800 ml of toluene 1.0 g of TsOH was added, this mixture was refluxed with Dean-Stark head for 10 min and then cooled to room temperature using water bath. The resulting solution was washed by 10% aqueous Na$_2$CO$_3$, the organic layer was separated, the aqueous layer was extracted with 2×50 ml of dichloromethane. The combined organic solution was dried over K$_2$CO$_3$ and then passed through short layer of silica gel 60 (40-63 um). The silica gel layer was additionally washed by 100 ml of dichloromethane. The combined organic elute was evaporated to dryness. This procedure gave 43.1 g (99%) of yellowish oil which was further used without an additional purification.

Anal. calc. for C$_{21}$H$_{24}$O: C, 86.26; H, 8.27. Found: C, 86.39; H, 8.37.

$^1$H NMR (CDCl$_3$): δ 7.47-7.49 (m, 2H, 2,6-H in Ph), 7.43 (m, 2H, 3,5-H in Ph), 7.34 (m, 1H, 4-H in Ph), 7.22 (s, 1H, 4-H in indene), 6.44 (m, 1H, 3-H in indene), 3.22 (s, 3H, OMe), 3.12 (s, 2H, 1,1'-H in indene), 2.06 (s, 3H, 2-Me in indene), 1.44 (s, 9H, $^t$Bu). $^{13}$C{$^1$H} NMR (CDCl$_3$): δ 154.3, 145.3, 141.7, 141.0, 138.5, 131.6, 129.5, 128.3, 126.9, 126.8, 117.2, 60.7, 42.8, 35.2, 31.0, 16.6.

5-tert-Butyl-6-methoxy-2-methyl-7-phenyl-1H-indene (Second Experiment)

To a solution of 44.3 g (0.144 mmol) of 6-tert-butyl-5-methoxy-2-methyl-4-phenylindan-1-one in 150 ml of THF cooled to 5° C. 2.72 g (71.9 mmol) of NaBH₄ was added. Further on, 75 ml of methanol was added dropwise to this mixture by vigorous stirring for 1 h at 5° C. The resulting mixture was stirred additionally 1 h at 5° C., then 0.5 h at room temperature, and then added to 1 liter of cold water and 30 ml of 12 M HCl in separating funnel. The crude product was extracted consequentially with 250, 100 and 50 ml of dichloromethane, and the combined organic extract was evaporated to dryness. To a solution of the residue in 500 ml of toluene 1.0 g of TsOH was added, this mixture was refluxed with Dean-Stark head for 10 min and then cooled to room temperature using water bath. The resulting solution was washed by aqueous $K_2CO_3$ (20 g $K_2CO_3$ in 200 ml of $H_2O$), the organic layer was separated, the aqueous layer was extracted with 2×50 ml of dichloromethane. The combined organic solution was dried over $K_2CO_3$ and then passed through short layer of silica gel 60 (40-63 um, ca. 10 g). The silica gel layer was additionally washed by 50 ml of dichloromethane. The combined organic elute was evaporated to dryness. This procedure gave 42.0 g (~100%) of yellowish oil which was further used without an additional purification.

(6-tert-Butyl-5-methoxy-2-methyl-4-phenyl-1H-inden-1-yl)(chloro)dimethylsilane

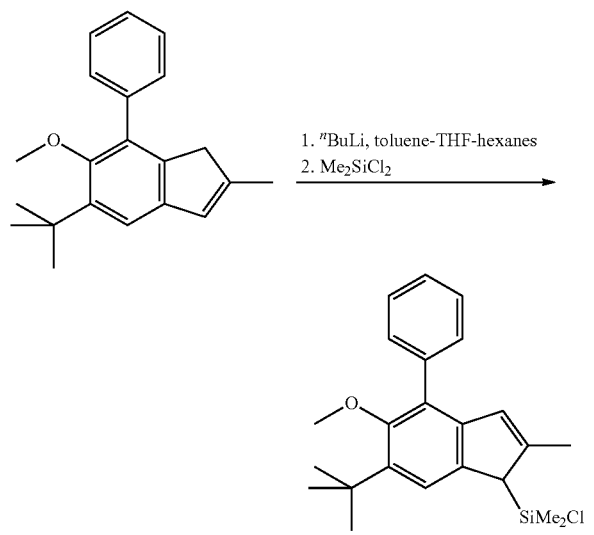

To a solution of 16.2 g (55.4 mmol) of 5-tert-butyl-6-methoxy-2-methyl-7-phenyl-1H-indene in 300 ml of toluene, 22.2 ml (55.5 mmol) of 2.5 M ⁿBuLi in hexanes was added at room temperature. The resulting viscous solution was stirred for 2 h, and then 15 ml of THF was added. The formed suspension was stirred for 12 h at room temperature, ca. 2 h at 60° C., then cooled to −20° C., and 35.8 g (277 mmol) of dichlorodimethylsilane was added in one portion. The resulting solution was warmed to 60° C. and stirred for 1 h at this temperature. The resulting mixture was evaporated to ca. ½ of its volume, then filtered through glass frit (G3). The precipitate was additionally washed by 20 ml of toluene. The combined filtrate was evaporated to dryness to give 21.2 g (99%) of viscous yellowish oil.

Anal. calc. for $C_{23}H_{29}ClOSi$: C, 71.75; H, 7.59. Found: C, 71.92; H, 7.80.

¹H NMR (CDCl₃): δ 7.52-7.54 (m, 2H, 2,6-H in Ph), 7.48 (m, 2H, 3,5-H in Ph), 7.45 (s, 1H, 7-H in indenyl), 7.38 (m, 1H, 4-H in Ph), 6.49 (m, 1H, 3-H in indenyl), 3.59 (m, 1H, 1-H in indenyl), 3.27 (s, 3H, OMe), 2.23 (m, 3H, 2-Me in indenyl), 1.48 (s, 9H, ᵗBu), 0.47 (s, 3H, SiMeMe'), 0.22 (s, 3H, SiMeMe'). ¹³C {¹H} NMR (CDCl₃): δ 155.8, 146.2, 143.7, 138.2, 137.6, 137.0, 130.2, 128.3, 127.4, 126.7, 126.5, 121.1, 60.5, 50.1, 35.2, 31.2, 17.6, 1.1, −0.6.

5-tert-Butyl-2-methyl-7-phenyl-1H-indene

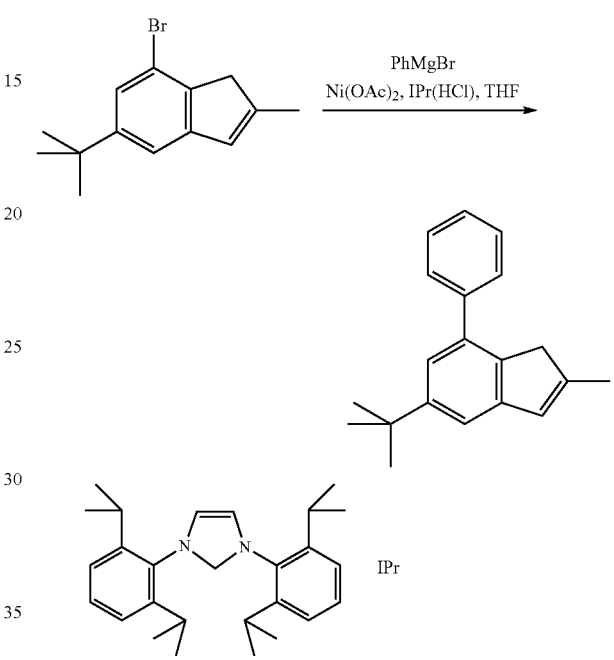

To a solution of PhMgBr obtained from 89.0 g (567 mmol) of bromobenzene, 15.8 g (650 mmol) of magnesium turnings and 450 ml of THF, 1.60 g (3.76 mmol) of bis(2,6-diisopropylphenyl)imidazolium chloride, i.e. IPr(HCl) and 0.66 g (3.76 mmol) of Ni(OAc)₂ were added. Further on, a solution of 50.0 g (189 mmol) of 7-bromo-5-tert-butyl-2-methyl-1H-indene in 50 ml of THF was added. The resulting mixture was stirred for 2 h at room temperature, refluxed for 1 h, cooled to ambient temperature, and then 200 ml of water was added dropwise. Finally, 100 ml of 12 M HCl was added dropwise. The product was extracted with 300 ml of ether. The organic layer was separated, and the aqueous layer was additionally extracted with 2×150 ml of dichloromethane. The combined organic extract was dried over $K_2CO_3$, passed through a short layer of silica gel 60 (40-63 um), and then evaporated to dryness. Fractional rectification of the residue gave 34.7 g (70%) of viscous yellow oil, b.p. 180-210° C./5 mm Hg. The product is a ca. 1 to 1 mixture of 6-tert-butyl-2-methyl-4-phenyl-1H-indene and 5-tert-butyl-2-methyl-7-phenyl-1H-indene.

Anal. calc. for $C_{20}H_{22}$: C, 91.55; H, 8.45. Found: C, 91.61; H, 8.50.

¹H NMR (CDCl₃): δ 7.52 (m, 4H), 7.40-7.43 (m, 6H), 7.29-7.33 (m, 3H), 7.17 (m, 1H), 6.62 (m, 1H), 6.50 (m, 1H), 3.32 (s, 4H), 2.10 (s, 6H), 1.37 (s, 9H), 1.36 (s, 9H).

39
(6-tert-Butyl-5-methoxy-2-methyl-4-phenyl-1H-inden-1-yl)-(6-tert-butyl-2-methyl-4-phenyl-1H-inden-1-yl)dimethylsilane

40
Anti-Dimethylsilylene(2-methyl-4-phenyl-5-methoxy-6-tert-butyl-indenyl)(2-methyl-4-phenyl-6-tert-butyl-indenyl)zirconium dichloride (Metallocene E1)

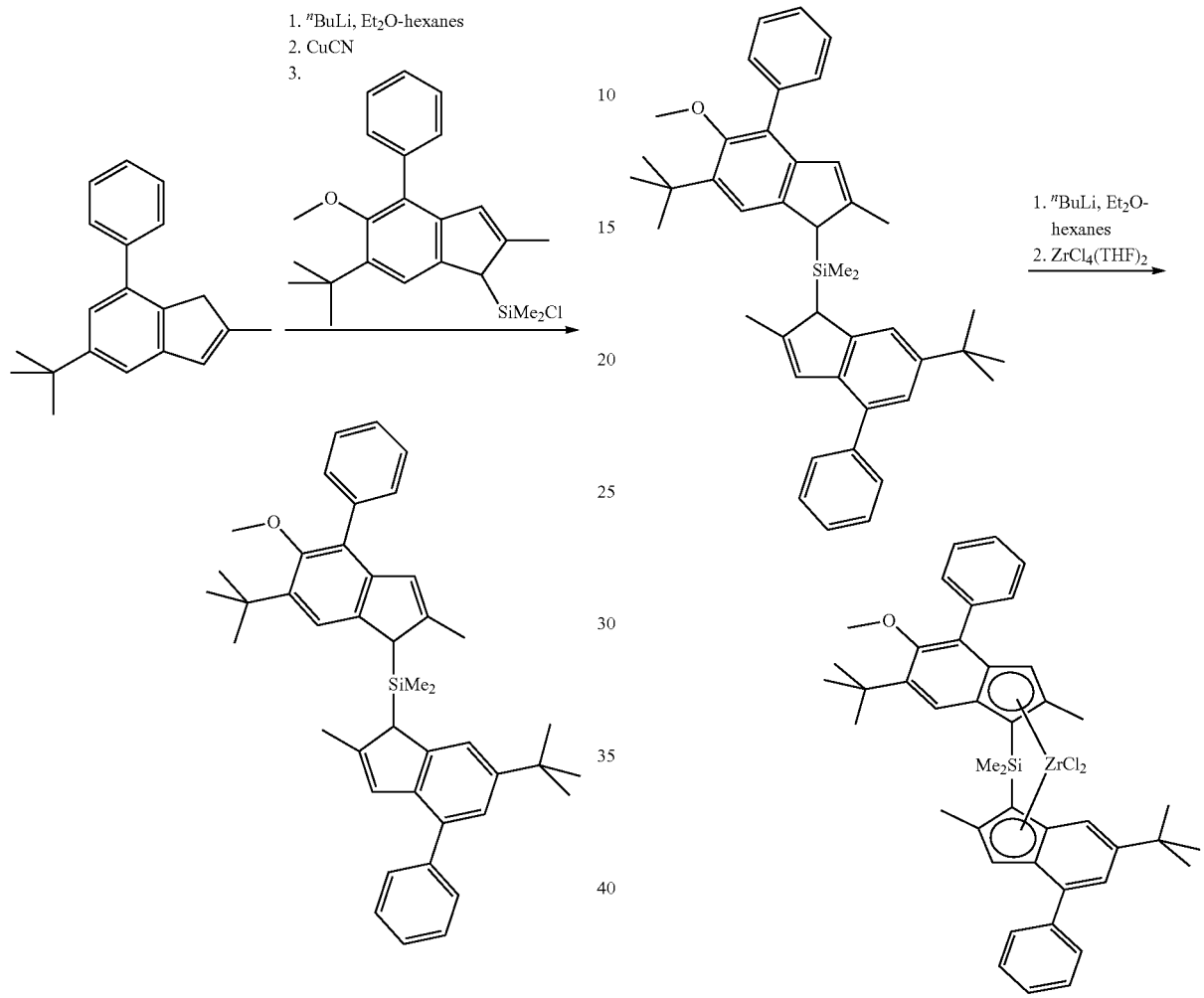

To a solution of 14.5 g (55.4 mmol) of 5-tert-butyl-2-methyl-7-phenyl-1H-indene in 400 ml of ether cooled to −78° C., 22.2 ml (55.5 mmol) of 2.5 M $^n$BuLi in hexanes was added. This mixture was stirred overnight at room temperature, then cooled to −78° C., and 200 mg (2.23 mmol) of CuCN was added. The resulting mixture was stirred for 30 min at −20° C., then cooled to −78° C., and a solution of 21.2 g (55.4 mmol) of (6-tert-butyl-5-methoxy-2-methyl-4-phenyl-1H-inden-1-yl)(chloro)dimethylsilane in 200 ml of ether was added. This mixture was stirred overnight at room temperature, then 1 ml of water was added. The obtained mixture was passed through a short layer of silica gel 60 (40-63 um), the elute was evaporated to dryness. The product was isolated by flash-chromatography on silica gel 60 (40-63 um; eluent: hexanes-dichloromethane=10:1, vol., then 3:1, vol.). This procedure gave 24.5 g (72%) of yellowish glassy solid.

Anal. calc. for $C_{43}H_{50}OSi$: C, 84.54; H, 8.25. Found: C, 84.69; H, 8.34.

$^1$H NMR (CDCl$_3$): δ 7.35-7.62 (m), 6.81 (s), 6.75 (s), 6.63 (s), 6.45 (s), 3.73 (s), 3.71 (s), 3.70 (s), 3.30 (s), 2.23 (s), 2.22 (s), 2.15 (s), 2.08 (s), 1.50 (s), 1.49 (s), 1.43 (s), 1.42 (s), 0.06 (s), −0.06 (s), −0.07 (s), −0.08 (s), −0.12 (s).

To a solution of 7.64 g (12.5 mmol) of (6-tert-butyl-5-methoxy-2-methyl-4-phenyl-1H-inden-1-yl)(6-tert-butyl-2-methyl-4-phenyl-1H-inden-1-yl)dimethylsilane in 200 ml of ether cooled to −78° C., 10.0 ml (25.0 mmol) of 2.5 M $^n$BuLi in hexanes was added. The resulting mixture was stirred overnight at room temperature, then cooled to −78° C., and 4.72 g (12.5 mmol) of ZrCl$_4$(THF)$_2$ was added. This mixture was stirred for 24 h at room temperature. On the evidence of NMR spectroscopy, this mixture included anti and syn zirconocenes in ratio equal to ca. 70:30. This mixture was filtered through glass frit (G4), the filtrate was evaporated to dryness. The residue was dissolved in a mixture of 60 ml of n-octane and 15 ml of toluene at reflux. Crystals precipitated from this solution at −30° C. were collected, washed by 2×10 ml of cold hexanes, and dried in vacuum. This procedure gave 1.97 g (20%) of pure racemic-anti zirconocene. Additional amount of this product was obtained in similar manner from the mother liquid. Thus, the combined yield of the product was 3.54 g (37%) as yellowish-orange crystalline solid.

Anal. calc. for $C_{43}H_{48}Cl_2OSiZr$: C, 66.98; H, 6.27. Found: C, 67.09; H, 6.33.

¹H NMR (CDCl₃): δ 7.28-7.70 (m, 13H, 7-H and 5,7-H in indenyls and Ph), 6.94 (s, 1H, 3-H in indenyl), 6.60 (s, 1H, 3-H in indenyl), 3.41 (s, 3H, OMe), 2.26 (s, 3H, 2-Me in indenyl), 2.23 (s, 3H, 2-Me in indenyl), 1.42 (s, 9H, ᵗBu), 1.36 (s, 3H, SiMeMe'), 1.35 (s, 9H, ᵗBu), 1.34 (s, 3H, SiMeMe').

Synthesis of anti-dimethylsilylene(2-methyl-4-phenyl-5-methoxy-6-tert-butyl-indenyl)(2-methyl-4-(4-tert-butyl-phenyl)indenyl)zirconium dichloride (Metallocene E2)

4/7-(4-tert-Butylphenyl)-2-methyl-3/1H-indene

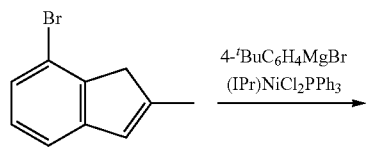

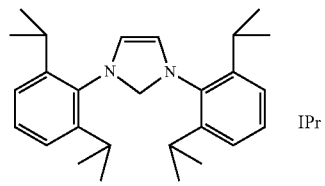

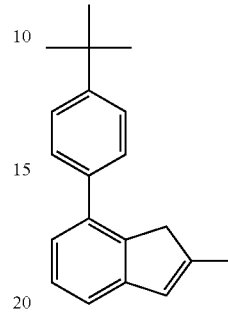

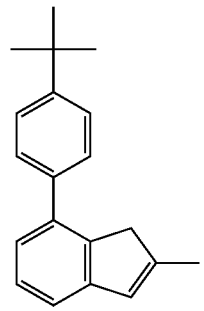

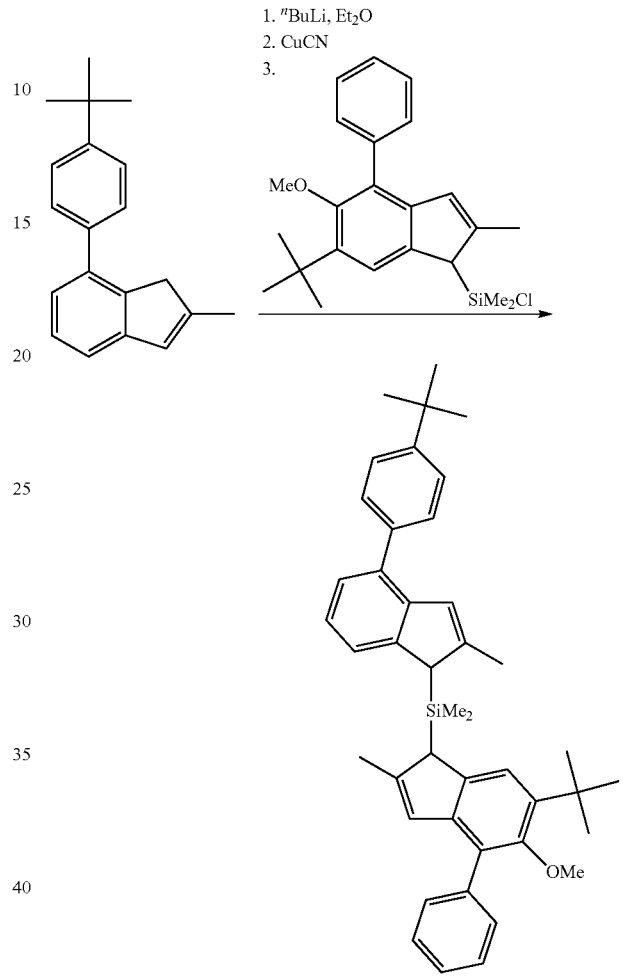

(6-tert-Butyl-5-methoxy-2-methyl-4-phenyl-1H-inden-1-yl)[4-(4-tert-butylphenyl)-2-methyl-1H-inden-1-yl]dimethylsilane To a solution of 4-tert-butylphenylmagnesium bromide obtained from 110 g (0.518 mol) of 1-bromo-4-tert-butylbenzene and 12.6 g (0.518 mol) of magnesium turnings in 500 ml of THF, 0.65 g (0.83 mmol) (IPr)NiCl₂PPh₃ and a solution of 77.6 g (0.371 mol) of 4/7-bromo-2-methyl-3/1H-indene in 50 ml of THF were added. This mixture was stirred at reflux for 30 min, and then for 20 min at room temperature. Finally, 150 ml of water and then 70 ml of 4 M HCl were added. The product was extracted with 200 ml of ether and then 2×100 ml of dichloromethane. The combined organic extract was dried over K₂CO₃, passed through a short column with Silica Gel 60, and evaporated to dryness. Rectification of the residue, b.p. 163-171° C./5 mm Hg, gave 93.8 g (96%) of a mixture of the title isomeric indenes as yellowish viscous oil which is slowly crystallized.

Anal. calc. for C₂₀H₂₂: C, 91.55; H, 8.45. Found: C, 91.62; H, 8.52.

¹H NMR (CDCl₃): δ 7.62 (m, C₆H₄ of both isomers), 7.46 (m, 5- and 6-H in 4- and 7-arylindenes), 7.40 (m, 7- and 4-H in 4- and 7-arylindenes), 7.31 (m, 6- and 5-H in 4- and 7-arylindenes), 6.88 (m, 3-H in 4/7-arylindene), 6.68 (m, 3-H in 7/4-arylindene), 3.55 (m, 1-CH₂ in 7/4-arylindene), 3.49 (m, 1-CH₂ in 4/7-arylindene), 2.28 (2-Me in 4/7-arylindene), 2.27 (2-Me in 7/4-arylindene), 1.54 (s, ᵗBu in 4- and 7-arylindenes).

To a solution of 11.5 g (43.8 mmol) of 7-(4-tert-butylphenyl)-2-methyl-1H-indene in 300 ml of ether, 17.0 ml (42.5 mmol) of 2.5 M ⁿBuLi in hexanes was added in one portion at −78° C. This mixture was stirred overnight at room temperature, then cooled to −60° C., and 150 mg of CuCN was added. The resulting mixture was stirred for 1 h at −20° C., then cooled to −70° C., and 16.2 g of (6-tert-butyl-5-methoxy-2-methyl-4-phenyl-1H-inden-1-yl)(chloro)-dimethylsilane (42.08 mmol) in 150 ml of ether was added. Further on, this mixture was stirred overnight at ambient temperature, then 0.5 ml of water was added. This solution was filtered through a pad of silica gel 60 (40-63 um) which was additionally washed by dichloromethane. The combined organic elute was evaporated to dryness, and the obtained yellowish oil was purified by flash chromatography on silica gel 60 (40-63 um; eluent: hexane-dichloromethane, from 10:1 to 3:1, vol.). This procedure gave 23.4 g (91%) of the title compound as yellowish glass.

Anal. Calcd. for C₄₃H₅₀OSi: C, 84.54; H, 8.25%. Found: C, 84.70; H, 8.33%.

¹H NMR (CDCl₃): δ 7.59-7.18 (m), 6.89 (m), 6.83 (m), 6.51 (m), 6.48 (m), 3.77 (m), 3.73 (m), 3.68-3.70 (m), 3.31

(s), 3.29 (s), 2.25 (s), 2.23 (s), 2.16 (s), 2.10 (s), 1.50 (s), 1.48 (s), 1.45 (s), 1.44 (s), 0.00 (s), −0.09 (s), −0.11 (s), −0.12 (s).

Anti- and syn-dimethylsilylene(2-methyl-4-phenyl-5-methoxy-6-tert-butyl-indenyl)(2-methyl-4-(4-tert-butyl-phenyl)indenyl)zirconium dichloride

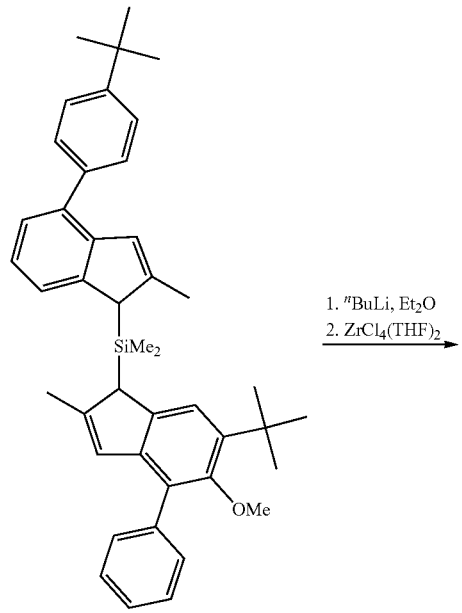

1. $^n$BuLi, Et$_2$O
2. ZrCl$_4$(THF)$_2$

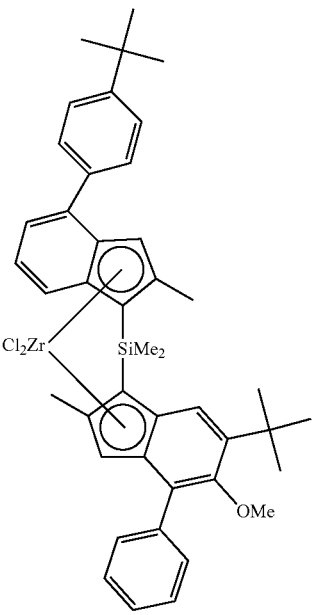

To a solution of 15.3 g (25.0 mmol) of (6-tert-butyl-5-methoxy-2-methyl-4-phenyl-1-inden-1-yl)[4-(4-tert-butylphenyl)-2-methyl-1H-inden-1-yl]dimethylsilane in 300 ml of ether cooled to −78° C., 20.0 ml (50.0 mmol) of 2.5 M $^n$BuLi in hexanes was added in one portion. This mixture was stirred overnight at room temperature, then cooled to −60° C., and 9.43 g (25.0 mmol) of ZrCl$_4$(THF)$_2$ was added. The resulting mixture was stirred for 24 h (a light orange solution with a significant amount of precipitate was formed), then evaporated to dryness, and 350 ml of toluene was added. The resulting solution warmed to 80° C. was filtered through glass frit (G4) to form on the evidence of NMR spectroscopy a ca. 1 to 1 mixture of anti- and syn-zirconocenes. Crystals precipitated overnight from this solution at room temperature were collected, washed by 2×10 ml of cold toluene, and dried in vacuum. This procedure gave 3.50 g of pure syn-zirconocene as a light-orange microcrystalline powder. The mother liquor was evaporated to ca. 100 ml. Crystals precipitated overnight from this solution at room temperature were collected, washed with 10 ml of cold toluene, and dried in vacuum. This procedure gave additional amount (4.10 g) of pure syn-zirconocene. Thus, the combined yield of pure syn-zirconocene was 7.60 g (39%) as a light-orange microcrystalline powder. Crystals precipitated after 3 days at room temperature were collected, washed by 10 ml of cold toluene, and dried in vacuum. This procedure gave 2.95 g of pure anti-zirconocene as a slightly orange microcrystalline powder. Additional amount of this product was obtained in a similar manner from mother liquor evaporated to ca. 35 ml. Thus, the combined yield of anti-zirconocene was 5.65 g (29%).

Anti-E2

Anal. Calcd. for $C_{43}H_{48}Cl_2OSiZr$: C, 66.98; H, 6.27%. Found: C, 67.00; H, 6.31%.

$^1$H NMR (CDCl$_3$): δ 7.61-7.63 (m, 3H, 2,6-H in C$_6$H$_4$ and 5-H in indenyl of I), 7.54 (s, 1H, 7-H in indenyl of II), 7.46-7.48 (m, 2H, 3,5-H in C$_6$H$_4$ of I), 7.42 (m, 2H, 3,5-H in Ph of II), 7.37 (d, J=7.1 Hz, 1H, 7-H in indenyl of I), 7.32 (m, 1H, 4-H in Ph of II), 7.09 (dd, J=8.6 Hz, J=7.1 Hz, 1H, 6-H in indenyl of I), 7.02 (s, 1H, 3-H in indenyl of II), 6.57 (s, 1H, 3-H in indenyl of I), 3.39 (s, 3H, OMe), 2.25 (s, 3H, 2-Me in I), 2.17 (s, 3H, 2-Me in II), 1.39 (s, 9H, 6-$^t$Bu in II), 1.33 (s, 9H, 4-$^t$Bu in I), 1.31 (s, 6H, SiMe$_2$); where I is 4-(4-tert-butylphenyl)-2-methyl-1H-inden-1-yl, II-6-tert-butyl-5-methoxy-2-methyl-4-phenyl-1H-inden-1-yl.

Syn-E2

Anal. Found: C, 66.12; H, 6.35%.

$^1$H NMR (CDCl$_3$): δ 7.64 (m, 1H, 5-H in indenyl of I), 7.56-7.58 (m, 2H, 2,6-H in C$_6$H$_4$ of I), 7.54 (s, 1H, 7-H in indenyl of II), 7.44-7.46 (m, 2H, 3,5-H in C$_6$H$_4$ of I), 7.41 (m, 2H, 3,5-H in Ph of II), 7.30 (m, 1H, 4-H in Ph of II), 7.15 (d, J=7.1 Hz, 1H, 7-H in indenyl of I), 6.91 (s, 1H, 3-H in indenyl of II), 6.87 (dd, J=8.6 Hz, J=7.1 Hz, 1H, 6-H in indenyl of I), 6.47 (s, 1H, 3-H in indenyl of I), 3.20 (s, 3H, OMe), 2.44 (s, 3H, 2-Me in I), 2.37 (s, 3H, 2-Me in II), 1.44 (s, 3H, SiMeMe'), 1.34 (s, 9H, 6-$^t$Bu in II), 1.33 (s, 9H, 4-$^t$Bu in I), 1.22 (s, 3H, SiMeMe'); where I is 4-(4-tert-butylphenyl)-2-methyl-1H-inden-1-yl, II—6-tert-butyl-5-methoxy-2-methyl-4-phenyl-1H-inden-1-yl.

Synthesis of anti-dimethylsilylene(2-methyl-4-phenyl-5-methoxy-6-tert-butyl-indenyl)(2-methyl-4-(3,5-di-tert-butyl-phenyl)-6-tert-butyl-indenyl)zirconium dichloride (Metallocene E3)

4/7-Bromo-2-methyl-6/5-tert-butyl-1H-indene

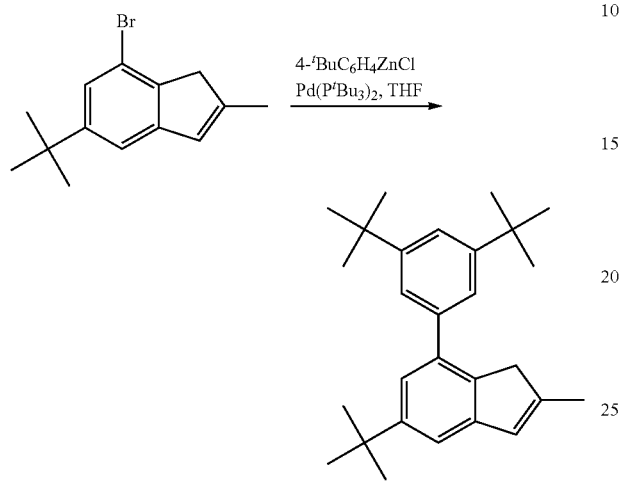

To 81.0 ml (47.0 mmol) of 0.58 M 3,5-di-tert-butylphenylmagnesium bromide in THF, 51.0 ml (51.0 mmol) of 1.0 M ZnCl$_2$ in THF was added. Further on, a solution of 11.4 g (43.0 mmol) of 7-bromo-2-methyl-5-tert-butyl-1H-indene and 438 mg of Pd(P$^t$Bu$_3$)$_2$ in 100 ml of THF was added. The resulting mixture was stirred overnight at 65° C., then cooled to room temperature and, finally, poured into 200 ml of water. The organic layer was separated, and the aqueous layer was extracted with 3×100 ml of ethyl acetate. The combined organic extract was washed with 2×100 ml of cold water, dried over Na$_2$SO$_4$, and evaporated to dryness. The residue was distilled in vacuum using Kugelrohr apparatus. This procedure gave 12.0 g (74%) of white crystalline solid.

Anal. Calcd. for C$_{28}$H$_{38}$: C, 89.78; H, 10.22%. Found: C, 89.69; H, 10.29%.

$^1$H NMR (CDCl$_3$): δ 7.42 (m), 7.38 (m), 7.35 (m), 7.30-7.32 (m), 7.19 (m), 6.59 (m, 3-H in indenyl), 6.62 (m, 3-H in indenyl), 3.36 (m, 1,1-H in indenyl), 3.33 (m, 1,1-H in indenyl), 2.13 (s, 2-Me in indenyl), 1.38-1.39 (s, 27H, $^t$Bu).

[6-tert-Butyl-4-(3,5-di-tert-butylphenyl)-2-methyl-1H-inden-1-yl]-(6-tert-butyl-5-methoxy-2-methyl-4-phenyl-1H-inden-1-yl)dimethylsilane

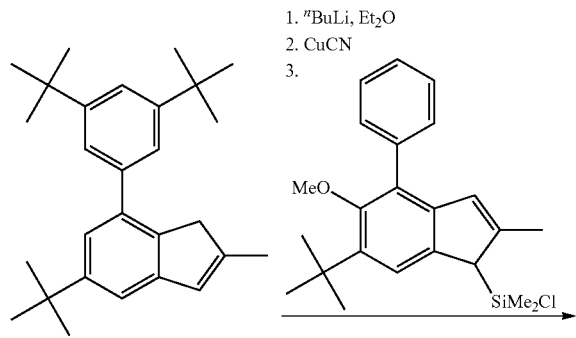

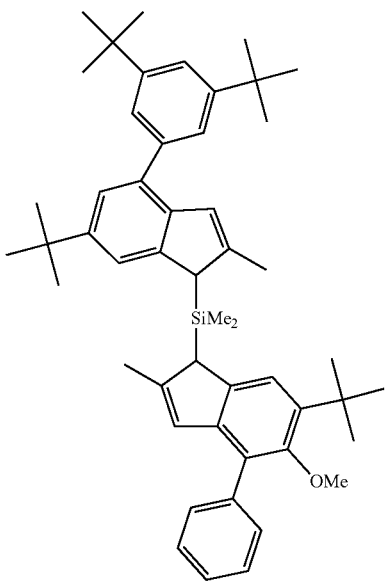

To a solution of 11.1 g (29.6 mmol) of 4/7-bromo-2-methyl-6/5-tert-butyl-1H-indene in 250 ml of ether, 11.9 ml (29.8 mmol) of 2.5 M $^n$BuLi in hexanes was added in one portion at −78° C. This mixture was stirred overnight at room temperature, then cooled to −60° C., and 150 mg of CuCN was added. The resulting mixture was stirred for 1 h at −20° C., and then a solution of 11.4 g (29.6 mmol) of (6-tert-butyl-5-methoxy-2-methyl-4-phenyl-1H-inden-1-yl)(chloro)-dimethylsilane in 200 ml of ether was quickly added at −70° C. The reaction mixture was allowed to warm to room temperature and stirred overnight, then treated with 0.5 ml of water, filtered through a short pad of silica gel 60 (40-63 um). The silica gel layer was additionally washed by 100 ml of dichloromethane. The combined elute was evaporated to dryness giving a yellowish oil which was purified by flash chromatography on silica gel 60 (4-63 μm; eluent: hexanes-dichloromethane from 10:1 to 3:1, vol.). This procedure gave 15.2 g (71%) of the title product as yellowish glassy solid.

Anal. Calcd. for C$_{51}$H$_{66}$OSi: C, 84.70; H, 9.20%. Found: C, 84.92; H, 9.34%.

$^1$H NMR (CDCl$_3$): δ 7.42-7.70 (m), 6.85 (s), 6.57 (s), 6.53 (s), 3.84 (m), 3.80 (m), 3.77 (m), 3.34 (s), 1.54 (s), 1.53 (s), 1.51 (s), 1.50 (s), 1.49 (s), 1.48 (s), −0.04 (s), −0.06 (s), −0.10 (s), −0.11 (s).

Complexes anti- and syn-dimethylsilanediyl[2-methyl-4-(3,5-di-tert-butylphenyl)-6-tert-butyl-inden-1-yl](2-methyl-4-phenyl-5-methoxy-6-tert-butyl-1H-inden-1-yl)zirconium dichloride

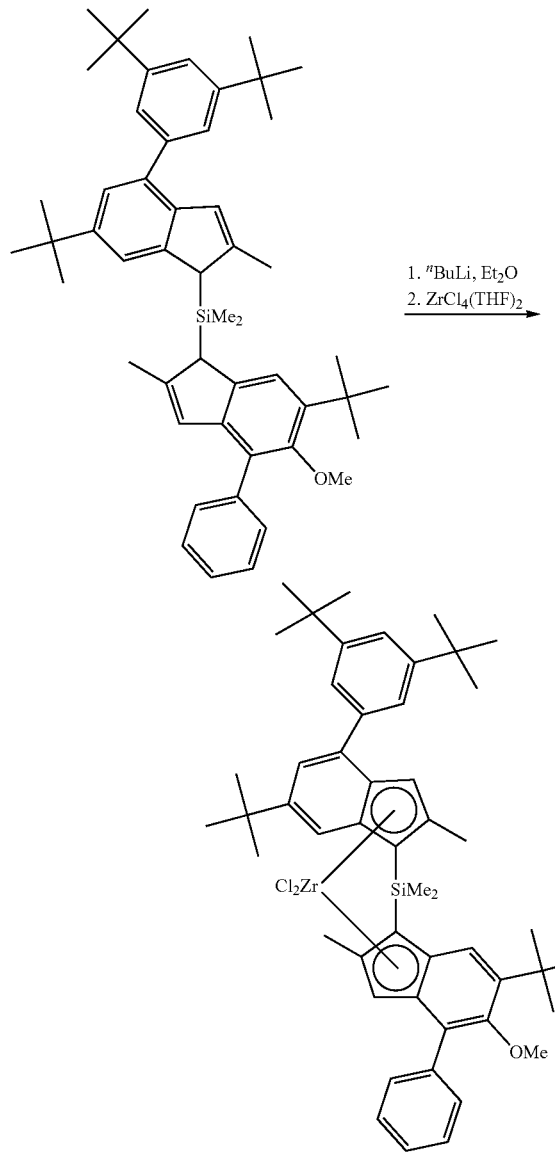

To a solution of 15.0 g (20.7 mmol) of [6-tert-butyl-4-(3,5-di-tert-butylphenyl)-2-methyl-1H-inden-1-yl](6-tert-butyl-5-methoxy-2-methyl-4-phenyl-1H-inden-1-yl)dimethylsilane in 200 ml of ether cooled to −78° C., 16.5 ml (41.3 mmol) of 2.5 M $^n$BuLi in hexanes was added in one portion. This mixture was stirred overnight at room temperature, then cooled to −78° C., and 7.80 g (20.7 mmol) of ZrCl$_4$(THF)$_2$ was added. The resulting mixture was stirred for 24 h (a light orange solution with a significant amount of precipitate was formed), then evaporated to dryness, and 350 ml of toluene was added. The resulting mixture warmed to 80° C. was filtered through glass frit (G4). On the evidence of NMR spectroscopy, this mixture contained anti- and syn-zirconocenes in a ratio of ca. 70:30. The filtrate was evaporated to 100 ml, warmed to 80° C., and 25 ml of n-octane was added. Crystals precipitated after 24 h at −30° C. were collected, washed by 2×10 ml of a ca. 1 to 1 (vol.) mixture of toluene and n-hexane, and dried in vacuum. This procedure gave 6.62 g (36%) of pure anti-zirconocene as a light-orange crystalline powder. The mother liquor was evaporated to 50 ml, diluted with 100 ml of n-hexane, and crystallized overnight at −30° C. The formed precipitate was filtered through glass frit (G3) and then dried in vacuum. This procedure gave 6.40 g of a mixture of anti- and syn-zirconocene in the ratio of 3:2. The mother liquor was evaporated to dryness, and the residue was dissolved in 20 ml of hot n-octane. Crystals precipitated at −30° C. were collected, washed by 2×5 ml of cold n-hexane, and dried in vacuum. This procedure gave additional amount (450 mg) of pure anti-zirconocene. A precipitate formed after keeping a mother liquor at room temperature for 3 days was filtered off (G3), and then dried in vacuum. This procedure gave 210 mg of pure syn-zirconocene.

anti-E3

Anal. Calcd. for $C_{51}H_{64}Cl_2OSiZr$: C, 69.35; H, 7.30%. Found: C, 69.43; H, 7.41%.

$^1$H NMR (CDCl$_3$): δ 7.15-7.60 (m, 11H, 5,7-H in indenyl and 2,4,6-H in aryl of I as well as 7-H in indenyl and Ph in II), 6.87 (s, 1H, 3-H in indenyl of I), 6.53 (s, 1H, 3-H in indenyl of II), 3.40 (s, 3H, OMe), 2.22 (s, 3H, 2-Me in indenyl), 2.20 (s, 3H, 2-Me in indenyl), 1.40 (s, 9H, 6-$^t$Bu in indenyl of I), 1.36 (s, 18H, 3,5-$^t$Bu in aryl), 1.33 (s, 9H, 6-$^t$Bu in indenyl of II), 1.32 (s, 3H, SiMeMe'), 1.30 (s, 3H, SiMeMe'), where I is 6-tert-butyl-4-(3,5-di-tert-butylphenyl)-2-methyl-1H-inden-1-yl, II—6-tert-butyl-5-methoxy-2-methyl-4-phenyl-1H-inden-1-yl.

syn-E3

Anal. Found: C, 69.47; H, 7.40%.

$^1$H NMR (CDCl$_3$): δ 7.16-7.54 (m, 11H, 5,7-H in indenyl and 2,4,6-H in aryl of I as well as 7-H in indenyl and Ph in II), 6.88 (s, 1H, 3-H in indenyl of I), 6.53 (s, 1H, 3-H in indenyl of II), 3.17 (s, 3H, OMe), 2.45 (s, 3H, 2-Me in indenyl), 2.40 (s, 3H, 2-Me in indenyl), 1.45 (s, 3H, SiMeMe'), 1.38 (s, 18H, 3,5-$^t$Bu in aryl), 1.35 (s, 9H, 6-$^t$Bu in indenyl of I), 1.31 (s, 9H, 6-$^t$Bu in indenyl of II), 1.21 (s, 3H, SiMeMe'), where I is 6-tert-butyl-4-(3,5-di-tert-butylphenyl)-2-methyl-1H-inden-1-yl, II—6-tert-butyl-5-methoxy-2-methyl-4-phenyl-1H-inden-1-yl.

Synthesis of anti-dimethylsilanediyl[2-methyl-4-(4-tert-butylphenyl)-inden-1-yl][2-methyl-4-phenyl-5-(pentafluorophenoxy)-6-isopropyl-inden-1-yl]zirconium dichloride (Metallocene E4)

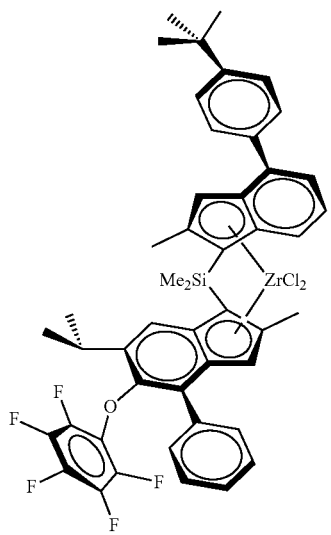

1-(Pentafluorophenoxy)-2-isopropylbenzene

4-Bromo-6-isopropyl-2-methyl-5-(pentafluorophenoxy)indan-1-one

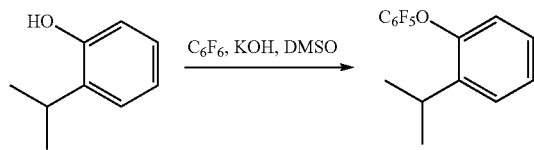

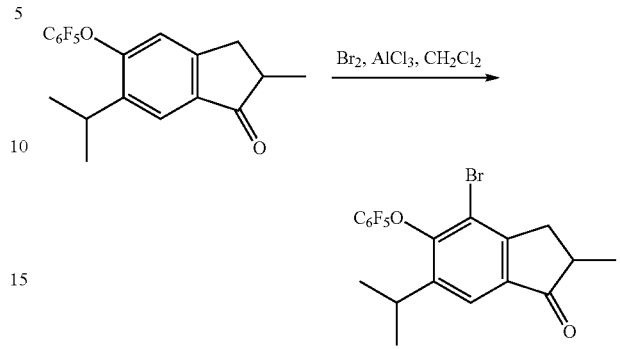

A mixture of 50.0 g (0.36 mol) of 2-isopropylphenol, 137 g (0.72 mol) of hexafluorobenzene, 50.4 g (0.90 mol) of KOH powder, and 1000 ml of DMSO was stirred for 48 h at 80° C. This mixture was cooled to room temperature and then poured in 3000 ml of water. The product was extracted with 4×500 ml of dichloromethane. The combined organic extract was dried over $Na_2SO_4$ and then evaporated on Rotavap. The residue was distilled in vacuum, 130-140° C./13 mm Hg.

Yield 68.3 g (63%).

Anal. calc. for $C_{15}H_{11}F_5O$: C, 59.61; H, 3.67. Found: C, 59.76; H, 3.80.

$^1$H NMR (CDCl$_3$): δ 7.42-7.38 (m, 1H, 4-H), 7.17-7.12 (m, 2H, 3,5-H), 6.61 (m, 1H, 6-H), 3.61-3.53 (m, 1H, CHMe$_2$), 1.42-1.36 (m, 6H, CHMe$_2$).

6-Isopropyl-2-methyl-5-(pentafluorophenoxy)indan-1-one

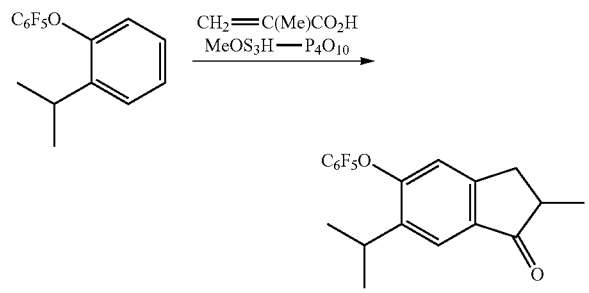

A mixture of 39.3 g (0.46 mol) of methacrylic acid and 115 g (0.38 mol) of 1-(pentafluorophenoxy)-2-isopropylbenzene was added dropwise to Eaton's reagent (prepared from 99 g of $P_4O_{10}$ and 500 ml of MeSO$_3$H) for 1 h at 70° C. The resulting mixture was stirred at 70° C. for 1 h, then cooled to room temperature, and poured on 1000 cm$^3$ of ice. The crude product was extracted with 3×200 ml of dichloromethane. The organic extract was washed with aqueous $K_2CO_3$, dried over $Na_2SO_4$, and then evaporated to dryness. The product was purified by flash chromatography on silica gel 60 (40-63 um; eluent: n-hexane-dichloromethane=5:1, vol., then n-hexane-dichloromethane-ether=50:25:1, vol.) to give 30.1 g (20%) of the title indanone. Additionally, 39.4 g of the starting 1-(pentafluorophenoxy)-2-isopropylbenzene was isolated also.

Anal. calc. for $C_{19}H_{15}F_5O_2$: C, 61.62; H, 4.08. Found: C, 61.85; H, 4.22.

$^1$H NMR (CDCl$_3$): δ 7.76 (s, 1H, 7-H), 6.54 (s, 1H, 4-H), 3.49 (sept, J=6.8 Hz, 1H, CHMe$_2$), 3.25 (dd, J=17.1 Hz, J=7.7 Hz, 1H, 3-H), 2.74-2.65 (m, 1H, 2-H), 2.59 (dd, J=17.1 Hz, J=3.5 Hz, 1H, 3'-H), 1.33 (d, J=6.8 Hz, 6H, CHMe$_2$), 1.29 (d, J=7.5 Hz, 3H, 2-Me).

To a suspension of 17.5 g (131 mmol) of AlCl$_3$ in 28 ml of dichloromethane cooled to −20° C. a solution of 32.4 g (87.5 mmol) of 6-isopropyl-2-methyl-5-(pentafluorophenoxy)indan-1-one in 46 ml of dichloromethane was added dropwise. Further on, this solution was warmed to 0° C., and 4.80 ml (96.0 mmol) of bromine was added dropwise by vigorous stirring for 0.5 h. This mixture was stirred for 24 h at room temperature and then poured in cold aqueous $Na_2SO_3$ to remove an excess of bromine. The product was extracted with 3×50 ml of dichloromethane. The combined extract was evaporated to dryness. The product was isolated by flash chromatography on silica gel 60 (40-63 um; eluent: n-hexane-dichloromethane-ether 50:50:1, vol.). Yield 20.1 g (51%). Additionally, 15.0 g of the starting indanone was recovered.

Anal. calc. for $C_{19}H_{14}BrF_5O_2$: C, 50.80; H, 3.14. Found: C, 51.14; H, 3.40.

$^1$H NMR (CDCl$_3$): δ 7.72 (s, 1H, 7-H), 3.38-2.28 (m, 2H, 3-H and CHMe$_2$), 2.82-2.73 (m, 1H, 2-H), 2.62 (dd, J=17.5 Hz, J=3.9 Hz, 1H, 3'-H), 1.34 (d, J=7.5 Hz, 3H, 2-Me), 1.27 (d, J=6.9 Hz, 6H, CHMe$_2$).

5-Isopropyl-2-methyl-6-(pentafluorophenoxy)-7-phenyl-1H-indene

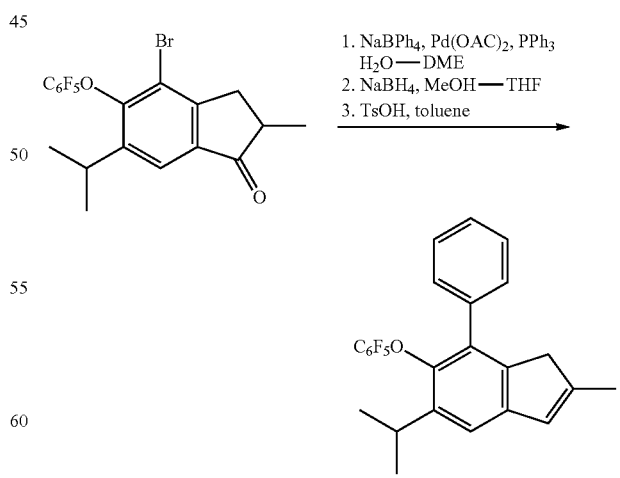

A mixture of 33.4 g (74.4 mmol) of 4-bromo-5-(pentafluorophenoxy)-6-isopropyl-2-methylindanone, 25.4 g (74.4 mmol) of NaBPh$_4$, 21.8 g (206 mmol) of Na$_2$CO$_3$, 1.00 g (4.46 mmol, 6 mol. %) of Pd(OAc)$_2$, 2.34 g (8.93 mmol, 12 mol. %) of PPh₃, 100 ml of water, and 300 ml of DME was refluxed for 12 h and then quenched with water. Organic solvents were evaporated using Rotavap. The residue was dissolved in 500 ml of dichloromethane, the solution was washed with 500 ml of water. The organic layer was separated, the aqueous layer was additionally extracted with 100 ml of dichloromethane. The combined organic solution was evaporated to dryness. Crude product was isolated by flash chromatography on silica gel 60 (40-63 um; eluent: n-hexane-dichloromethane=2:1, vol.). Further on, this crude product was re-crystallized from n-hexane to give 27.3 g (80%) of a yellowish solid of the respective aryl-substituted indanone. To a mixture of 14.8 g (32.0 mmol) of this aryl-substituted indanone and 1.88 g of NaBH₄ in 100 ml of THF 50 ml of methanol was added dropwise by vigorous stirring for 1 h at 0° C. This mixture was stirred overnight at room temperature and then evaporated to dryness. The residue was dissolved in 50 ml of dichloromethane, and this solution was washed by 3×50 ml of water and then evaporated to dryness. To a solution of the residue in 250 ml of toluene 250 mg of TsOH was added. This mixture was refluxed for 15 min with Dean-Stark head and then cooled to room temperature using a water bath. The resulting reddish solution was washed by 10% aqueous Na₂CO₃, the organic layer was separated, and the aqueous layer was extracted with 2×100 ml of dichloromethane. The combined organic solution was dried over K₂CO₃ and then filtered through a short pad of silica gel 60 (40-63 um). The silica gel layer was additionally washed by 50 ml of dichloromethane. The combined organic elute was evaporated to dryness to give 14.6 g (99%) of the title product as a yellowish oil.

Anal. calc. for C₂₅H₁₉F₅O: C, 69.76; H, 4.45. Found: C, 69.95; H, 4.49.

¹H NMR (CDCl₃): δ 7.26-7.12 (m, 5H, 2,3,4,5,6-H in Ph), 6.48 (s, 1H, 3-H in indenyl), 3.41 (sept, J=6.9 Hz, 1H, CHMe₂), 3.03 (s, 2H, 1-H in indenyl), 2.06 (s, 3H, 2-Me in indenyl), 1.30 (d, J=6.9 Hz, 6H, CHMe₂).

Chloro[6-isopropyl-2-methyl-5-(pentafluorophenoxy)-4-phenyl-1H-inden-1-yl]dimethylsilane to remove an excess of KH, then cooled to −25° C., and 13.0 g (101 mmol, 5 eq.) of dichlorodimethylsilane was added in one portion. The resulting solution was stirred overnight at room temperature, then evaporated to dryness. The residue was dissolved in 200 ml of toluene, and the formed suspension was filtered through glass frit (G3). The precipitate was additionally washed by 2×30 ml of toluene. The combined filtrate was evaporated to dryness to give 10.5 g (99%) of the title product which was further used without an additional purification.

Anal. calc. for C₂₇H₂₄ClF₅OSi: C, 62.00; H, 4.63. Found: C, 62.53; H, 4.80.

¹H NMR (CDCl₃): δ 7.43 (s, 1H, 7-H in indenyl), 7.27-7.18 (m, 5H, 2,3,4,5,6-H in Ph), 6.31 (s, 1H, 3-H in indenyl), 3.64 (s, 1H, 1-H in indenyl), 3.43 (sept, J=6.7 Hz, 1H, CHMe₂), 2.19 (s, 3H, 2-Me in indenyl), 1.30 (t, J=6.7 Hz, 6H, CHMe₂), 0.38 (s, 3H, SiMeMe'Cl), 0.19 (s, 3H, SiMeMe'Cl).

[4-(4-tert-Butylphenyl)-2-methyl-1H-inden-1-yl][6-isopropyl-2-methyl-5-(pentafluoro phenoxy)-4-phenyl-1H-inden-1-yl]dimethylsilane

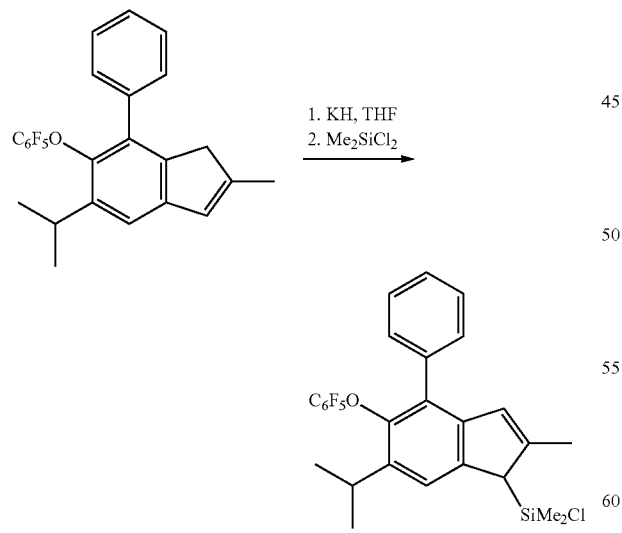

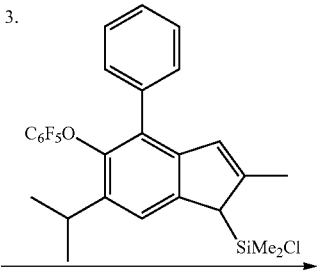

To a solution of 8.61 g (20.0 mmol) of 5-isopropyl-2-methyl-6-(pentafluorophenoxy)-7-phenyl-1H-indene in 200 ml of THF cooled to −25° C., 885 mg (22.1 mmol) of potassium hydride was added. The resulting mixture was stirred overnight at room temperature, filtered through glass frit (G3)

To a solution of 6.39 g (24.4 mmol) of 7-(4-tert-butylphenyl)-2-methyl-1H-indene in 200 ml of ether 9.80 ml (24.5 mmol) of 2.5 M "BuLi in hexanes was added in one portion at −40° C. This mixture was stirred overnight at room temperature, then cooled to −40° C., and 150 mg of CuCN was added. The resulting mixture was stirred for 1 h at −20° C., then cooled to −40° C., and a solution of 10.5 g (20.0 mmol) of chloro[6-isopropyl-2-methyl-5-(pentafluorophenoxy)-4-phenyl-1H-inden-1-yl]dimethylsilane in 200 ml of ether was added in one portion. Further on, this mixture was stirred overnight at ambient temperature, then 0.5 ml of water was added. This solution was filtered through a pad of silica gel 60 (40-63 um) which was then additionally washed by 2×75 ml of dichloromethane. The combined organic elute was evaporated to dryness, and the residue was dried in vacuum. The product was isolated by flash-chromatography on silica gel 60 (40-63 um; eluent: hexanes-dichloromethane=10:1, vol., then 5:1, vol.). This procedure gave 7.86 g (53%) of the title product (of ca. 90% purity as a ca. 1:1 mixture of the stereoisomers on the evidence of NMR spectroscopy) as a yellowish glass.

Anal. calc. for $C_{47}H_{45}F_5OSi$: C, 75.37; H, 6.06. Found: C, 75.91; H, 6.55.

$^1$H NMR (CDCl$_3$): δ 7.49 (s), 7.46 (s), 7.41-7.36 (m), 7.30-7.16 (m), 6.86 (s), 6.79 (s), 6.32 (s), 6.26 (s), 3.76 (s), 3.71 (s), 3.70 (s), 3.68 (s), 3.46-3.38 (m), 2.21 (s), 2.18 (s), 2.13 (s), 2.02 (s), 1.39 (s), 1.29-1.26 (m), −0.10 (s), −0.11 (s), −0.18 (s), −0.20 (s).

Anti-dimethylsilanediyl[2-methyl-4-(4-tert-butylphenyl)-inden-1-yl][2-methyl-4-phenyl-5-(pentafluorophenoxy)-6-isopropyl-inden-1-yl]zirconium dichloride (Metallocene E4)

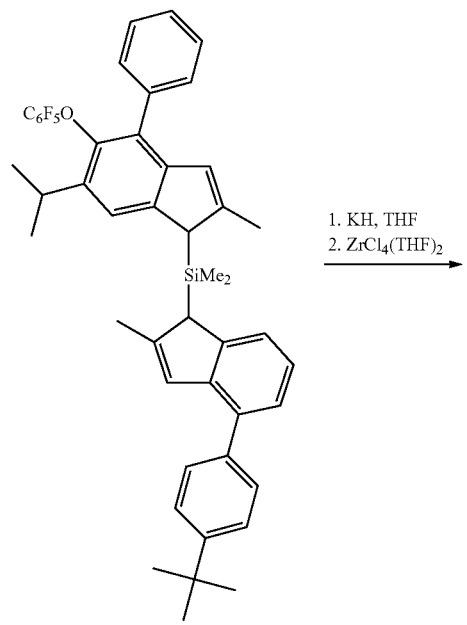

1. KH, THF
2. ZrCl$_4$(THF)$_2$

-continued

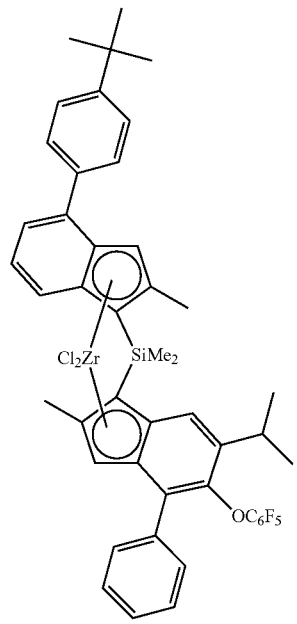

To a solution of 3.93 g (5.25 mmol) of [4-(4-tert-butylphenyl)-2-methyl-1H-inden-1-yl][6-isopropyl-2-methyl-5-(pentafluorophenoxy)-4-phenyl-1H-inden-1-yl]dimethylsilane (obtained as described above) in 100 ml of THF cooled to −25° C. 463 mg (11.5 mmol, 2.2 eq.) of potassium hydride was added. The resulting mixture was stirred overnight at room temperature, then filtered through glass frit (G3) to remove an excess of KH (the precipitate was additionally washed by 10 ml of THF). The combined filtrate was cooled to −25° C., and 1.98 g (5.25 mmol) of ZrCl$_4$(THF)$_2$ was added in one portion. The resulting solution was stirred overnight at room temperature, then evaporated to dryness. The residue was dissolved in 100 ml of warm toluene, the formed suspension was filtered through glass frit (G4), and the precipitate was additionally washed by 2×10 ml of toluene. The combined filtrate was evaporated to dryness, the residue was dissolved in 45 ml of n-octane. Crystals precipitated from this solution after 2 days at −30° C. were collected, washed with 3×10 ml of n-hexane, and discarded. The mother liquor was evaporated to dryness, and 25 ml of n-hexane was added. Crystals precipitated from this solution overnight at room temperature were collected, washed with 3 ml of n-hexane, and dried in vacuum. This procedure gave 0.55 g (12%) of anti-zirconocene. Assignment in NMR spectra was made using the following abbreviations: L$^1$ for 4-(4-tert-butylphenyl)-2-methyl-1H-inden-1-yl and L$^2$ for 6-isopropyl-2-methyl-5-(pentafluorophenoxy)-4-phenyl-1H-inden-1-yl.

anti-Zirconocene.

Anal. calc. for $C_{47}H_{43}Cl_2F_5OSiZr$: C, 62.10; H, 4.77. Found: C, 62.29; H, 4.70.

$^1$H NMR (CDCl$_3$): δ 7.62 (s, 1H, 7-H in L$^2$), 7.59 (d, J=8.8 Hz, 1H, 7-H in L$^1$), 7.54 (dt, J=8.6 Hz, J=2.1 Hz, 2H, 2,6-H in C$_6$H$_4$$^t$Bu), 7.45 (dt, J=8.6 Hz, J=2.1 Hz, 2H, 3,5-H in C$_6$H$_4$$^t$Bu), 7.40 (br. s, 2H, 2,6-H in Ph), 7.33 (dd, J=7.0 Hz, J=0.6 Hz, 1H, 5-H in L$^1$), 7.25-7.15 (m, 3H, 3,4,5-H in Ph), 7.06 (dd, J=8.8 Hz, J=7.0 Hz, 1H, 6-H in L$^1$), 7.01 (s, 1H, 3-H in L$^1$), 6.39 (s, 1H, 3-H in L$^2$), 3.40 (sept, J=6.7 Hz, 1H, CHMe$_2$), 2.34 (s, 3H, 2-Me in L$^1$), 2.17 (s, 3H, 2-Me in L$^2$), 1.36 (s, 3H, CHMeMe'), 1.34 (s, 9H, ʹBu in C$_6$H$_4$ʹBu), 1.32 (s, 3H, CHMeMe'), 1.29 (s, 3H, SiMeMe'), 1.27 (s, 3H, SiMeMe').

Synthesis of anti-dimethylsilanediyl(2-methyl-4-phenyl-5-methoxy-6-tert-butyl-indenyl)[2,7-dimethyl-4-(3,5-di-tert-butylphenyl)indenyl]zirconium dichloride (Metallocene E5)

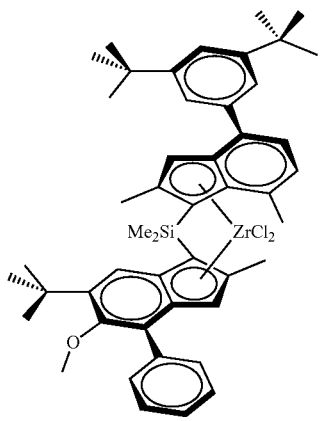

5-Bromo-2-methylbenzaldehyde

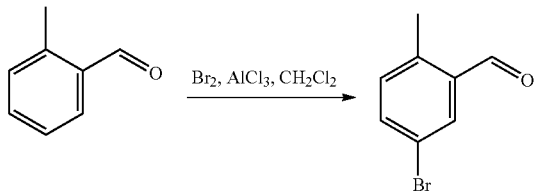

To a suspension of 344 g (2.58 mol, 1.5 eq.) of AlCl$_3$ in 1100 cm$^3$ of dichloromethane 206.8 g (1.72 mol) of 2-methylbenzaldehyde was added dropwise by vigorous stirring for 15 min at 5° C. The resulting mixture was stirred for 15 min at 5° C., and then 88.9 ml (276 g, 1.73 mol) of bromine was added for 1 h at this temperature. The final mixture was additionally stirred for 6 h at room temperature and then poured on 2 kg of ice. The organic layer was separated, the aqueous layer was extracted with 2×200 ml of dichloromethane. The combined organic extract was washed by aqueous NaHCO$_3$, dried over Na$_2$SO$_4$, and then evaporated to dryness to yield reddish liquid. This crude product was distilled in vacuum, b.p. 100-120° C./5 mM Hg. The obtained colorless liquid (which completely crystallizes at 5° C.) was dissolved in 900 ml of n-hexane. Crystals precipitated from this solution for 3 days at 5° C. were collected and dried in vacuum. On the evidence of NMR spectroscopy this mixture consists of 5-bromo-2-methylbenzaldehyde and 3-bromo-2-methylbenzaldehyde in ratio equal ca. 3 to 1. This mixture was recrystallized from 500 ml of hot n-hexane. White crystals precipitated at 5° C. were collected, washed by 150 ml of cold (+5° C.) n-hexane, and dried in vacuum (~60° C./20 mM Hg) to give colorless liquid which crystallizes at room temperature. Yield 80.9 g (24%) of 5-bromo-2-methylbenzaldehyde including ca. 2% of 3-bromo-2-methylbenzaldehyde.

Anal. calc. for C$_8$H$_7$BrO: C, 48.27; H, 3.54. Found: C, 48.05; H, 3.41.

$^1$H NMR (CDCl$_3$): δ 10.21 (s, 1H, CHO), 7.90 (d, J=2.2 Hz, 1H, 6-H), 7.57 (dd, J=8.2 Hz, J=2.3 Hz, 1H, 4-H), 7.14 (d, J=8.2 Hz, 1H, 3-H), 2.61 (s, 3H, Me). $^{13}$C{$^1$H} NMR (CDCl$_3$): δ 191.0, 139.3, 136.4, 135.5, 134.1, 133.4, 120.0, 18.85.

5-Bromo-2-methylbenzyl chloride

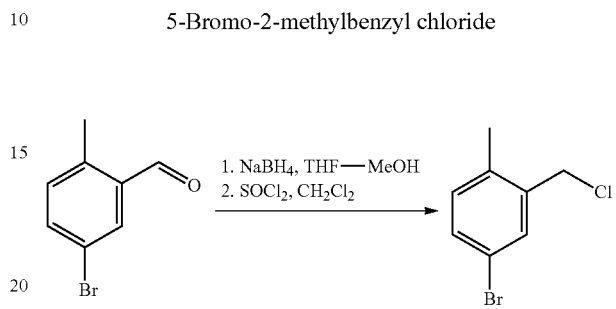

To a mixture of 80.9 g (0.406 mol) of 5-bromo-2-methylbenzaldehyde and 7.80 g (0.206 mol) of NaBH$_4$ in 300 ml of THF 200 ml of methanol was added dropwise by vigorous stirring for 5 h at 0-5° C. This mixture was stirred overnight at room temperature and then added to 1 liter of cold water. The resulting mixture was acidified by 2 M HCl to pH~1, and the formed (5-bromo-2-methylphenyl)methanol was extracted with 3×250 ml of dichloromethane. The combined organic extract was dried over Na$_2$SO$_4$ and evaporated to dryness. To the residue dissolved in 450 ml of dichloromethane 37 ml of SOCl$_2$ was added dropwise at +5° C. The resulting solution was stirred overnight at room temperature, evaporated to dryness, the residue was dissolved in 500 ml CH$_2$Cl$_2$, and the obtained solution was washed with 500 ml of water. The organic layer was separated, the aqueous layer was additionally extracted with 2×100 ml of dichloromethane. The combined organic extract was passed through a short pad of silica gel 60 (40-63 um), the filtrate was evaporated to dryness, and the residue was dried in vacuum to yield 5-bromo-2-methylbenzyl chloride as a slightly yellowish liquid which was further used without an additional purification.

Anal. calc. for C$_8$H$_8$BrCl: C, 43.77; H, 3.67. Found: C, 43.89; H, 3.80.

$^1$H NMR (CDCl$_3$): δ 7.45 (d, J=2.0 Hz, 1H, 3-H), 7.35 (dd, J=8.2 Hz, J=2.0 Hz, 1H, 5-H), 7.06 (d, J=8.2 Hz, 1H, 6-H), 4.53 (s, 2H, CH$_2$Cl), 2.36 (s, 3H, Me).

$^{13}$C {$^1$H} NMR (CDCl$_3$): δ 137.5, 136.0, 132.4, 132.3, 131.7, 119.5, 43.8, 18.3.

3-(5-Bromo-2-methylphenyl)-2-methylpropanoyl chloride

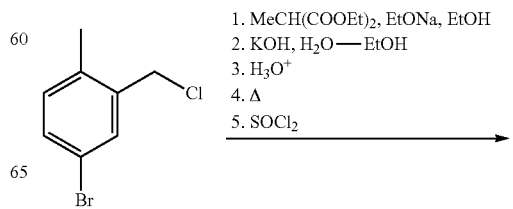

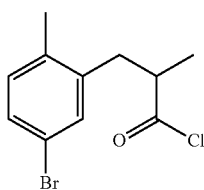

In a three-necked round-bottom flask 9.50 g (0.413 mol) of sodium metal was dissolved in 260 ml of dry ethanol. To the resulting solution 72.0 g (0.413 mol) of diethyl methylmalonate was added. This mixture was stirred for 15 min, then 5-bromo-2-methylbenzyl chloride prepared above was added by vigorous stirring at such a rate as to maintain gentle reflux. This mixture was refluxed for an additional 2 h and then cooled to room temperature. A solution of 85 g of KOH in 250 ml of water was added. The resulting mixture was refluxed for 4 h to saponificate the ester formed. Ethanol and water were distilled off until temperature reached 95° C., and 1000 ml of water and then 12 M HCl (to pH 1) were added to the residue. The precipitated substituted methylmalonic acid was filtered off, washed with 3×100 ml of water, and then decarboxylated at 180° C. to give 3-(5-bromo-2-methylphenyl)-2-methylpropanoic. A mixture of this acid and 105 ml of SOCl$_2$ was stirred at room temperature for 24 hours. After evaporation of an excess of thionyl chloride, the residue was distilled in vacuum to give 85.3 g (75% from 5-bromo-2-methylbenzaldehyde) 3-(5-bromo-2-methylphenyl)-2-methylpropanoyl chloride, b.p. 115° C./1 mm Hg.

Anal. calc. for C$_{11}$H$_{12}$BrClO: C, 47.94; H, 4.39. Found: C, 48.12; H, 4.45.

$^1$H NMR (CDCl$_3$): δ 7.28-7.26 (m, 2H, 6,4-H in Ph), 7.03 (d, J=7.7 Hz, 1H, 3-H in Ph), 3.18 (dd, J=13.8 Hz, J=5.9 Hz, 1H, ArCHH'), 3.10 (m, 1H, CHCOCl), 2.65 (dd, J=13.8 Hz, J=8.1 Hz, 1H, ArCHH'), 2.28 (s, 3H, ArMe), 1.29 (d, J=6.7 Hz, 3H, CHMe). $^{13}$C{$^1$H} NMR (CDCl$_3$): δ 176.9, 138.1, 135.2, 132.4, 132.2, 130.0, 119.5, 51.8, 36.1, 19.0, 16.6.

7-Bromo-2,4-dimethylindan-1-one

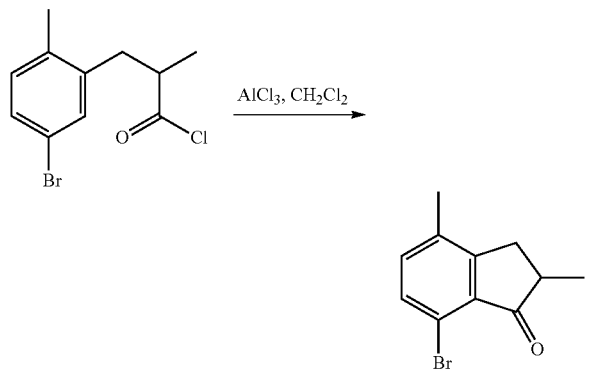

To a stirred suspension of 49.5 g (0.371 mol, 1.2 eq.) of AlCl$_3$ in 300 ml of dichloromethane a solution of 85.3 g (0.310 mol) of 3-(5-bromo-2-methylphenyl)-2-methylpropanoyl chloride in 50 ml of dichloromethane was added dropwise. This mixture was stirred overnight at room temperature and then poured on 500 g of ice. The organic layer was separated, and the aqueous layer was additionally extracted with 3×75 ml of dichloromethane. The combined organic extract was washed by aqueous K$_2$CO$_3$, dried over K$_2$CO$_3$, passed through a short pad of silica gel, and then evaporated to dryness. This procedure gave 74.0 g (>99%) of 7-bromo-2,4-dimethylindan-1-one as a light-orange liquid, solidified at room temperature, which was further used without an additional purification.

Anal. calc. for C$_{11}$H$_n$BrO: C, 55.25; H, 4.64. Found: C, 55.40; H, 4.81.

$^1$H NMR (CDCl$_3$): δ 7.41 (d, J=8.0 Hz, 1H, 6-H in indan-1-one), 7.21 (d, J=8.0 Hz, 1H, 5-H in indan-1-one), 3.24 (dd, J=17.3 Hz, J=7.9 Hz, 3-H in indan-1-one), 2.73 (m, 1H, 2-H in indan-1-one), 2.54 (dd, J=17.3 Hz, J=4.1 Hz, 1H, 3'-H in indan-1-one), 2.29 (s, 3H, 4-Me in indan-1-one), 1.33 (d, J=7.3 Hz, 3H, 2-Me in indan-1-one). $^{13}$C{$^1$H} NMR (CDCl$_3$): δ 207.0, 155.0, 135.6, 134.8, 133.1, 132.3, 116.5, 42.4, 33.0, 17.4, 16.4.

7-Bromo-1-methoxy-2,4-dimethylindane

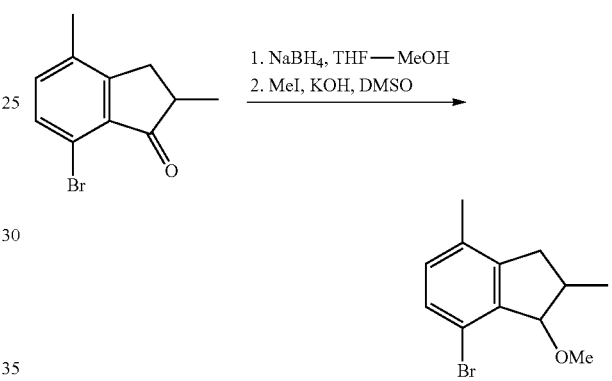

To a mixture of 74.0 g (0.310 mol) of 7-bromo-2,4-dimethylindan-1-one and 5.86 g (0.155 mol) of NaBH$_4$ in 310 ml of THF 155 ml of methanol was added dropwise by vigorous stirring for 5 h at 0-5° C. This mixture was stirred overnight at room temperature and then added to 1 liter of cold water. The resulting mixture was acidified by 2 M HCl to pH~5, and then it was extracted with 3×250 ml of dichloromethane. The combined organic extract was dried over Na$_2$SO$_4$ and evaporated. The resulting orange oil was dissolved in 600 ml of DMSO, then 70 g (1.25 mol) of KOH and 88 g (0.62 mol) of MeI were added to the resulting solution. This mixture was stirred for 3 h at ambient temperature. Further on, the solution was decanted from an excess of KOH, the latter was washed with 2×200 ml of dichloromethane, and 2000 cm$^3$ of water was added to the combined solution. The organic layer was separated, and the aqueous layer was additionally extracted with 2×100 ml of dichloromethane. The combined organic extract was additionally washed with 5×1500 ml of water, dried over Na$_2$SO$_4$, and evaporated to dryness. Fractional distillation of the residue in vacuum gave 72.3 g (92%) of 7-bromo-1-methoxy-2,4-dimethylindane, b.p. 107-112° C./5 mm Hg.

Anal. calc. for C$_{12}$H$_{15}$BrO: C, 56.49; H, 5.93. Found: C, 56.43; H, 6.02.

$^1$H NMR (CDCl$_3$): δ 7.25 (t, J=8.57 Hz, 2H, 6-H of syn- and anti-isomers), 6.93 (t, J=8.57 Hz, 2H, 5H of syn- and anti-isomers), 4.57 (d, J=5.5 Hz, 1H, 1-H of syn-isomer), 4.42 (s, 1H, 1-H of anti-isomer), 3.53 (s, 3H, OMe of syn-isomer), 3.45 (s, 3H, OMe of anti-isomer), 3.27 (dd, J=16.6 Hz, J=7.3 Hz, 1H, 3-H of anti-isomer), 2.87 (dd, J=15.7 Hz, J=7.5 Hz, 1H, 3-H of syn-isomer), 2.68 (dd, J=15.7 Hz, J=9.8 Hz, 1H, 3'-H of syn-isomer), 2.57 (m, 1H, 2-H of anti-isomer), 2.44 (m, 1H, 2-H of syn-isomer), 2.39 (dd, J=16.6 Hz, J=1.4 Hz, 3'-H of anti-isomer), 2.18 (s, 6H, 4-Me of syn- and anti-isomers), 1.26 (d, J=6.9 Hz, 3H, 2-Me of syn-isomer), 1.05 (d, J=7.3 Hz, 2-Me of anti-isomer).

4-(3,5-Di-tert-butylphenyl)-2,7-dimethyl-1H-indene

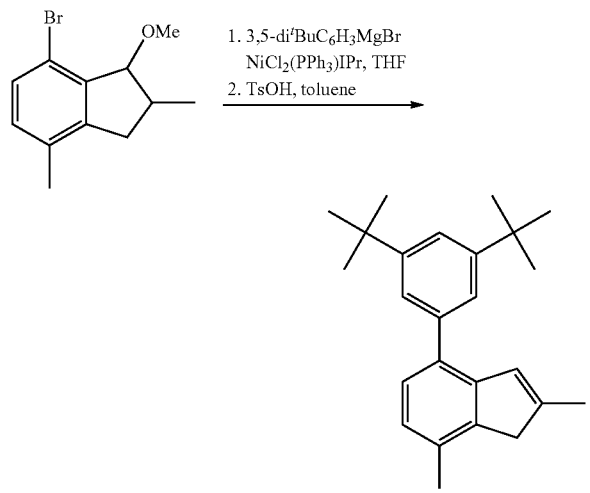

To a solution of 3,5-di-tert-butylphenylmagnesium bromide obtained from 59.0 g (0.219 mol) of 1-bromo-3,5-di-tert-butylbenzene and 9.31 g (0.383 mol, 1.75 eq.) of magnesium turnings in 550 ml of THF 1.0 g (1.28 mmol, 0.71 mol. %) NiCl$_2$(PPh$_3$)IPr and a solution of 46.1 g (0.181 mol) of 7-bromo-1-methoxy-2,4-dimethylindane in 50 ml of THF were added. A moderate reflux occurs approximately after one minute which ceased after the following 30 sec. This mixture was refluxed additionally for 1 h. Finally, 50 ml of water was added, and the main part of THF was distilled off on rotary evaporator. Further on, 500 ml of dichloromethane and 500 ml of 2 M HCl were added to the residue. The organic layer was separated, the aqueous layer was additionally extracted with 100 ml of dichloromethane. The combined organic extract was evaporated to dryness to give a yellowish oil. To a solution of this oil in 700 ml of toluene 0.8 g of TsOH was added. The resulting mixture was refluxed using Dean-Stark head for 20 min, one more portion (0.8 g) of TsOH was added, and the mixture was refluxed for another 20 min. The resulting mixture cooled to room temperature was washed with 200 ml of 10% aqueous NaHCO$_3$. The organic layer was separated, the aqueous layer was additionally extracted with 2×100 ml of dichloromethane. The combined organic extract was evaporated to dryness, a solution of the residue in 500 ml of dichloromethane was passed through a short pad of silica gel 60 (40-63 um) and then evaporated to dryness to give yellowish crystalline material. This crude product was re-crystallization from 200 ml of hot n-hexane. Crystals precipitated from this solution at 5° C. were collected and dried in vacuum. This procedure gave 49.8 g of white microcrystalline product. The mother liquor was evaporated to dryness, and the main part of 1,3-di-tert-butylbenzene was distilled off at elevated temperature on rotary evaporator. The residue was then re-crystallized from 80 ml of n-hexane at −30° C. overnight. This gave additional 6.21 g of the product. Thus, the total yield of 4-(3,5-di-tert-butylphenyl)-2,7-dimethyl-1H-indene was 56.0 g (93%).

Anal. calc. for C$_{25}$H$_{32}$: C, 90.30; H, 9.70. Found: C, 90.44; H, 9.89.

$^1$H NMR (CDCl$_3$): δ (t, J=1.8 Hz, 1H, 4-H in C$_6$H$_3$$^t$Bu$_2$), 7.33 (d, J=1.8 Hz, 2H, 2,6-H in C$_6$H$_3$$^t$Bu$_2$), 7.24 (d, J=7.7 Hz, 1H, 5-H in indenyl), 7.01 (d, J=7.7 Hz, 1H, 6-H in indenyl), 6.67 (m, 1H, 3-H in indenyl), 3.27 (s, 2H, 1-H in indenyl), 2.37 (s, 3H, 7-Me in indenyl), 2.16 (s, 3H, 2-Me in indenyl), 1.37 (s, 18H, $^t$Bu). $^{13}$C {$^1$H} NMR (CDCl$_3$): δ 150.5, 146.0, 143.1, 142.4, 140.2, 133.0, 131.3, 127.2, 126.7, 125.2, 123.3, 120.4, 42.0, 34.9, 31.5, 18.5, 17.0.

A mixture of (2-methyl-4-phenyl-5-methoxy-6-tert-butyl-1H-inden-1-yl)[2,7-dimethyl-4-(3,5-di-tert-butylphenyl)-1H-inden-1-yl]dimethylsilane and (2-methyl-4-phenyl-5-methoxy-6-tert-butyl-1H-inden-1-yl)[2,4-dimethyl-7-(3,5-di-tert-butylphenyl)-1H-inden-1-yl]dimethyl silane

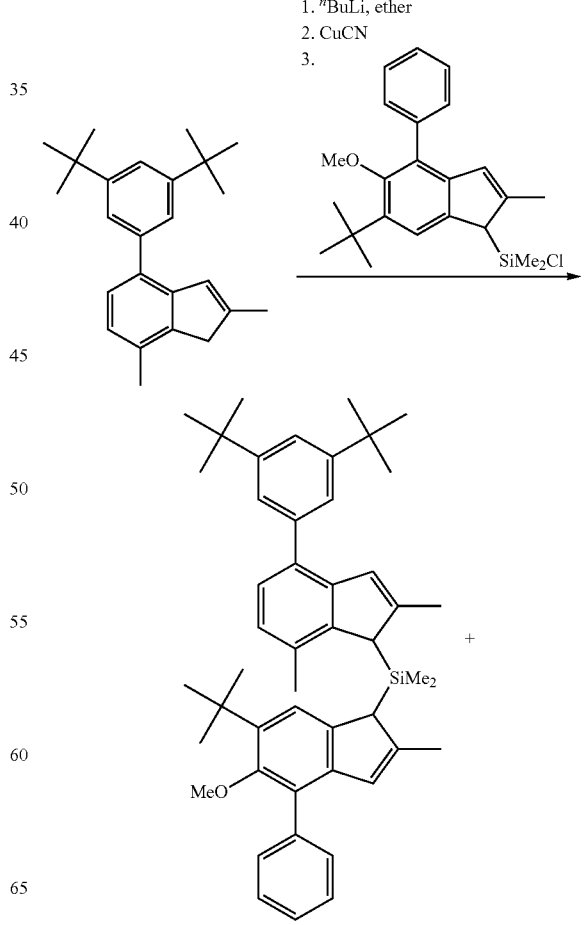

Anti-dimethylsilanediyl(2-methyl-4-phenyl-5-methoxy-6-tert-butyl-indenyl)[2,7-dimethyl-4-(3,5-di-tert-butylphenyl)indenyl]zirconium dichloride (Metallocene E5)

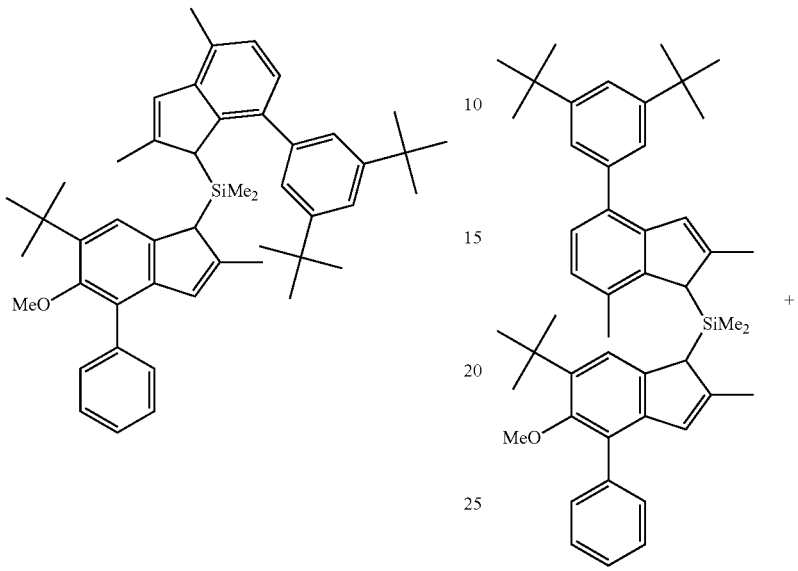

To a solution of 11.4 g (34.3 mmol) of 4-(3,5-di-tert-butylphenyl)-2,7-dimethyl-1H-indene in 200 ml of ether 13.7 ml (34.3 mmol) of 2.5 M $^n$BuLi in hexanes was added in one portion at −40° C. This mixture was stirred overnight at room temperature, then cooled to −40° C., and 200 mg of CuCN was added. The resulting mixture was stirred for 1 h at −20° C., then cooled to −40° C., and a solution 13.2 g (34.3 mmol) of (6-tert-butyl-5-methoxy-2-methyl-4-phenyl-1H-inden-1-yl)(chloro)dimethylsilane in 150 ml of ether was added in one portion. Further on, this mixture was stirred overnight at ambient temperature, and then 0.5 ml of water was added. The formed mixture was filtered through a pad of silica gel 60 (40-63 um) which was additionally washed by dichloromethane. The combined organic elute was evaporated to dryness, and the residue was dried in vacuum. This procedure gave 24.2 g of a ca. 1 to 1 mixture of (6-tert-butyl-5-methoxy-2-methyl-4-phenyl-1H-inden-1-yl)[4-(3,5-di-tert-butylphenyl)-2,7-dimethyl-1H-inden-1-yl]dimethylsilane and (6-tert-butyl-5-methoxy-2-methyl-4-phenyl-1H-inden-1-yl)[7-(3,5-di-tert-butylphenyl)-2,4-dimethyl-1H-inden-1-yl] dimethylsilane (>90% purity on the evidence of NMR spectroscopy) which was further used without an additional purification.

Anal. calc. for $C_{48}H_{60}OSi$: C, 84.65; H, 8.88. Found: C, 84.82; H, 9.15.

$^1$H NMR (CDCl$_3$): δ 7.55-7.28 (m), 7.21-6.93 (m), 6.76 (s), 6.73 (s), 6.71 (s), 6.68 (s), 6.44 (s), 6.41 (s), 6.20 (s), 6.18 (s), 4.42 (s), 4.15 (s), 4.01 (s), 3.79 (s), 3.67 (s), 3.65 (s), 3.24 (s), 3.22 (s), 3.18 (s), 3.16 (s), 2.45 (s), 2.44 (s), 2.36 (s), 2.29 (s), 2.25 (s), 2.23 (s), 2.21 (s), 2.20 (s), 2.12 (s), 2.06 (s), 1.80 (s), 1.61 (s), 1.46 (s), 1.43 (s), 1.39 (s), 1.38 (s), 1.38 (s), 1.33 (s), 1.31 (s), −0.15 (s), −0.18 (s), −0.24 (s), −0.30 (s), −0.37 (s), −0.64 (s), −0.67 (s), −0.71 (s).

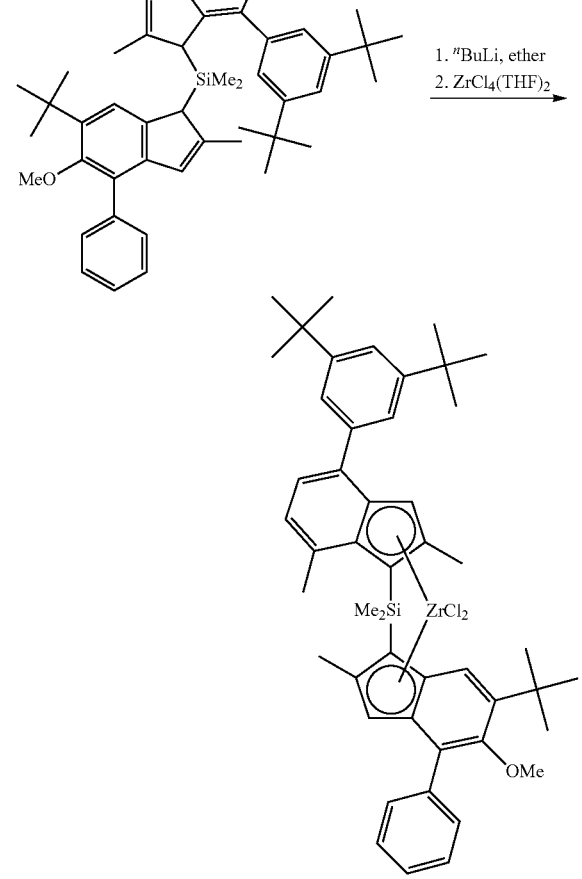

To a solution of 24.2 g (ca. 34.3 mmol, >90% purity) of a mixture of (6-tert-butyl-5-methoxy-2-methyl-4-phenyl-1H- inden-1-yl) [4-(3,5-di-tert-butylphenyl)-2,7-dimethyl-1H-inden-1-yl]dimethylsilane and (6-tert-butyl-5-methoxy-2-methyl-4-phenyl-1H-inden-1-yl)[7-(3,5-di-tert-butylphenyl)-2,4-dimethyl-1H-inden-1-yl]dimethylsilane in 250 ml of ether 28.4 ml (71.0 mmol) of 2.5 M ⁿBuLi in hexanes was added in one portion −30° C. This mixture was stirred overnight at room temperature, then cooled to −40° C., and 13.4 g (35.5 mmol) of ZrCl₄(THF)₂ was added. The resulting mixture was stirred for 24 h, then, the orange precipitate was filtered from red solution through glass frit (G4), the precipitate was washed with 30 ml of ether. On the evidence of NMR spectroscopy, this precipitate includes the desired anti-zirconocene (isomer A), though isomeric complexes A, B, and C in ratio equal to 1:2:2 are in the filtrate. This precipitate was dissolved in 100 ml of hot toluene, and the formed solution was filtered through glass frit (G4) to remove LiCl. The filtrate was evaporated to dryness, and the residue was recrystallized from 40 ml of hot n-octane. Crystals precipitated at room temperature were collected, washed by 15 ml of n-hexane, and dried in vacuum to give 5.72 g of anti-complex. To the mother liquor 5 ml of hexanes was added, the formed solution was heated to reflux. Crystals precipitated from this solution at room temperature were collected and dried in vacuum to give 0.42 g of anti-complex. Crystals precipitated after one week from the above-described filtrate including complexes A, B, and C in ratio equal to 1:2:2 were collected and dried in vacuum to give 4.40 g or red-orange crystalline solid as a ca. 2 to 5 mixture of the isomeric complexes A and B. The mother liquor was evaporated to dryness, the residue was dissolved in 50 ml of hot toluene, then 50 ml of n-hexane was added. Crystals precipitated from this solution at room temperature were collected and dried in vacuum to give 2.70 g of a ca. 2 to 3 mixture of the isomeric complexes A and B. Again, the mother liquor was evaporated to dryness, the residue was re-crystallized from 45 ml of n-hexane-toluene (2:1, vol.). This procedure gave 0.95 g of a ca. 1 to 1.2 mixture of the isomeric complexes A and B. Thus, the overall yield of ansa-zirconocenes was 14.2 g (49%). Assignment in NMR spectra was made using the following abbreviations: $L^1$ for 4-(3,5-di-tert-butylphenyl)-2,7-dimethyl-1H-inden-1-yl and $L^2$ for 6-tert-butyl-5-methoxy-2-methyl-4-phenyl-1H-inden-1-yl.

anti-Zirconocene.

Anal. calc. for $C_{48}H_{58}Cl_2OSiZr$: C, 68.54; H, 6.95. Found: C, 68.48; H, 7.11.

¹H NMR (CDCl₃): δ 7.61-7.57 (m, 2H, 2,6-H in Ph), 7.55 (s, 1H, 7-H in $L^2$), 7.50 (d, 2-H, 2,6-H in $C_6H_3{}^tBu_2$), 7.44-7.40 (m, 3H, 3,5-H in Ph and 4-H in $C_6H_3{}^tBu_2$), 7.32 (m, 1H, 4-H in Ph), 7.30 (d, J=7.1 Hz, 1H, 5-H in $L^1$), 7.05 (s, 1H, 3-H in $L^1$), 6.98 (d, J=7.1 Hz, 6-H in $L^1$), 6.58 (s, 1H, 3-H in $L^2$), 3.39 (s, 3H, OMe), 2.65 (s, 3H, 7-Me in $L^1$), 2.31 (s, 3H, 2-Me in $L^1$), 2.07 (s, 3H, 2-Me in $L^2$), 1.40 (s, 9H, 6-ᵗBu in $L^2$), 1.35 (s, 3H, SiMeMe'), 1.34 (s, 18H, ᵗBu in $C_6H_3{}^tBu_2$), 1.27 (s, 3H, SiMeMe').

Synthesis of anti-dimethylsilanediyl(2-methyl-4-phenyl-5-methoxy-6-tert-butyl-indenyl)(2-methyl-4-(3,5-di-tert-butylphenyl)-7-methoxy-inden-1-yl)zirconium dichloride (Metallocene E6)

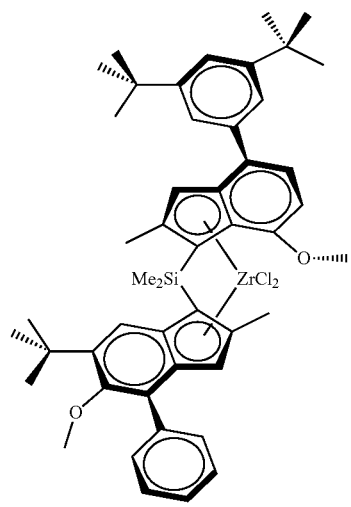

1-Bromo-2-(bromomethyl)-4-methoxybenzene

Method 1

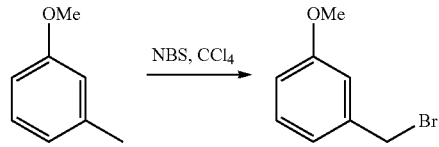

1-(Bromomethyl)-3-methoxybenzene

To a solution of 122 g (1.0 mol) of 1-methoxy-3-methylbenzene in 900 ml of CCl4, 178 g (1.0 mol) of NBS and 1.0 g of (PhCO2)2 were added at room temperature. This mixture was refluxed for 3 h, cooled to room temperature, and the formed succinimide was filtered off. Succinimide was additionally washed by 2×150 ml of CCl4. The combined filtrate was evaporated to dryness, and the residue was distilled in vacuum, b.p. 112-125° C./8 mm Hg. This procedure gave 152.5 g of 1-(bromomethyl)-3-methoxybenzene contaminated with ca. 25% of the isomeric product, i.e. 1-bromo-4-methoxy-2-methylbenzene.

Anal. calc. for $C_8H_9BrO$: C, 47.79; H, 4.51. Found: C, 47.93; H, 4.65.

¹H NMR (CDCl₃): δ 7.26 (m, 1H, 5-H), 6.98 (m, 1H, 6-H), 6.94 (m, 1H, 2-H), 6.85 (m, 1H, 4-H), 4.47 (s, 2H, $CH_2Br$), 3.81 (s, 3H, OMe).

1-Bromo-2-(bromomethyl)-4-methoxybenzene

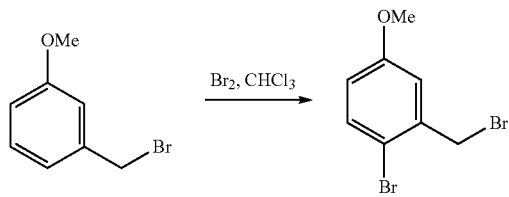 [SMILES: COc1cccc(CBr)c1 ; COc1ccc(Br)c(CBr)c1]

To a solution of above-described crude 1-(bromomethyl)-3-methoxybenzene (152.5 g) in 1 L of chloroform a solution of 134 g (0.841 mol) of bromine in 200 ml of chloroform was added dropwise by vigorous stirring at room temperature. The reaction mixture was stirred overnight at ambient temperature and then evaporated to dryness. The residue was triturated with 1000 ml of n-hexane, and the precipitate was filtered off, washed with 100 ml of n-hexane, and then dried in vacuum. An additional amount of the product was obtained by evaporation of mother liquor followed by treatment of the residue with 200 ml of n-hexane. In total, this procedure gave 153 g (55% overall yield for two stages) of 1-bromo-2-(bromomethyl)-4-methoxybenzene. (average of two runs)

Anal. calc. for $C_8H_8Br_2O$: C, 34.32; H, 2.88. Found: C, 34.30; H, 3.01.

$^1$H NMR (CDCl$_3$): δ 4.48 (d, J=8.8 Hz, 1H, 6-H), 7.02 (d, J=3.0 Hz, 1H, 3-H), 6.76 (dd, J=8.8 Hz, J=3.0 Hz, 1H, 5-H), 4.58 (s, 2H, CH$_2$Br), 3.83 (s, 3H, OMe).

Method 2

1-Bromo-4-methoxy-2-methylbenzene

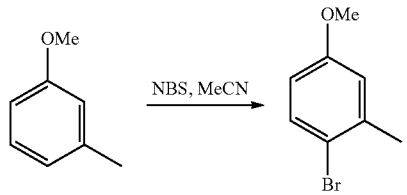

To a solution of 122 g (1.0 mol) of 1-methoxy-3-methylbenzene in 1 L of acetonitrile 178 g (1.0 mol) of NBS was added in small portions by vigorous stirring for 1 h at 10° C. The reaction mixture was stirred at ambient temperature overnight and then evaporated to dryness. The residue was dissolved in 1 L of n-hexane and filtered through glass frit (G2). The precipitate was additionally washed by 2×150 ml of n-hexane. The combined filtrate was evaporated to dryness to give 173 g (86%) of 1-bromo-4-methoxy-2-methylbenzene.

Anal. calc. for $C_8H_9BrO$: C, 47.79; H, 4.51. Found: C, 47.83; H, 4.69.

$^1$H NMR (CDCl$_3$): δ 7.43 (d, J=8.8 Hz, 1H, 6-H), 6.82 (d, J=2.9 Hz, 1H, 3-H), 6.64 (dd, J=8.8 Hz, J=2.9 Hz, 1H, 5-H), 3.80 (s, 3H, OMe), 2.40 (s, 3-H, 2-Me).

1-Bromo-2-(bromomethyl)-4-methoxybenzene

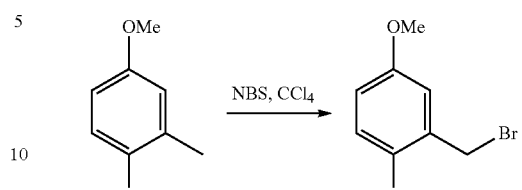

To a solution of 173 g (0.86 mol) of 1-bromo-4-methoxy-2-methylbenzene in 850 ml of CCl$_4$ 153 g (0.86 mol) of NBS and 1.0 g of (PhCOO)$_2$ were added at room temperature. This mixture was refluxed for 16 h, cooled to room temperature, and then filtered through glass frit (G2). The precipitate was additionally washed by 2×150 ml of CCl$_4$. The combined filtrate was evaporated to dryness, and the residue was triturated with 600 ml of n-hexane. The precipitate was filtered off (G3 glass frit), washed by 50 ml of n-hexane, and dried in vacuum. This procedure gave 121 g of the title product. Additional amount of the product was obtained by evaporation of a mother liquor followed by crystallization of the residue from 200 ml of n-hexane at −25° C. In total, 157 g (65%; or 56% overall yield for two stages) of 1-bromo-2-(bromomethyl)-4-methoxybenzene has been isolated.

Anal. calc. for $C_8H_8Br_2O$: C, 34.32; H, 2.88. Found: C, 34.44; H, 2.95.

Method 3

1-Bromo-2-(bromomethyl)-4-methoxybenzene

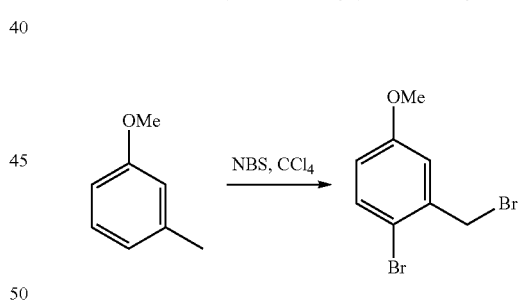

N-Bromosuccinimide (45.9 g) was added to a solution of 15.1 g (123 mmol) of 3-methylanisole in 240 ml of tetrachloromethane. The mixture was refluxed for 14 h with 0.3 g of benzoyl peroxide. The resulting mixture was filtered through glass frit (G3), to the filtrate 100 ml of dichloromethane and 300 ml of cold water were added. The organic layer was separated, dried over Na$_2$SO$_4$, and then evaporated to dryness. The residue was re-crystallized from hot hexanes to give 16.0 g of the title compound. The mother liquor was evaporated to dryness, and the residue was recrystallized from hexanes to give additional 6.1 g of the title material. Total yield 22.1 g (64%) of a white crystalline solid.

Anal. calc. for $C_8H_8Br_2O$: C, 34.32; H, 2.88. Found: C, 34.47; H, 3.02.

3-(2-Bromo-5-methoxyphenyl)-2-methylpropanoic acid

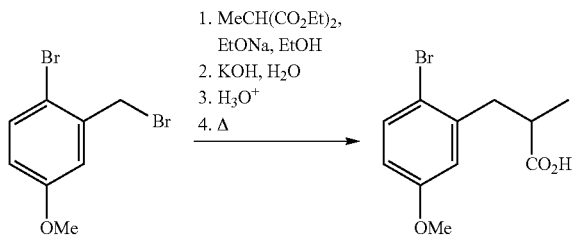

To a solution of sodium ethoxide obtained from 15.2 g (0.661 mol) of sodium and 540 ml of dry ethanol 115 g (0.658 mol) of diethyl methylmalonate was added. This mixture was stirred for 15 min; then, 184 g (0.659 mol) of 1-bromo-2-(bromomethyl)-4-methoxybenzene was added with vigorous stirring at such a rate to maintain gentle reflux. This mixture was refluxed for an additional 2 h and then cooled to room temperature. A solution of 130 g of KOH in 400 ml of water was added. The resulting mixture was refluxed for 4 h to saponificate the formed ester. Ethanol and water were distilled off until the vapor temperature reached 95° C. To the residue cooled to room temperature 1500 ml of water and then 12 M HCl (to pH 1) were added. The formed precipitate of (2-bromo-5-methoxybenzyl)(methyl)malonic acid was filtered off, washed with 2×200 ml of cold water, and dried on air. Decarboxylation of the substituted methylmalonic acid at 180° C. gave 152 g (84%) of the title product.

Anal. calc. for $C_{11}H_{13}BrO_3$: C, 48.37; H, 4.80. Found: C, 48.21; H, 4.92.

$^1$H NMR (CDCl$_3$): δ 7.45 (d, J=8.8 Hz, 1H, 3-H in aryl), 6.82 (d, J=3.0 Hz, 1H, 6-H in aryl), 6.69 (dd, J=8.8 Hz, J=3.0 Hz, 1H, 4-H in aryl), 3.79 (s, 3H, OMe), 3.17 (dd, J=13.6 Hz, J=7.1 Hz, 1H, CHH'CH), 2.94 (m, 1H, CHMe), 2.82 (dd, J=13.6 Hz, J=7.5 Hz, 1H, CHH'CH), 1.26 (d, J=7.1 Hz, 3H, CHMe).

4-Bromo-7-methoxy-2-methylindan-1-one

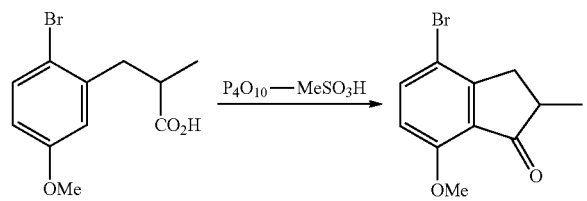

To Eaton's reagent obtained from 153 g of P$_4$O$_{10}$ and 780 ml of MeSO$_3$H 149 g (0.544 mol) of 3-(2-bromo-5-methoxyphenyl)-2-methylpropanoic acid was added by vigorous stirring for 50 min at 60-62° C. The resulting mixture was additionally stirred for 30 min at the same temperature and then poured in a mixture of 2 kg of ice and 2000 cm$^3$ of cold water. The crude product was extracted with 800 ml of dichloromethane, the aqueous layer was then additionally extracted with 2×200 ml of dichloromethane per each 2 L of the aqueous phase. The combined organic extract was washed by aqueous K$_2$CO$_3$, dried over K$_2$CO$_3$, and then evaporated to dryness. The resulting red oil was distilled in vacuum at 155-170° C./5 mm Hg to yield 104 g (75%) of 4-bromo-7-methoxy-2-methylindan-1-one as yellow oil which crystallizes slowly at room temperature.

Anal. calc. for $C_{11}H_{11}BrO_2$: C, 51.79; H, 4.35. Found: C, 51.84; H, 4.40.

$^1$H NMR (CDCl$_3$): δ 7.64 (d, J=8.6 Hz, 1H, 5-H), 6.73 (d, J=8.6 Hz, 1H, 6-H), 3.94 (s, 3H, OMe), 3.27 (dd, J=17.7 Hz, J=8.1 Hz, 1H, CHH'CH), 2.70 (m, 1H, CHMe), 2.59 (dd, J=17.7 Hz, J=3.9 Hz, 1H, CHH'CH), 1.31 (d, J=7.5 Hz, 3H, 2-Me).

4-Bromo-1,7-dimethoxy-2-methylindane

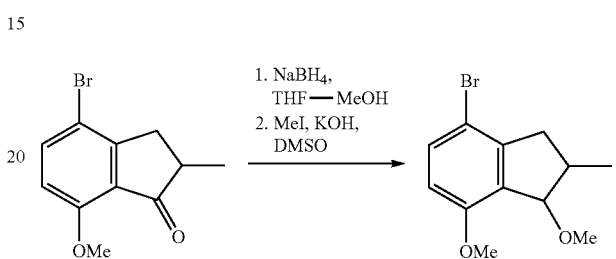

To a mixture of 104 g (0.407 mmol) of 4-bromo-7-methoxy-2-methylindan-1-one and 15.0 g (0.397 mmol) of NaBH$_4$ in a mixture of 410 ml of THF 205 ml of methanol was added dropwise with vigorous stirring for 4 h at +5° C. This mixture was stirred overnight at room temperature and then added to 1 liter of cold water. The resulting mixture was carefully acidified by 2 M HCl to pH 5.0, and the formed indan-1-ol was extracted with 500 ml of dichloromethane. The aqueous layer was additionally extracted with 2×200 ml of dichloromethane. The combined organic extract was evaporated to dryness. To the resulting yellowish liquid of the crude 4-bromo-7-methoxy-2-methylindan-1-ol 800 ml of DMSO, 92.0 g (1.64 mol, 4.0 eq) of KOH, and 116 g (0.817 mol, 2.0 eq) of MeI were added. This mixture was stirred for 3 h at ambient temperature and then added to 3 L of cold water. The crude product was extracted with dichloromethane (500 ml, then 3×250 ml). The combined organic extract was washed 5 times by 1 liter of water and then evaporated to dryness. The product was isolated by flash chromatography on silica gel 60 (40-63 μm; eluent: hexanes-dichloromethane=2:1, then 1:2 and, finally, 1:5, vol.) followed by rectification in vacuum, 149-154° C./8 mm Hg. Yield 96.0 g (87%) of a ca. 1 to 2 mixture of two diastereomers.

Anal. calc. for $C_{12}H_{15}BrO_2$: C, 53.15; H, 5.58. Found: C, 53.08; H, 5.65.

$^1$H NMR (CDCl$_3$), major diastereomer: δ 7.36 (d, J=8.6 Hz, 1H, 5-H), 6.62 (d, J=8.6 Hz, 1H, 6-H), 4.68 (d, J=1.3 Hz, 1H, CHOMe), 3.82 (s, 3H, 7-OMe), 3.38 (s, 3H, 1-OMe), 3.27 (dd, J=16.7 Hz, J=7.3 Hz, 1H, 3-H), 2.54 (m, 1H, 2-H), 2.41 (dd, J=16.7 Hz, J=2.0 Hz, 1H, 3'-H), 1.03 (d, J=7.3 Hz, 3H, 2-Me); minor diastereomer: δ 7.33 (d, J=8.6 Hz, 1H, 5-H), 6.61 (d, J=8.6 Hz, 1H, 6-H), 4.69 (d, J=5.6 Hz, 1H, CHOMe), 3.81 (s, 3H, 7-OMe), 3.38 (s, 3H, 1-OMe), 3.27 (dd, J=16.0 Hz, J=7.8 Hz, 1H, 3-H), 2.41 (dd, J=16.0 Hz, J=9.6 Hz, 1H, 3'-H), 2.54 (m, 1H, 2-H), 1.22 (d, J=6.9 Hz, 3H, 2-Me).

2-Methyl-4-methoxy-7-(3,5-di-tert-butylphenyl)-1H-indene

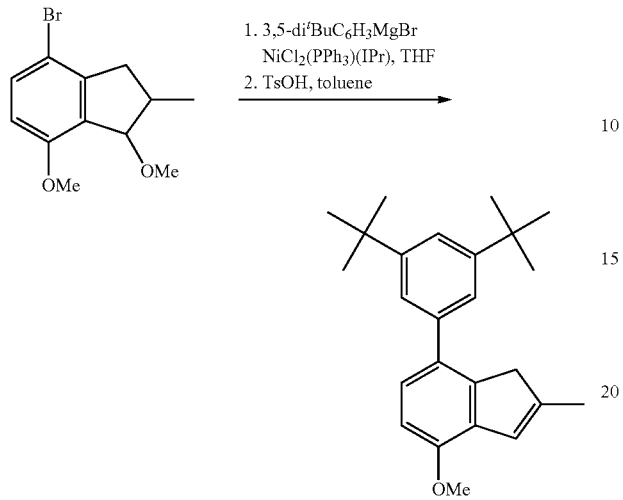

To a solution of 3,5-di-tert-butylphenylmagnesium bromide obtained from 59.3 g (0.220 mol) of 1-bromo-3,5-di-tert-butylbenzene and 7.60 g (0.313 mol, 1.42 eqv.) of magnesium turnings in 450 ml of THF 1.00 g (1.28 mmol, 0.65 mol. %) NiCl$_2$(PPh$_3$)IPr and a solution of 53.4 g (0.197 mol) of 4-bromo-1,7-dimethoxy-2-methylindane in 50 ml of THF were added. A vigorous reflux occurs approximately after ca. 30 sec and ceased after the following 30 sec. This mixture was stirred for 30 min at room temperature. Finally, 1000 ml of water and then 50 ml of 12 M HCl were added. The product was extracted with 500 ml of dichloromethane, organic layer was separated, the aqueous layer was additionally extracted with 200 ml of dichloromethane. The combined organic extract was dried over K$_2$CO$_3$, passed through a short column with silica gel 60 (40-63 um), and then evaporated to dryness. To the residue dissolved in 700 ml of toluene 1.4 g of TsOH was added. This solution was refluxed using Dean-Stark head for 20 min, cooled to room temperature, washed with 200 ml of 10% aqueous NaHCO$_3$. The organic layer was separated, the aqueous layer was extracted with 2×100 ml of dichloromethane. The combined organic solution was evaporated to dryness. The product was isolated by flash chromatography on silica gel 60 (40-63 um; eluent: hexane-dichloromethane=10:1, then 1:1, vol.). This procedure gave 67.6 g (99%) of 2-methyl-4-methoxy-7-(3,5-di-tert-butylphenyl)-1H-indene as a yellowish crystalline powder. The latter can be recrystallized from n-hexane with marginal loss of weight.

Anal. calc. for C$_{25}$H$_{32}$O: C, 86.15; H, 9.25. Found: C, 86.09; H, 9.23.

$^1$H NMR (CDCl$_3$): δ 7.40 (m, 1H, 4-H in tBu$_2$C$_6$H$_3$), 7.35 (m, 2H, 2,6-H in tBu$_2$C$_6$H$_3$), 7.15 (d, J=8.4 Hz, 1H, 6-H in indenyl), 6.88 (d, J=8.4 Hz, 1H, 5-H in indenyl), 6.70 (m, 1H, 3-H in indenyl), 3.92 (s, 3H, OMe), 3.41 (m, 2H, 2,2'-H in indenyl), 2.15 (s, 3H, 2-Me in indenyl), 1.38 (s, 18H, $^t$Bu).

Chloro[4-(3,5-di-tert-butylphenyl)-7-methoxy-2-methyl-1H-inden-1-yl]dimethylsilane

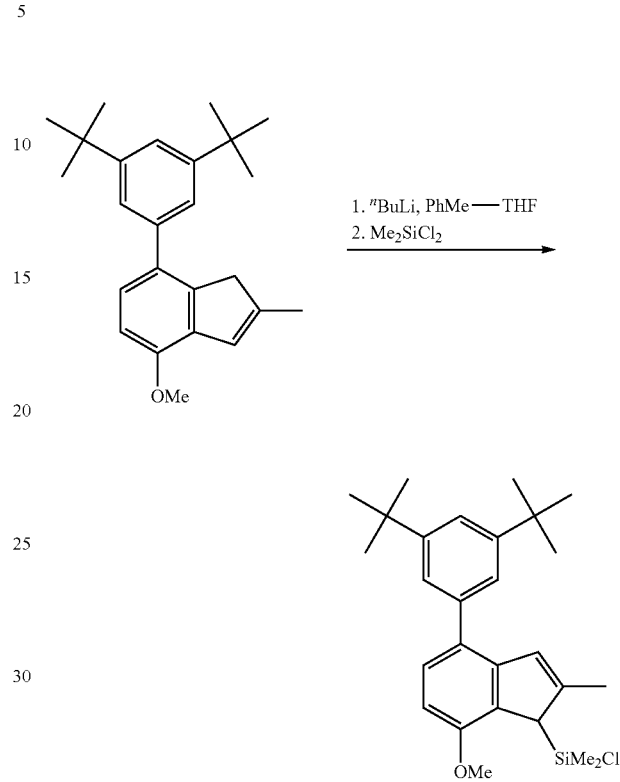

To a solution of 13.1 g (37.5 mmol) of 7-(3,5-di-tert-butylphenyl)-4-methoxy-2-methyl-1H-indene in 200 ml of toluene 15.0 ml (37.5 mmol) of 2.5 M $^n$BuLi in hexanes was added at room temperature. The resulting viscous solution was stirred for 2 h, and then 10 ml of THF was added. The formed suspension was stirred for 12 h at room temperature, ca. 2 h at 60° C., cooled to −20° C., and 24.0 g (0.186 mol, 5 eq) of dichlorodimethylsilane was added in one portion. The resulting solution was warmed to room temperature, stirred for 2 h at this temperature, evaporated to ca. ½ of its volume, and then filtered through glass frit (G3). The precipitate was additionally washed by 2×30 ml of toluene. The combined filtrate was evaporated to dryness to give a viscous yellowish oil which contained ca. 90% of chloro[4-(3,5-di-tert-butylphenyl)-7-methoxy-2-methyl-1H-inden-1-yl]dimethylsilane. This product was further used without an additional purification.

Anal. calc. for C$_{27}$H$_{37}$ClOSi: C, 73.51; H, 8.45. Found: C, 73.70; H, 8.57.

$^1$H NMR (CDCl$_3$): δ 7.41 (m, 1H, 4-H in tu$_2$C$_6$H$_3$), 7.34 (m, 2H, 2,6-H in tu$_2$C$_6$H$_3$), 7.29 (d, J=8.5 Hz, 1H, 6-H in indenyl), 6.76 (m, 1H, 3-H in indenyl), 6.74 (d, J=8.5 Hz, 1H, 5-H in indenyl), 3.89 (s, 3H, OMe), 3.84 (s, 1H, 1-H in indenyl), 2.31 (s, 3H, 2-Me in indenyl), 1.40 (s, 18H, tu), 0.64 (s, 3H, SiMeMe'Cl), 0.01 (s, 3H, SiMeMe'Cl).

[2-Methyl-4-phenyl-5-methoxy-6-tert-butyl-1H-inden-1-yl]-[2-methyl-4-(3,5-di-tertbutylphenyl)-7-methoxy-1H-inden-1-yl]dimethylsilane

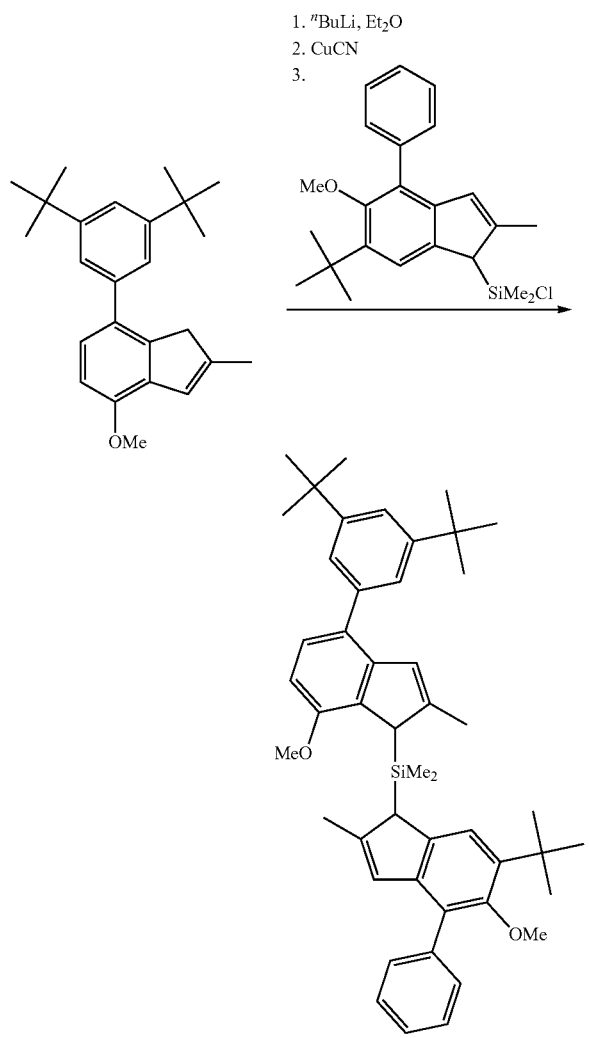

To a solution of 12.3 g (35.3 mmol) of 7-(3,5-di-tert-butylphenyl)-4-methoxy-2-methyl-1H-indene in 200 ml of ether 14.2 ml (35.5 mmol) of 2.5 M nBuLi in hexanes was added in one portion at −50° C. This mixture was stirred overnight at room temperature, then cooled to −40° C., and 150 mg of CuCN was added. The resulting mixture was stirred for 1 h at −20° C., then cooled to −40° C., and a solution of 13.6 g (35.3 mmol) of (2-methyl-4-phenyl-5-methoxy-6-tert-butyl-1H-inden-1-yl)(chloro)dimethylsilane in 200 ml of ether was added in one portion. Further on, this mixture was stirred overnight at ambient temperature, then 0.5 ml of water was added. This solution was filtered through a pad of silica gel 60 (40-63 um) which was additionally washed by dichloromethane. The combined organic elute was evaporated to dryness and dried in vacuum. This procedure gave 24.9 g of a yellowish glass. This product of ca. 90% purity was further used without an additional purification.

Anal. calc. for $C_{48}H_{60}O_2Si$: C, 82.70; H, 8.68. Found: C, 83.07; H, 8.80.

$^1$H NMR (CDCl$_3$): δ 7.70 (s), 7.29-7.55 (m), 6.72-6.81 (m), 6.49 (m), 6.43 (m), 4.07 (s), 3.95 (s), 3.94 (s), 3.89 (s), 3.88 (s), 3.95 (s), 3.84 (s), 3.28 (s), 3.26 (s), 2.33 (s), 2.20 (s), 2.12 (s), 1.99 (s), 1.49 (s), 1.45 (s), 1.43 (s), 1.42 (s), −0.13 (s), −0.15 (s), −0.23 (s), −0.31 (s).

Anti-dimethylsilanediyl(2-methyl-4-(3,5-di-tert-butylphenyl)-7-methoxy-inden-1-yl)(2-methyl-4-phenyl-5-methoxy-6-tert-butyl-inden-1-yl) zirconium dichloride (Metallocene E6)

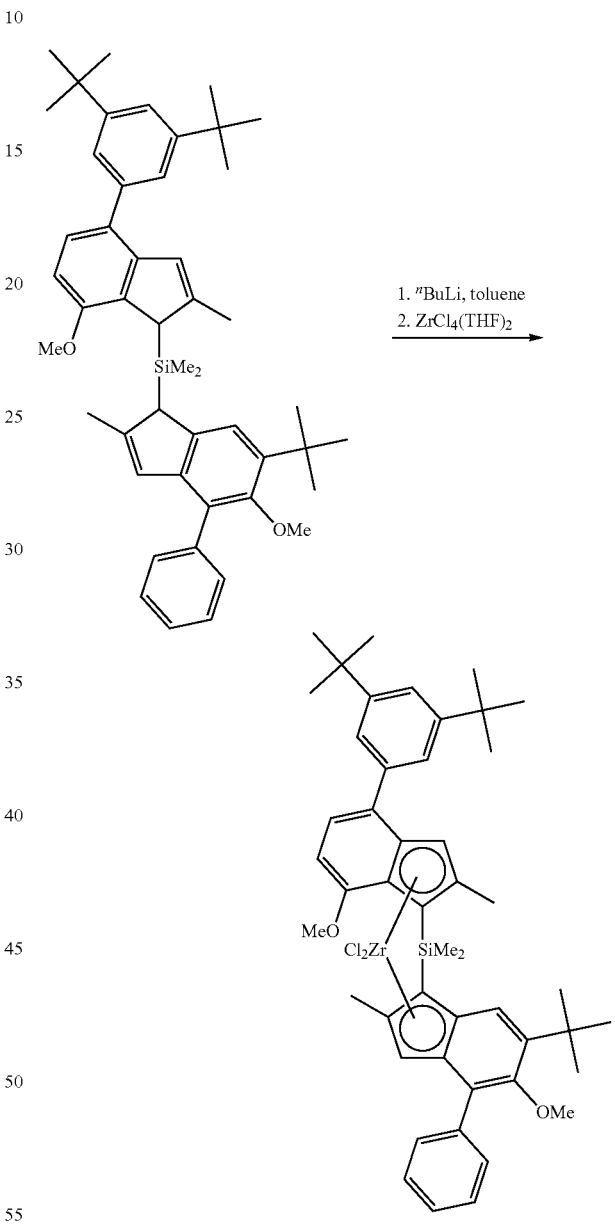

To a solution of 24.9 g (ca. 35.3 mmol, ca. 90% purity) of [6-tert-butyl-5-methoxy-2-methyl-4-phenyl-1H-inden-1-yl][4-(3,5-di-tert-butylphenyl)-7-methoxy-2-methyl-1H-inden-1-yl]dimethylsilane in 300 ml of toluene 28.3 ml (70.8 mmol) of 2.5 M nBuLi in hexanes was added in one portion at room temperature. This mixture was stirred overnight at room temperature, then cooled to −25° C., and 13.3 g (35.3 mmol) of ZrCl$_4$(THF)$_2$ was added. The resulting mixture was stirred for 24 h, then 20 ml of THF was added, and the reaction mixture was stirred 2 h at 60° C. After evaporation of ca. 50 ml of the solvents, the resulting solution warmed to 80° C. was filtered through glass frit (G4) to give a solution of a ca. 1 to 1 mixture of anti- and syn-zirconocenes. This solution was evaporated to dryness. The residue was dissolved in a mixture of 60 ml of toluene and 10 ml of n-octane at reflux. Orange crystals precipitated from this solution at room temperature were filtered off (G3), washed by 3×10 ml of cold toluene (This led to a marked decrease in the amount of precipitate on the filter), 3×10 ml of cold n-hexane, and dried in vacuum. This procedure gave 6.12 g (20%) of pure anti-zirconocene. Red crystals precipitated from the combined mother liquor at room temperature after standing of this solution for a week were filtered off, washed by 3×10 ml of cold toluene, 3×10 ml of cold n-hexane, and dried in vacuum. This procedure gave 2.72 g of pure syn-zirconocene. The mother liquor was diluted with some n-hexane. Crystals precipitated from this solution were collected and treated as described above. This procedure was repeated three times in total to give additional amount of pure syn-zirconocene. Thus, 8.32 g (28%) of pure syn-zirconocene was isolated in total.

Anti-complex:

Anal. calc. for $C_{48}H_{58}Cl_2O_2SiZr$: C, 67.26; H, 6.82. Found: C, 67.40; H, 6.93.

$^1$H NMR (CDCl$_3$): δ 7.59 (br.s, 2H, 2,6-H in Ph), 7.57 (s, 1H, 7-H in 2-methyl-4-phenyl-5-methoxy-6-tert-butylindenyl), 7.47 (d, J=1.8 Hz, 2H, 2,6-H in 3,5-tBu$_2$C$_6$H$_3$), 7.43 (m, 2H, 3,5-H in Ph), 7.88 (t, J=1.8 Hz, 1H, 4-H in 3,5-tBu$_2$C$_6$H$_3$), 7.33 (d, J=7.8 Hz, 1H, 5-H in 2-methyl-4-aryl-7-methoxyindenyl), 7.32 (m, 1H, 4-H in Ph), 6.97 (s, 1-H, 3-H in 2-methyl-4-aryl-7-methoxyindenyl), 6.55 (s, 1-H, 3-H in 2-methyl-4-phenyl-5-methoxy-6-tert-butylindenyl), 6.39 (d, J=7.8 Hz, 1H, 6-H in 2-methyl-4-aryl-7-methoxyindenyl), 3.88 (s, 3H, OMe in 2-methyl-4-phenyl-5-methoxy-6-tert-butylindenyl), 3.39 (s, 3H, OMe in 2-methyl-4-aryl-7-methoxyindenyl), 2.26 (s, 3H, 2-Me in 2-methyl-4-phenyl-5-methoxy-6-tert-butylindenyl), 2.04 (s, 3H, 2-Me in 2-methyl-4-aryl-7-methoxyindenyl), 1.40 (s, 9H, tBu in 2-methyl-4-phenyl-5-methoxy-6-tert-butylindenyl), 1.35 (s, 18H, $^t$Bu in 3,5-tBu$_2$C$_6$H$_3$), 1.30 (s, 3H, SiMeMe'), 1.18 (s, 3H, SiMeMe').

Syn-complex:

Found: C, 67.33; H, 6.90.

$^1$H NMR (CDCl$_3$): δ 7.70 (s, 1H, 7-H in 2-methyl-4-phenyl-5-methoxy-6-tertbutylindenyl), 7.59 (br.s, 2H, 2,6-H in Ph), 7.50 (d, J=1.8 Hz, 2H, 2,6-H in 3,5-tBu$_2$C$_6$H$_3$), 7.43 (m, 2H, 3,5-H in Ph), 7.36 (t, J=1.8 Hz, 1H, 4-H in 3,5-tBu$_2$C$_6$H$_3$), 7.32 (m, 1H, 4-H in Ph), 7.17 (d, J=7.8 Hz, 1H, 5-H in 2-methyl-4-aryl-7-methoxyindenyl), 6.94 (s, 1-H, 3-H in 2-methyl-4-aryl-7-methoxyindenyl), 6.54 (s, 1-H, 3-H in 2-methyl-4-phenyl-5-methoxy-6-tertbutylindenyl), 6.33 (d, J=7.8 Hz, 1H, 6-H in 2-methyl-4-aryl-7-methoxyindenyl), 3.99 (s, 3H, OMe in 2-methyl-4-phenyl-5-methoxy-6-tert-butylindenyl), 3.19 (s, 3H, OMe in 2-methyl-4-aryl-7-methoxy-indenyl), 2.44 (s, 3H, 2-Me in 2-methyl-4-phenyl-5-methoxy-6-tertbutylindenyl), 2.41 (s, 3H, 2-Me in 2-methyl-4-aryl-7-methoxyindenyl), 1.35 (s, 18H, $^t$Bu in 3,5-tBu$_2$C$_6$H$_3$), 1.32 (s, 3H, SiMeMe'), 1.30 (s, 9H, $^t$Bu in 2-methyl-4-phenyl-5-methoxy-6-tertbutylindenyl), 1.20 (s, 3H, SiMeMe').

Synthesis of anti-dimethylsilanediyl[2-methyl-4-(4-tert-butylphenyl)-inden-1-yl][2-methyl-4-(4-tert-butylphenyl)-5-methoxy-6-tert-butyl-inden-1-yl] zirconium dichloride (Metallocene E7)

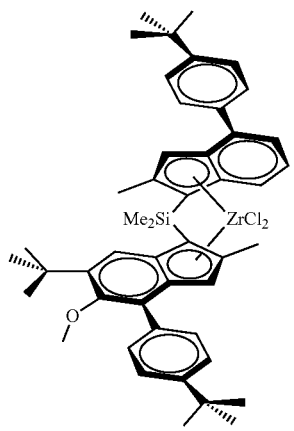

6-tert-Butyl-4-(4-tert-butylphenyl)-5-methoxy-2-methylindan-1-one

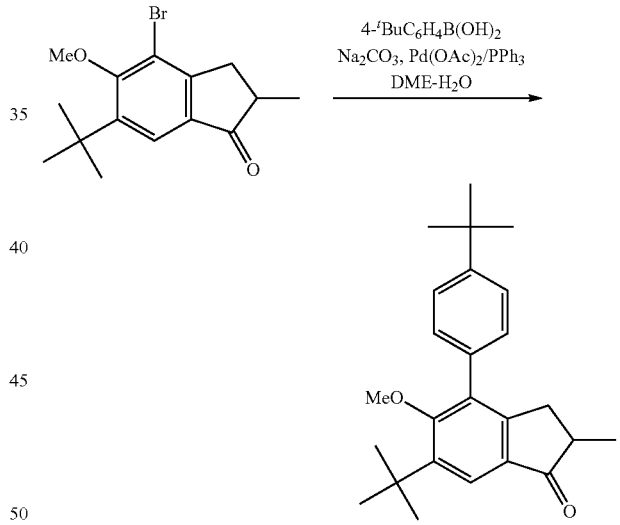

A mixture of 31.1 g (100 mmol) of 4-bromo-6-tertbutyl-5-methoxy-2-methylindanone, 25.0 g (140 mmol) of 4-tert-butylphenylboronic acid, 29.4 g (280 mmol) of Na$_2$CO$_3$, 1.35 g (6.00 mmol, 6 mol. %) of Pd(OAc)$_2$, and 3.15 g (12.0 mmol, 12 mol. %) of PPh$_3$ in 130 ml of water and 380 ml of DME was refluxed for 6 h in argon atmosphere. The formed mixture was evaporated to dryness. To the residue 500 ml of dichloromethane and 500 ml of water were added. The organic layer was separated, the aqueous layer was additionally extracted with 100 ml of dichloromethane. The combined organic extract was dried over Na$_2$SO$_4$, evaporated to dryness, and the crude product was isolated using flash chromatography on silica gel 60 (40-63 um; eluent: hexanes-dichloromethane=2:1, vol.). This crude product was recrystallized from n-hexane to give 29.1 g (81%) of a white solid.

Anal. calc. for C$_{25}$H$_{32}$O$_2$: C, 82.37; H, 8.85. Found: C, 82.26; H, 8.81.

$^1$H NMR (CDCl$_3$): δ 7.74 (s, 1H, 7-H in indenyl), 7.48 (d, J=8.0 Hz, 2H, 2,6-H in C$_6$H$_4$$^t$Bu), 7.33 (d, J=8.0 Hz, 2H, 3,5-H in C$_6$H$_4$$^t$Bu), 3.27 (s, 3H, OMe), 3.15 (dd, J=17.3 Hz, J=7.7 Hz, 1H, 3-H in indan-1-on), 2.67-2.59 (m, 1H, 2-H in indan-1-on), 2.48 (dd, J=17.3 Hz, J=3.7 Hz, 3'-H in indan-1-on), 1.42 (s, 9H, $^t$Bu in C$_6$H$_4$$^t$Bu), 1.38 (s, 9H, 6-$^t$Bu in indan-1-on), 1.25 (d, J=7.3 Hz, 3H, 2-Me in indan-1-one).

5-tert-Butyl-7-(4-tert-butylphenyl)-6-methoxy-2-methyl-1H-indene

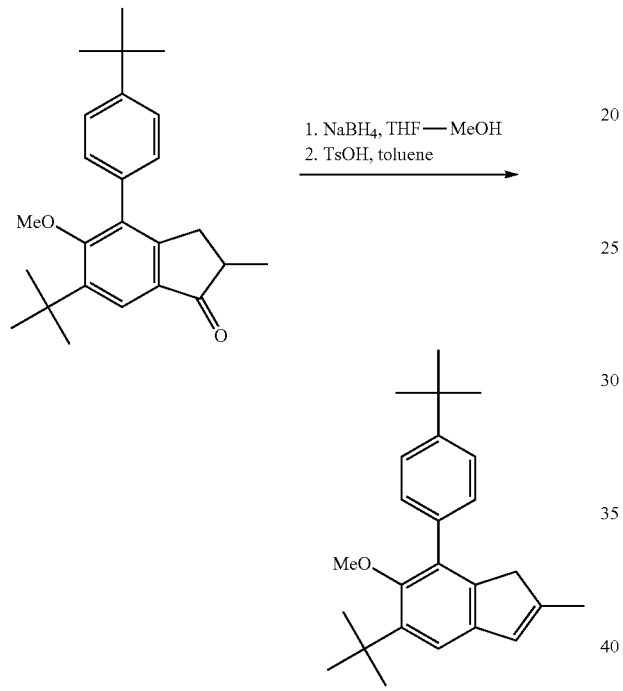

To a solution of 28.9 g (79.2 mmol) of 6-tert-butyl-4-(4-tert-butylphenyl)-5-methoxy-2-methylindan-1-one in 400 ml of THF cooled to 5° C. 5.00 g (132 mmol) of NaBH$_4$ was added. Further on, 100 ml of methanol was added dropwise to this mixture by vigorous stirring for ca. 7 h at 5° C. The resulting mixture was evaporated to dryness, and the residue wad partitioned between 500 ml of dichloromethane and 1000 ml of 0.5 M HCl. The organic layer was separated, the aqueous layer was additionally extracted with 100 ml of dichloromethane. The combined organic extract was evaporated to dryness to give a colorless oil. To a solution of this oil in 500 ml of toluene 1.0 g of TsOH was added. The formed mixture was refluxed with Dean-Stark head for 15 min and then cooled to room temperature using water bath. The resulting reddish solution was washed by 10% aqueous Na$_2$CO$_3$, the organic layer was separated, the aqueous layer was extracted with 2×100 ml of dichloromethane. The combined organic extract was dried over K$_2$CO$_3$ and then passed through short pad of silica gel 60 (40-63 um). The silica gel pad was additionally washed by 50 ml of dichloromethane. The combined organic elute was evaporated to dryness to give a yellowish crystalline mass. The product was isolated by re-crystallization of this mass from 150 ml of hot n-hexane. Crystals precipitated at 5° C. were collected dried in vacuum. This procedure gave 23.8 g of white macrocrystalline 5-tert-butyl-7-(4-tert-butylphenyl)-6-methoxy-2-methyl-1H-indene. The mother liquor was evaporated to dryness and the residue was recrystallized from 20 ml of hot n-hexane in the same way. This procedure gave additional 2.28 g of the product. Thus, the total yield of the title product was 26.1 g (95%).

Anal. calc. for C$_{25}$H$_{32}$O: C, 86.15; H, 9.25. Found: C, 86.24; H, 9.40.

$^1$H NMR (CDCl$_3$): δ 7.44 (d, J=8.5 Hz, 2H, 2,6-H in C$_6$H$_4$$^t$Bu), 7.40 (d, J=8.5 Hz, 2H, 3,5-H in C$_6$H$_4$$^t$Bu), 7.21 (s, 1H, 4-H in indenyl), 6.43 (m, 1H, 3-H in indenyl), 3.20 (s, 3H, OMe), 3.15 (s, 2H, 1-H in indenyl), 2.05 (s, 3H, 2-Me in indenyl), 1.43 (s, 9H, 5-$^t$Bu in indenyl), 1.37 (s, 9H, $^t$Bu in C$_6$H$_4$$^t$Bu).

[6-tert-Butyl-4-(4-tert-butylphenyl)-5-methoxy-2-methyl-1H-inden-1-yl](chloro)dimethylsilane

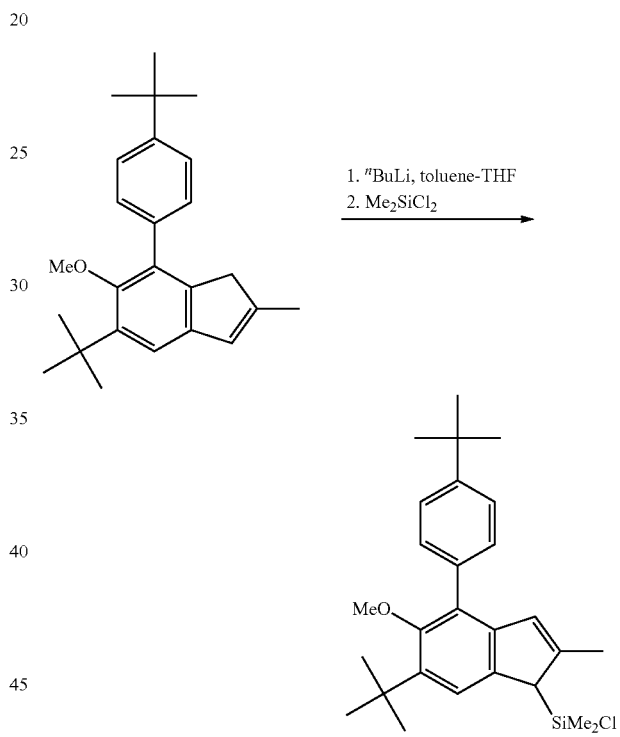

To a solution of 10.5 g (30.0 mmol) of 5-tert-butyl-7-(4-tert-butylphenyl)-6-methoxy-2-methyl-1H-indene in 200 ml of toluene 12.0 ml (30.0 mmol) of 2.5 M $^n$BuLi in hexanes was added at room temperature. The resulting viscous solution was stirred for 10 h, and then 10 ml of THF was added. The formed mixture was stirred for 2 h at 60° C., then cooled to −20° C., and 19.4 g (150 mmol, 5 eq.) of dichlorodimethylsilane was added in one portion. The resulting solution was warmed to room temperature, refluxed for 1 h, and then filtered through glass frit (G3). The precipitate was additionally washed by 2×10 ml of toluene. The combined filtrate was evaporated to dryness to give 13.2 g (99%) of the title product as a yellowish oil which was further used without an additional purification.

Anal. calc. for C$_{27}$H$_{37}$ClOSi: C, 73.51; H, 8.45. Found: C, 73.38; H, 8.50.

$^1$H NMR (CDCl$_3$): δ 7.45 (d, J=8.5 Hz, 2H, 2,6-H in C$_6$H$_4$$^t$Bu), 7.41-7.38 (m, 3H, 3,5-H in C$_6$H$_4$$^t$Bu and 7-H in indenyl), 6.48 (s, 1H, 3-H in indenyl), 3.54 (s, 1H, 1-H in indenyl), 3.20 (s, 3H, OMe), 2.19 (s, 3H, 2-Me in indenyl), 1.43 (s, 9H, 6-$^t$Bu in indenyl), 1.38 (s, 9H, $^t$Bu in C$_6$H$_4$$^t$Bu), 0.43 (s, 3H, SiMeMe'Cl), 0.16 (s, 3H, SiMeMe'Cl).

[6-tert-Butyl-4-(4-tert-butylphenyl)-5-methoxy-2-methyl-1H-inden-1-yl][4-(4-tert-butylphenyl)-2-methyl-1H-inden-1-yl]dimethylsilane

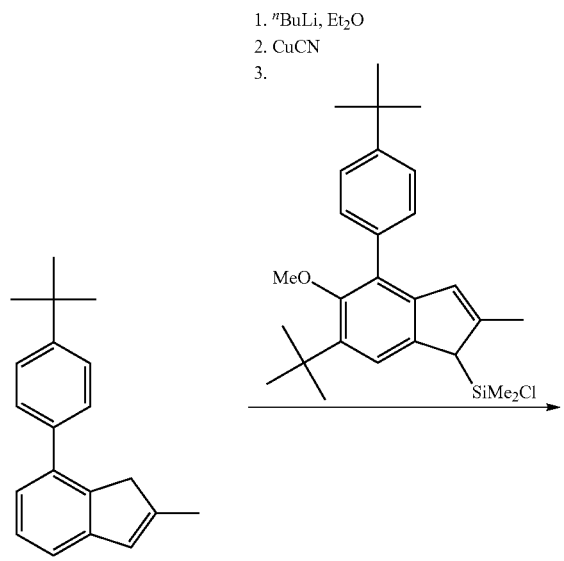

−40° C. This mixture was stirred overnight at room temperature, then cooled to −40° C., and 215 mg of CuCN was added. The resulting mixture was stirred for 1 h at −20° C., then cooled to −40° C., and a solution 13.2 g (30.0 mmol) of [6-tert-butyl-4-(4-tert-butylphenyl)-5-methoxy-2-methyl-1H-inden-1-yl](chloro)dimethylsilane (prepared as described above) in 150 ml of ether was added in one portion. Further on, this mixture was stirred overnight at ambient temperature, then 0.5 ml of water were added. This solution was filtered through a pad of silica gel 60 (40-63 um) which was additionally washed by 2×75 ml of dichloromethane. The combined organic elute was evaporated to dryness, and the residue was dried in vacuum. This procedure gave 20.1 g of the title product (on the evidence of NMR spectroscopy, it has ca. 90% purity and is a ca. 1:1 mixture of the distereomers) as yellowish glass which was further used without an additional purification.

Anal. calc. for C$_{47}$H$_{58}$OSi: C, 84.63; H, 8.76. Found: C, 84.31; H, 8.57.

$^1$H NMR (CDCl$_3$): δ 7.51-7.40 (m), 7.34 (s), 7.33 (s), 7.28-7.21 (m), 7.16-7.10 (m), 6.83 (s), 6.82 (s), 6.50 (s), 3.71 (s), 3.68 (s), 3.66 (s), 3.23 (s), 3.22 (s), 2.19 (s), 2.17 (s), 2.16 (s), 2.11 (s), 1.44 (s), 1.42 (s), 1.39 (s), 1.39 (s), 1.38 (s), −0.12 (s), −0.18 (s), −0.22 (s).

Anti- and syn-dimethylsilanediyl[2-methyl-4-(4-tert-butylphenyl)-inden-1-yl]-[2-methyl-4-(4-tert-butylphenyl)-5-methoxy-6-tert-butyl-inden-1-yl]zirconium dichloride (Metallocene E7)

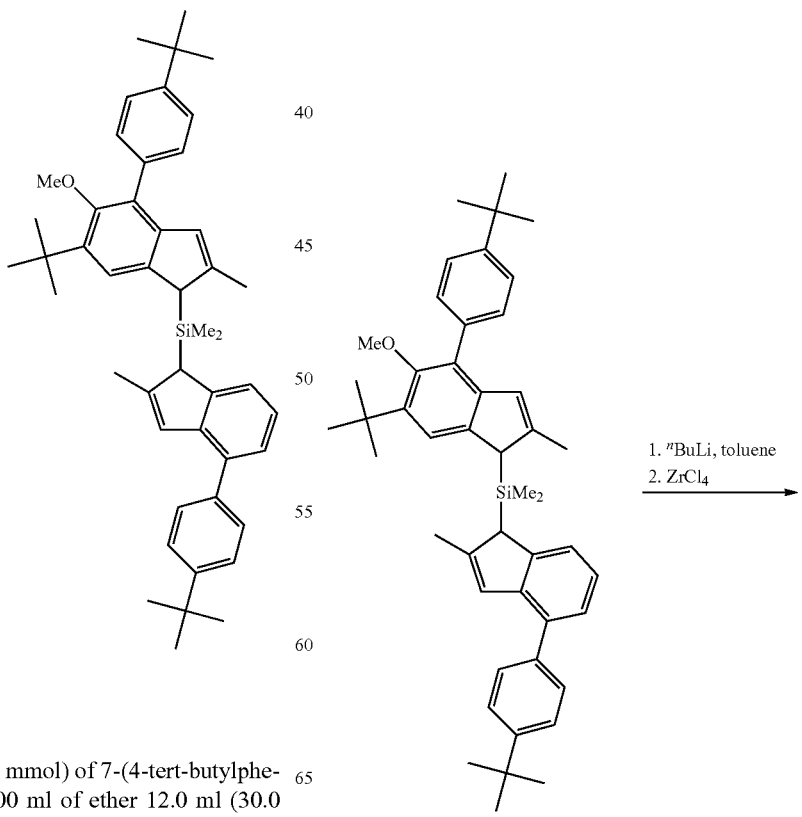

To a solution of 7.88 g (30.0 mmol) of 7-(4-tert-butylphenyl)-2-methyl-1H-indene in 200 ml of ether 12.0 ml (30.0 mmol) of 2.5 M $^n$BuLi in hexanes was added in one portion at -continued

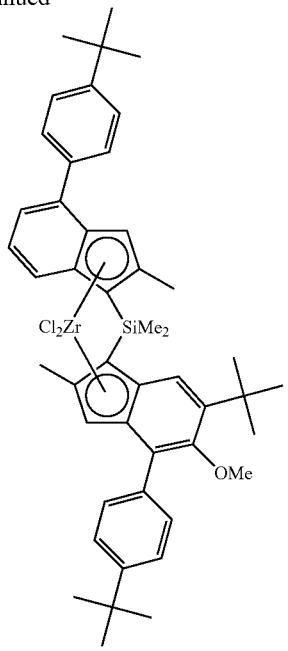

To a solution of 20.1 g (ca. 30.0 mmol) of [6-tert-butyl-4-(4-tert-butylphenyl)-5-methoxy-2-methyl-1H-inden-1-yl][4-(4-tert-butylphenyl)-2-methyl-1H-inden-1-yl]dimethylsilane (of ca. 90% purity as described above) in 250 ml of ether cooled to −30° C. 24.0 ml (60.0 mmol) of 2.5 M $^n$BuLi in hexanes was added in one portion. This mixture was stirred overnight at room temperature. The resulting red solution was cooled to −30° C., and 7.00 g (30.0 mmol) of $ZrCl_4$ was added. The reaction mixture was stirred for 24 h resulting in solution with a large amount of light orange precipitate. The same anti-/syn-ratio equal to 55/45 was found both in solution and precipitate by NMR spectroscopy. The reaction mixture was evaporated to dryness, the residue was treated by 450 ml of hot toluene, and the resulting hot suspension was filtered hot through glass frit (G4). Crystals precipitated from the filtrate at room temperature were collected and dried in vacuum. This procedure gave ca. 10 g of a ca. 4:1 mixture of syn- and anti-zirconocenes. Crystallization of this mixture from 125 ml of hot toluene gave 6.20 g (25%) of pure syn-zirconocene. The mother liquor was evaporated to dryness, and the residue was re-crystallized from 45 ml of toluene to give 2.53 g (10%) of anti-zirconocene as slightly orange powder. Again, the mother liquors was evaporated to dryness, and then 100 ml of n-hexane was added. The suspension was filtered through glass frit (G3), and the precipitate was dried in vacuum. This procedure gave 9.20 g of a ca. 70:30 mixture of anti- and syn-zirconocenes. Thus, the total yield of the isolated ansa-zirconocenes was 17.9 g (72%). Assignment in NMR spectra was made using the following abbreviations: $L^1$ for 4-(4-tert-butylphenyl)-2-methyl-1H-inden-1-yl and $L^2$ for 6-tert-butyl-4-(4-tert-butylphenyl)-5-methoxy-2-methyl-1H-inden-1-yl.

anti-Zirconocene.

Anal. calc. for $C_{47}H_{56}Cl_2OSiZr$: C, 68.25; H, 6.82. Found: C, 68.43; H, 7.01.

$^1$H NMR (CDCl$_3$): δ 7.63-7.61 (m, 3H, 2,6-H in $C_6H_4{}^t$Bu in $L^1$ and 7-H in $L^1$), 7.53-7.51 (m, 3H, 2,6-H in $C_6H_4{}^t$Bu in $L^2$ and 7-H in $L^2$), 7.47-7.42 (m, 4H, 3,5-H in $C_6H_4{}^t$Bu in $L^1$ and 3,5-H in $C_6H_4{}^t$Bu in $L^2$), 7.37 (d, J=7.0 Hz, 1H, 5-H in $L^1$), 7.08 (dd, J=8.5 Hz, J=7.0 Hz, 1H, 6-H in $L^1$), 7.01 (s, 1H, 3-H in $L^1$), 6.62 (s, 1H, 3-H in $L^2$), 3.36 (s, 3H, OMe), 2.24 (s, 3H, 2-Me in $L^1$), 2.17 (s, 3H, 2-Me in $L^2$), 1.39 (s, 9H, $^t$Bu in $C_6H_4{}^t$Bu in $L^1$), 1.33-1.31 (m, 24H, $^t$Bu in $C_6H_4{}^t$Bu in $L^2$, 6-$^t$Bu in $L^2$, SiMeMe' and SiMeMe').

syn-Zirconocene.

Anal. calc. for $C_{47}H_{56}Cl_2OSiZr$: C, 68.25; H, 6.82. Found: C, 68.33; H, 6.98.

$^1$H NMR (CDCl$_3$): δ 7.64 (d, J=8.6 Hz, 1H, 7-H in $L^1$), 7.57 (d, J=7.7 Hz, 2H, 2,6-H in $C_6H_4{}^t$Bu in $L^1$), 7.52-7.41 (m, 7H, 2,6-H in $C_6H_4{}^t$Bu in $L^2$, 7-H in $L^2$, 3,5-H in $C_6H_4{}^t$Bu in $L^1$ and 3,5-H in $C_6H_4{}^t$Bu in $L^2$), 7.17-7.14 (m, 1H, 5-H in $L^1$), 6.91 (s, 1H, 3-H in $L^1$), 7.08 (t, J=7.6 Hz, 1H, 6-H in $L^1$), 6.51 (s, 1H, 3-H in $L^2$), 3.18 (s, 3H, OMe), 2.43 (s, 3H, 2-Me in $L^1$), 2.37 (s, 3H, 2-Me in $L^2$), 1.44 (s, 3H, SiMeMe'), 1.33 (m, 27H, $^t$Bu in $C_6H_4{}^t$Bu in $L^1$, $^t$Bu in $C_6H_4{}^t$Bu in $L^2$, 6-$^t$Bu in $L^2$), 1.22 (s, 3H, SiMeMe').

Synthesis of anti-dimethylsilanediyl[2-methyl-4-(4-tert-butylphenyl)-inden-1-yl][2-methyl-4-(3,5-di-tert-butylphenyl)-5-methoxy-6-tert-butyl-inden-1-yl] zirconium dichloride (Metallocene E8)

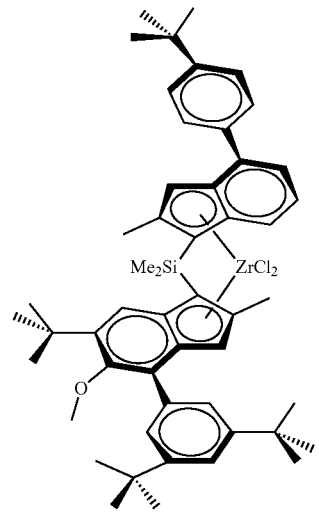

6-tert-Butyl-4-(3,5-di-tert-butylphenyl)-5-methoxy-2-methylindan-1-one

[structure: MeO-substituted bromoindanone] → 3,5-$^t$Bu$_2$C$_6$H$_3$B(OH)$_2$, Na$_2$CO$_3$, Pd(OAc)$_2$, PPh$_3$, H$_2$O-DME

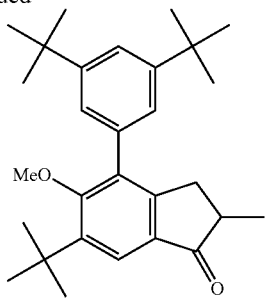

A mixture of 30.7 g (98.6 mmol) of 4-bromo-6-tertbutyl-5-methoxy-2-methylindanone, 30.6 g (128 mmol) 3,5-di-tert-butylphenylboronic acid, 29.7 g (280 mmol) of Na$_2$CO$_3$, 1.35 g (5.92 mmol; 6 mol. %) of Pd(OAc)$_2$, 3.15 g (11.8 mmol; 12 mol. %) of PPh$_3$, 130 ml of water, and 380 ml of 1,2-dimethoxyethane was refluxed for 12 h. Further on, the reaction mixture was quenched with water, solvents were evaporated. The residue was dissolved in 500 ml of dichloromethane, and this solution was washed by 500 ml of water. The organic layer was separated, the aqueous layer was additionally extracted with 100 ml of dichloromethane. The combined organic extract was dried over Na$_2$SO$_4$, then evaporated to dryness. The crude product isolated from the residue using flash chromatography on silica gel 60 (40-63 um, hexanes-dichloromethane=2:1, vol.) was then re-crystallized from n-hexane to give 18.5 g (43%) of a white solid.

Anal. calc. for C$_{29}$H$_{40}$O$_2$: C, 82.81; H, 9.59. Found: C, 83.04; H, 9.75.

$^1$H NMR (CDCl$_3$): δ 7.74 (s, 1H, 7-H in indan-1-one), 7.41 (t, J=1.6 Hz, 1H, 4-H in C$_6$H$_3$$^t$Bu$_2$), 7.24 (d, J=1.6 Hz, 2,6-H in C$_6$H$_3$$^t$Bu$_2$), 3.24 (s, 3H, OMe), 3.17 (dd, J=17.3 Hz, J=8.0 Hz, 1H, 3-H in indan-1-one), 2.64 (m, 1H, 2-H in indan-1-one), 2.47 (dd, J=17.3 Hz, J=3.7 Hz, 1H, 3-H' in indan-1-one), 1.43 (s, 9H, 6-$^t$Bu in indan-1-one), 1.36 (s, 18H, $^t$Bu in C$_6$H$_3$$^t$Bu$_2$), 1.25 (d, J=7.3 Hz, 3H, 2-Me in indan-1-one).

5-tert-Butyl-7-(3,5-di-tert-butylphenyl)-6-methoxy-2-methyl-1H-indene

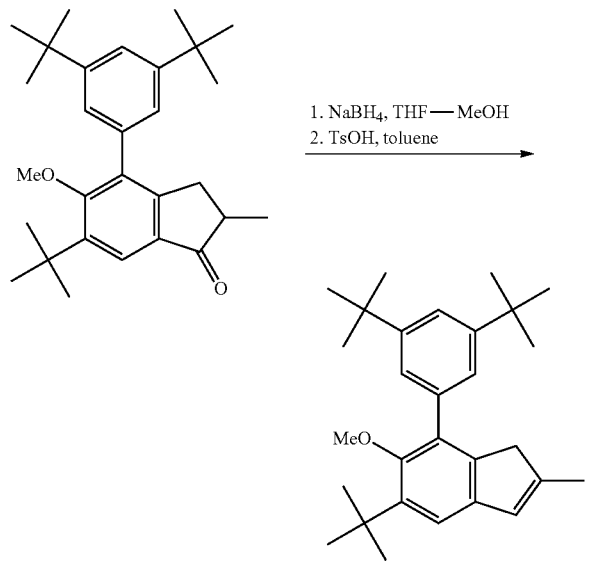

1. NaBH$_4$, THF—MeOH
2. TsOH, toluene

To a solution of 16.3 g (38.8 mmol) of 6-tert-butyl-4-(3,5-di-tert-butylphenyl)-5-methoxy-2-methylindan-1-one in 200 ml of THF cooled to 5° C. 1.47 g (38.9 mmol) of NaBH$_4$ was added. Further on, 80 ml of methanol was added dropwise to this mixture by vigorous stirring for ca. 7 h at 5° C. The resulting mixture was evaporated to dryness, and the residue was treated by 300 ml of dichloromethane and 300 ml of 2 M HCl. The organic layer was separated, the aqueous layer was additionally extracted with 100 ml of dichloromethane. The combined organic extract was evaporated to dryness to give a colorless oil. To a solution of this oil in 250 ml of toluene 0.1 g of TsOH was added, this mixture was refluxed with Dean-Stark head for 15 min and then cooled to room temperature using water bath. The resulting solution was washed by 10% aqueous Na$_2$CO$_3$. The organic layer was separated, the aqueous layer was extracted with 2×50 ml of dichloromethane. The combined organic extract was dried over K$_2$CO$_3$ and then passed through a short layer of silica gel 60 (40-63 um). The silica gel layer was additionally washed by 100 ml of dichloromethane. The combined organic elute was evaporated to dryness to give 15.7 g (99%) of a white crystalline product which was further used without an additional purification.

Anal. calc. for C$_{29}$H$_{40}$O: C, 86.08; H, 9.96. Found: C, 86.26; H, 10.21.

$^1$H NMR (CDCl$_3$): δ 7.36 (t, J=1.8 Hz, 1H, 4H in C$_6$H$_3$$^t$Bu$_2$), 7.33 (d, J=1.8 Hz, 2H, 2,6-H in C$_6$H$_3$$^t$Bu$_2$), 7.21 (s, 1H, 4-H in indenyl), 6.44 (m, 1H, 3-H in indenyl), 3.17 (s, 3H, OMe), 3.14 (s, 2H, 1-H in indenyl), 2.06 (s, 3H, 2-Me in indenyl), 1.44 (s, 9H, 5-$^t$Bu in indenyl), 1.35 (s, 18H, $^t$Bu in C$_6$H$_3$$^t$Bu$_2$). $^{13}$C{$^1$H} NMR (CDCl$_3$): δ 150.4, 145.2 (two resonances), 141.7, 140.9, 140.6, 137.3, 132.5, 126.9, 124.0, 120.1, 116.9, 60.2, 43.0, 35.2, 34.9, 31.5, 31.0, 16.7.

[6-tert-Butyl-4-(3,5-di-tert-butylphenyl)-5-methoxy-2-methyl-1H-inden-1-yl](chloro)-dimethylsilane

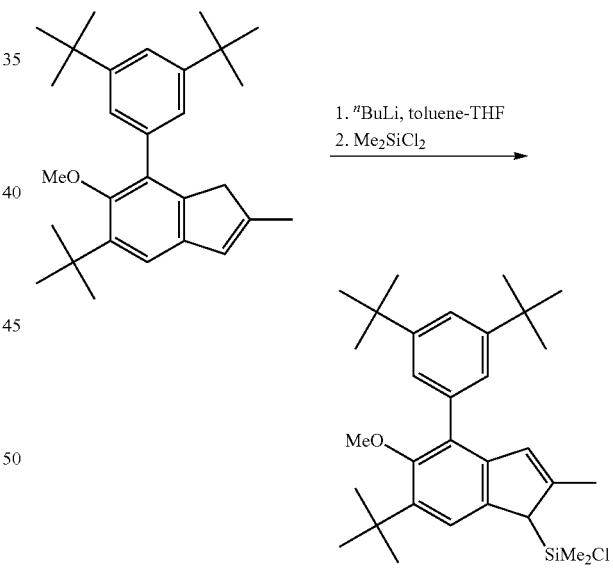

1. $^n$BuLi, toluene-THF
2. Me$_2$SiCl$_2$

To a solution of 15.7 g (38.8 mmol) of 5-tert-butyl-7-(3,5-di-tert-butylphenyl)-6-methoxy-2-methyl-1H-indene in 200 ml of toluene 16.0 ml (40.0 mmol) of 2.5 M $^n$BuLi in hexanes was added at room temperature. The resulting viscous solution was stirred for 10 h, and then 10 ml of THF was added. This mixture was stirred for 2 h at 60° C., then cooled to −20° C., and 25.0 g (194 mmol, 5 eq.) of dichlorodimethylsilane was added in one portion. The resulting solution was refluxed for 2 h, then evaporated to ca. ¾ of its volume, and filtered through glass frit (G3). The precipitate was additionally washed by 2×30 ml of toluene. The combined filtrate was evaporated to dryness to give 19.2 g (99%) of white solid which was further used without an additional purification.

Anal. calc. for $C_{31}H_{45}ClOSi$: C, 74.88; H, 9.12. Found: C, 75.12; H, 9.37.

$^1$H NMR (CDCl$_3$): δ 7.38 (s, 1H, 7-H in indenyl), 7.36 (t, J=1.6 Hz, 1H, 4-H in $C_6H_3{}^tBu_2$), 7.33 (d, J=1.6 Hz, 2H, 2,6-H in $C_6H_3{}^tBu_2$), 6.49 (m, 1H, 3-H in indenyl), 3.54 (s, 1H, 1-H in indenyl), 3.17 (s, 3H, OMe), 2.19 (s, 3H, 2-Me in indenyl), 1.44 (s, 9H, 6-$^t$Bu in indenyl), 1.36 (s, 18H, $^t$Bu in $C_6H_3{}^tBu_2$), 0.45 (s, 3H, SiMeMe'), 0.18 (s, 3H, SiMeMe').

[6-tert-Butyl-4-(3,5-di-tert-butylphenyl)-5-methoxy-2-methyl-1H-inden-1-yl][4-(4-tert-butylphenyl)-2-methyl-1H-inden-1-yl]dimethylsilane

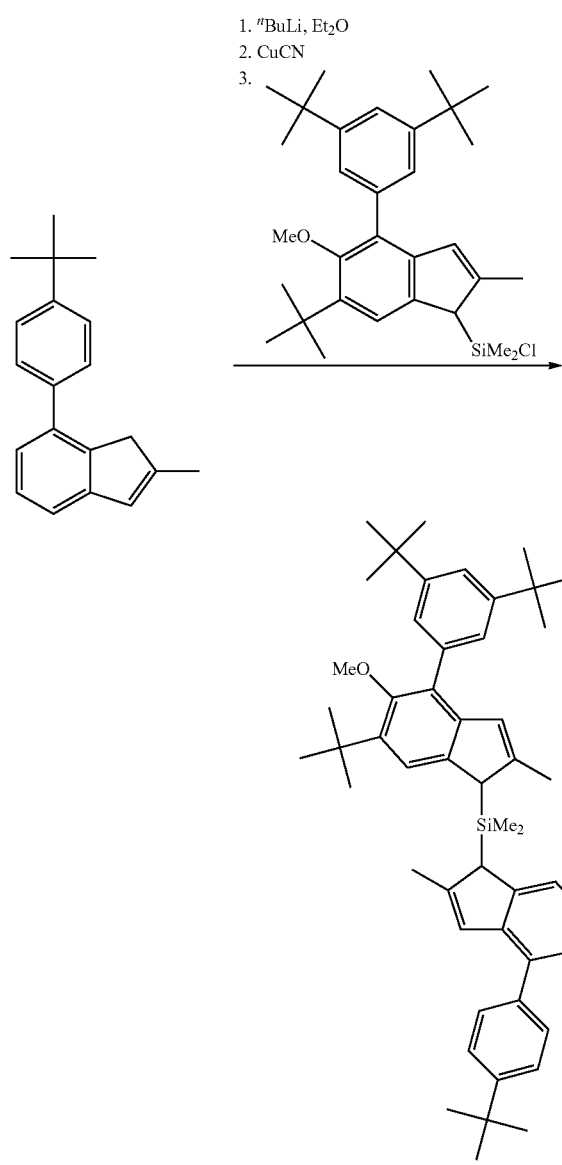

To a solution of 5.54 g (21.1 mmol) of 7-(4-tert-butylphenyl)-2-methyl-1H-indene in 150 ml of ether 8.50 ml (21.3 mmol) of 2.5 M $^n$BuLi in hexanes was added in one portion at −40° C. This mixture was stirred overnight at room temperature, then cooled to −40° C., and 190 mg of CuCN was added. The resulting mixture was stirred for 1 h at −20° C., then cooled to −40° C., and a solution of 10.5 g (21.1 mmol) of [6-tert-butyl-4-(3,5-di-tert-butylphenyl)-5-methoxy-2-methyl-1H-inden-1-yl](chloro)dimethyl-silane in 150 ml of ether was added in one portion. Further on, this mixture was stirred overnight at ambient temperature, then 0.5 ml of water was added. This solution was filtered through a pad of silica gel 60 (40-63 um) which was additionally washed by 2×75 ml of dichloromethane. The combined elute was evaporated to dryness, and the residue was triturated with 70 ml of n-hexane. The obtained suspension was filtered on glass frit, the precipitate was washed with 30 ml of n-hexane and dried in vacuum to give a white powder. Additionally, the mother liquor was evaporated to small volume. The formed suspension was filtered through glass frit (G3), and the precipitate was washed with 2×15 ml of n-hexane and then dried in vacuum. Again, the mother liquor was evaporated to give a yellowish oil which was re-crystallized at −30° C. for two months. Crystals precipitated from this solution were collected and dried in vacuum. Thus, 12.2 g (80%) of the title product was isolated. Assignment in NMR spectra was made using the following abbreviations: L$^1$ for 4-(4-tert-butylphenyl)-2-methyl-1H-inden-1-yl and L$^2$ for 6-tert-butyl-4-(3,5-di-tert-butylphenyl)-5-methoxy-2-methyl-1H-inden-1-yl.

Anal. calc. for $C_{51}H_{66}OSi$: C, 84.70; H, 9.20. Found: C, 84.91; H, 9.35.

$^1$H NMR (CDCl$_3$): δ 7.48-7.46 (s, 5H, 2,6-H in $C_6H_4{}^tBu$ and 2,4,6-H in $C_6H_3{}^tBu_2$), 7.38 (s, 3H, 3,5-H in $C_6H_4{}^tBu$ and 7-H in L$^2$), 7.34 (d, J=7.5 Hz, 1H, 7-H in L$^1$), 7.24 (d, J=7.5 Hz, 1H, 5-H in L$^1$), 7.14 (t, J=7.5 Hz, 1H, 6-H in L$^1$), 6.80 (s, 1H, 3-H in L$^2$), 6.51 (s, 1H, 3-H in L$^2$), 3.71 (s, 1H, 1-H in L$^1$), 3.68 (s, 1H, 1-H in L$^2$), 3.20 (s, 3H, OMe), 2.18 (s, 3H, 2-Me in L$^1$), 2.13 (s, 3H, 2-Me in L$^2$), 1.44 (s, 9H, 6-$^t$Bu in L$^2$), 1.39 (s, 9H, $^t$Bu in $C_6H_4{}^tBu$), 1.38 (s, 18H, $^t$Bu in $C_6H_3{}^tBu_2$), −0.13 (s, 3H, SiMeMe'), −0.21 (s, 3H, SiMeMe').

Anti- and syn-dimethylsilanediyl[2-methyl-4-(4-tert-butylphenyl)-inden-1-yl][2-methyl-4-(3,5-di-tert-butylphenyl)-5-methoxy-6-tert-butyl-inden-1-yl] zirconium dichloride (Metallocene E8)

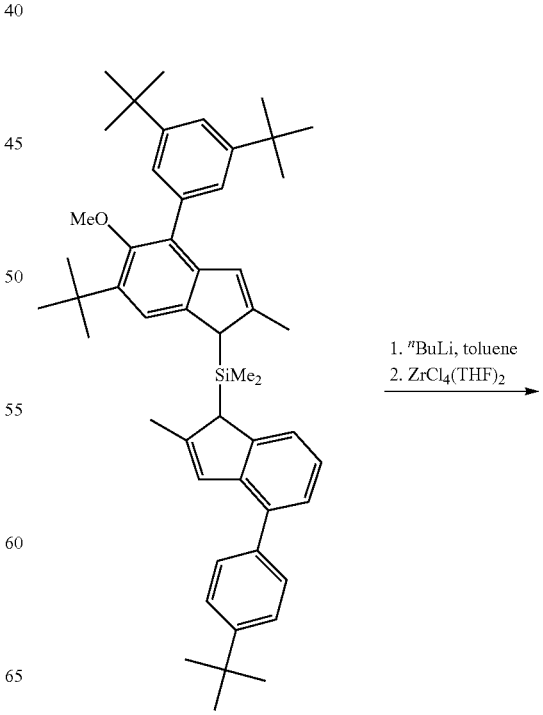

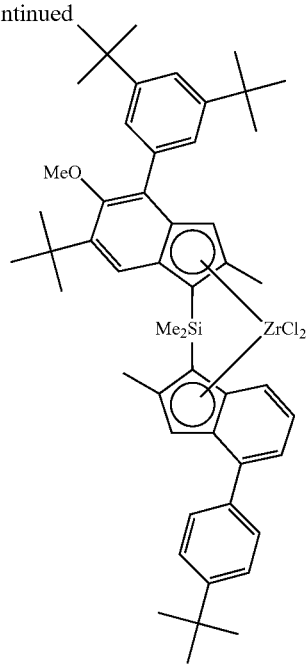

To a solution of 10.3 g (14.2 mmol) of [6-tert-butyl-4-(3,5-di-tert-butylphenyl)-5-methoxy-2-methyl-1H-inden-1-yl][4-(4-tert-butylphenyl)-2-methyl-1H-inden-1-yl]dimethylsilane in 200 ml of toluene (slightly warm solution was used because of low solubility of the starting bridging ligand) 11.4 ml (28.5 mmol) of 2.5 M $^n$BuLi in hexanes was added in one portion. This mixture was stirred overnight at room temperature, then for 2 h at 80° C. The resulting mixture was cooled to −20° C., and 5.37 g (14.2 mmol) of ZrCl$_4$(THF)$_2$ was added. This mixture was stirred for 24 h, then 20 ml of THF was added. The formed mixture was stirred for 3 h at 80° C. and then evaporated to ca. 150 ml. The resulting mixture was filtered through glass frit (G4) at 80° C. to give on the evidence of NMR spectroscopy a ca. 1 to 1 solution of anti- and syn-zirconocenes. This filtrate was then evaporated to ca. 10 ml, and then 100 ml of n-hexane was added. The formed orange precipitate was immediately filtered off on glass frit (G4), washed with 2×10 ml of n-hexane, and dried in vacuum. This procedure gave 2.10 g of syn-zirconocene contaminated with 2% of anti-isomer. The filtrate was evaporated to dryness, and the residue was re-crystallized from n-hexane. Crystals precipitated from this solution were collected and dried in vacuum to give 3.52 g of a ca. 1:1 mixture of syn- and anti-zirconocenes. Additionally, 1.46 g of a ca. 1:10 mixture of syn- and anti-zirconocenes precipitated after one week from the filtrate at room temperature. The latter product was re-crystallized from 25 ml of hot n-octane. Crystals precipitated at room temperature were collected and dried in vacuum to give 0.75 g of pure anti-zirconocene. The mother liquor was evaporated to 7 ml, then the residue was heated to dissolve the formed precipitate. Crystals precipitated from this solution at room temperature were collected and dried in vacuum to give 490 mg of anti-zirconocene contaminated with 8% of syn-isomer. Assignment in NMR spectra was made using the following abbreviations: L$^1$ for 4-(4-tert-butylphenyl)-2-methyl-1H-inden-1-yl and L$^2$ for 6-tert-butyl-4-(3,5-di-tert-butylphenyl)-5-methoxy-2-methyl-1H-inden-1-yl.

anti-Zirconocene.

Anal. calc. for C$_{51}$H$_{64}$Cl$_2$OSiZr: C, 69.35; H, 7.30. Found: C, 69.54; H, 7.49.

$^1$H NMR (CDCl$_3$): δ 7.63-7.61 (m, 3H, 7-H in L$^1$ and 2,6-H in C$_6$H$_4$$^t$Bu), 7.51 (s, 1H, 7-H in L$^2$), 7.47 (d, J=8.5 Hz, 2H, 3,5-H in C$_6$H$_4$$^t$Bu), 7.44 (br. s, 2H, 2,6-H in C$_6$H$_3$$^t$Bu$_2$), 7.37 (d, J=6.8 Hz, 1H, 5-H in L$^1$), 7.34 (t, J=1.6 Hz, 1H, 4-H in C$_6$H$_3$$^t$Bu$_2$), 7.07 (dd, J=8.5 Hz, J=6.9 Hz, 1H, 6-H in L$^1$), 7.01 (s, 1H, 3-H in L$^1$), 6.62 (s, 1H, 3-H in L$^2$), 3.35 (s, 3H, OMe), 2.25 (s, 3H, 2-Me in L$^2$), 2.19 (s, 3H, 2-Me in L$^1$), 1.40 (s, 9H, 6-$^t$Bu in L$^2$), 1.34 (s, 9H, $^t$Bu in C$_6$H$_4$$^t$Bu), 1.33-1.23 (m, $^t$Bu in C$_6$H$_3$$^t$Bu$_2$, SiMeMe' and SiMeMe').

syn-Zirconocene.

Anal. calc. for C$_{51}$H$_{64}$Cl$_2$OSiZr: C, 69.35; H, 7.30. Found: C, 69.33; H, 7.58.

$^1$H NMR (CDCl$_3$): δ 7.65 (d, 1H, J=8.6 Hz, 7-H in L$^1$), 7.57 (d, J=8.5 Hz, 2H, 2,6-H in C$_6$H$_4$$^t$Bu), 7.52 (s, 1H, 7-H in L$^2$), 7.47 (d, J=8.5 Hz, 2H, 3,5-H in C$_6$H$_4$$^t$Bu), 7.44 (br. s, 2H, 2,6-H in C$_6$H$_3$$^t$Bu$_2$), 7.33 (t, J=1.6 Hz, 1H, 4-H in C$_6$H$_3$$^t$Bu$_2$), 7.13 (d, J=6.8 Hz, 1H, 5-H in L$^1$), 6.90 (s, 1H, 3-H in L$^1$), 6.85 (dd, J=8.6 Hz, J=6.8 Hz, 1H, 6-H in L$^1$), 6.50 (s, 1H, 3-H in L$^2$), 3.14 (s, 3H, OMe), 2.44 (s, 3H, 2-Me in L$^2$), 2.38 (s, 3H, 2-Me in L$^1$), 1.44 (s, 3H, SiMeMe'), 1.35-1.33 (m, 36H, 6-$^t$Bu in L$^2$, $^t$Bu in C$_6$H$_4$$^t$Bu and $^t$Bu in C$_6$H$_3$$^t$Bu$_2$), 1.22 (s, 3H, SiMeMe').

Synthesis of anti-dimethylsilanediyl[2-methyl-4-(4-tert-butylphenyl)-inden-1-yl](2-methyl-4-phenyl-5-isobutoxy-6-tert-butyl-inden-1-yl)zirconium dichloride (metallocene E9)

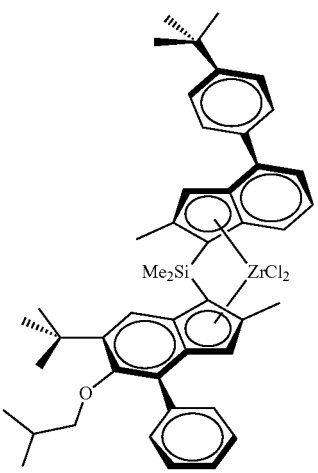

1-tert-Butyl-2-isobutoxybenzene

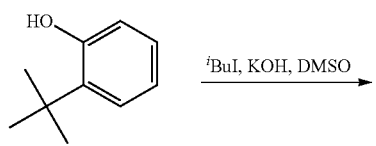

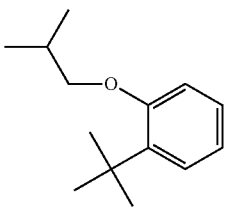

To a solution of 60.1 g (0.40 mol) 2-tert-butylphenol in 600 ml of DMSO 89.6 g (1.60 mol) of KOH and 147 g (0.80 mol) of isobutyl iodide were added. This mixture was stirred for 2 h at room temperature, then 73.6 g (0.40 mol) of isobutyl iodide was added. The resulting mixture was stirred for 1 h, and, again, then 73.6 g (0.40 mol) of isobutyl iodide was added. The formed mixture was stirred overnight at room temperature. The top layer was separated. To the bottom layer 5 liters of water was added, and some product was extracted with 2×250 ml of dichloromethane. The combined organic extract (including the separated top layer) was washed with 5×1 liter of water, dried over $Na_2SO_4$, and evaporated to dryness. The crude product (free of 2-tert-butylphenol) was obtained from the residue by flash chromatography on silica gel 60 (40-63 um; eluent: hexanes). Further on, this crude product was distillated to give pure 1-tert-butyl-2-isobutoxybenzene, b.p. 85-95° C./4 mm Hg. This procedure gave 44.9 g (54%) of the title product.

Anal. calc. for $C_{14}H_{22}O$: C, 81.50; H, 10.75. Found: C, 81.45; H, 10.84.

$^1$H NMR ($CDCl_3$): δ 7.35 (dd, J=7.7 Hz, J=1.6 Hz, 1H, 6-H), 7.22 (td, J=7.7 Hz, J=1.6 Hz, 1H, 5-H), 6.96-6.90 (m, 2H, 3,4-H), 3.82 (d, J=6.3 Hz, 2H, $OCH_2CHMe_2$), 2.23 (m, 1H, $OCH_2CHMe_2$), 1.47 (s, 9H, tu), 1.15 (d, J=6.7 Hz, 6H, $OCH_2CHMe_2$).

5-Isobutoxy-6-tert-butyl-2-methylindanone

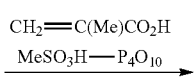

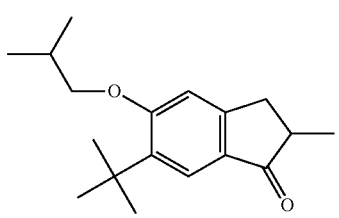

A mixture of 75.1 g (0.872 mol) of methacrylic acid and 90.0 g (0.436 mol) of 1-tert-butyl-2-isobutoxybenzene was added dropwise to Eaton's reagent (prepared from 119 g of $P_4O_{10}$ and 600 ml of $MeSO_3H$) for 2 h at 50° C. The resulting mixture was stirred at 50° C. for 30 min, then cooled to room temperature, and poured into 1 liter of cold water. The crude product was extracted with 3×200 ml of dichloromethane. The organic extract was washed with aqueous $K_2CO_3$, dried over $Na_2SO_4$, and then passed through a pad of silica gel (40-63 um). The silica gel pad was additionally washed by 100 ml of dichloromethane. The combined elute was evaporated to dryness. The residue was distilled in vacuum, b.p. 155-170° C./5 mm Hg. The product was purified by flash chromatography on silica gel 60 (40-63 um; eluent: n-hexane-dichloromethane-ether=25:25:1, vol.) to give 91.9 g (76%) of the title indanone.

Anal. calc. for $C_{18}H_{26}O_2$: C, 78.79; H, 9.55. Found: C, 78.94; H, 9.70.

$^1$H NMR ($CDCl_3$): δ 7.69 (s, 1H, 7-H in indan-1-one), 6.87 (s, 1H, 4-H in indan-1-one), 3.86 (d, J=6.3 Hz, 2H, $OCH_2CHMe_2$), 3.30 (dd, J=16.5 Hz, J=7.1 Hz, 1H, 3-H in indan-1-one), 2.69-2.59 (m, 2H, 2,3'-H in indan-1-one), 2.22 (m, 1H, $OCH_2CHMe_2$), 1.41 (s, 9H, $^tBu$), 1.28 (d, J=7.3 Hz, 3H, 2-Me in indan-1-one), 1.11 (d, J=6.7 Hz, 6H, $OCH_2CHMe_2$).

4-Bromo-5-isobutoxy-6-tert-butyl-2-methylindanone

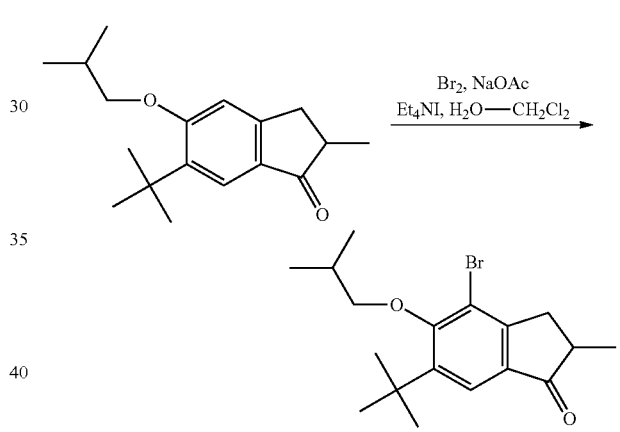

To a mixture of 91.9 g (335 mmol) of 5-isobutoxy-6-tert-butyl-2-methylindanone, 82.5 g (1.0 mol) of NaOAc, 1.70 g (7.0 mmol) of tetraethylammonium iodide, 500 ml of water, and 170 ml of dichloromethane 17.2 ml (335 mmol) of bromine was added by vigorous stirring for 1 h at 0° C. The resulting mixture was stirred for 1 h at this temperature, and then 41.3 g (0.5 mol) of NaOAc was added. To the obtained mixture 9.0 ml (175 mmol) of bromine was added dropwise for 0.5 h at 0° C. The formed mixture was stirred for 2 h at 0° C., then $Na_2SO_3$ was added to remove an excess of bromine. The organic layer was separated, dried over $Na_2SO_4$, and then evaporated to dryness. This procedure gave 116 g (98%) of the title product which was further used without an additional purification.

Anal. calc. for $C_{18}H_{25}BrO_2$: C, 61.19; H, 7.13. Found: C, 61.36; H, 7.33.

$^1$H NMR ($CDCl_3$): δ7.71 (s, 1H, 7-H in indan-1-one), 3.93 (m, 2H, $OCH_2CHMe_2$), 3.29 (dd, J=17.5 Hz, J=7.7 Hz, 1H, 3-H in indan-1-one), 2.76-2.67 (m, 1H, 2-H in indan-1-one), 2.60 (dd, J=17.5 Hz, J=3.8 Hz, 1H, 3'-H in indan-1-one), 2.34 (m, 1H, $OCH_2CHMe_2$), 1.41 (s, 9H, 6-$^tBu$ in indan-1-one), 1.31 (d, J=7.3 Hz, 3H, 2-Me in indan-1-one), 1.10 (d, J=6.7 Hz, 6H, $OCH_2CHMe_2$).

6-tert-Butyl-5-isobutoxy-2-methyl-4-phenylindan-1-one

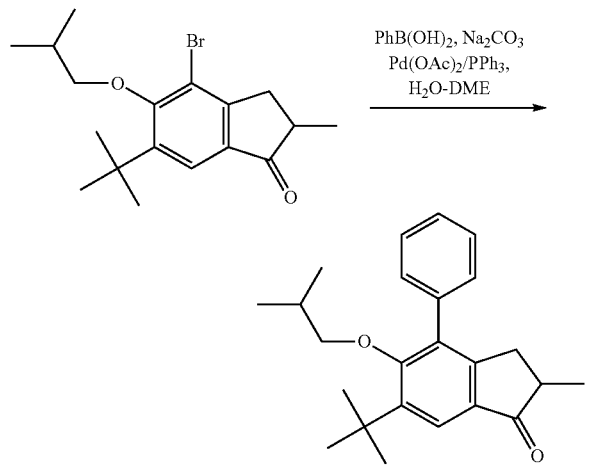

A mixture of 48.4 g (137 mmol) of 4-bromo-5-isobutoxy-6-tertbutyl-2-methylindanone, 25.0 g (205 mmol) of phenylboronic acid, 40.5 g (382 mmol) of $Na_2CO_3$, 1.90 g (8.22 mmol, 6 mol %) of $Pd(OAc)_2$, 4.30 g (16.4 mmol, 12 mol %) of $PPh_3$, 180 ml of water, and 520 ml of DME was refluxed for 6 h. Then, this reaction mixture was quenched with water, solvents were evaporated. The residue was dissolved in 500 ml of dichloromethane, this solution was washed with 500 ml of water. The organic layer was separated, the aqueous layer was additionally extracted with 100 ml of dichloromethane. The combined organic extract was evaporated to dryness, the crude product was obtained from the residue by flash chromatography on silica gel 60 (40-63 um; eluent: hexanes-dichloromethane=2:1, vol.). This crude product was re-crystallized from n-hexane to give 40.3 g (84%) as a white solid.

Anal. calc. for $C_{24}H_{30}O_2$: C, 82.24; H, 8.63. Found: C, 82.02; H, 8.49.

$^1$H NMR ($CDCl_3$): δ7.77 (s, 1H, 7-H in indan-1-one), 7.47-7.36 (m, 5H, 2,3,4,5,6-H in Ph), 3.25 (d, J=6.7 Hz, 2H, $OCH_2CHMe_2$), 3.11 (dd, J=17.3 Hz, J=7.7 Hz, 1H, 3-H in indan-1-one), 2.62 (m, 1H, 2-H in indan-1-one), 2.44 (dd, J=17.3 Hz, J=3.8 Hz, 1H, 3'-H in indan-1-one), 1.65 (m, 1H, $OCH_2CHMe_2$), 1.44 (s, 9H, 6-$^t$Bu in indan-1-one), 1.25 (d, J=7.3 Hz, 3H, 2-Me in indan-1-one), 0.66 (d, J=6.7 Hz, 6H, $OCH_2CHMe_2$).

5-tert-Butyl-6-isobutoxy-2-methyl-7-phenyl-1H-indene

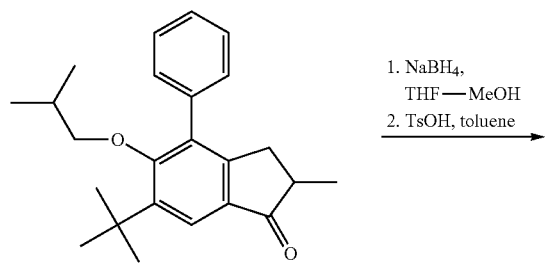

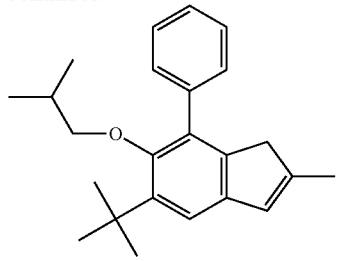

To a solution of 34.0 g (97.0 mmol) of 6-tert-butyl-5-isobutoxy-2-methyl-4-phenylindan-1-one in 300 ml of THF cooled to 5° C. 5.00 g (132 mmol) of $NaBH_4$ was added. Further on, 150 ml of methanol was added dropwise to this mixture by vigorous stirring for ca. 7 h at 5° C. The resulting mixture was evaporated to dryness, and the residue was partitioned between 500 ml of dichloromethane and 500 ml of 1 M HCl. The organic layer was separated, the aqueous layer was additionally extracted with 100 ml of dichloromethane. The combined organic extract was evaporated to dryness to give a colorless oil. To a solution of this oil in 500 ml of toluene 1 g of TsOH was added, and this mixture was refluxed with Dean-Stark head for 15 min and then cooled to room temperature using a water bath. The resulting solution was washed by 10% aqueous $Na_2CO_3$. The organic layer was separated, the aqueous layer was extracted with 2×100 ml of dichloromethane. The combined organic solution was dried over $K_2CO_3$ and then passed through a short pad of silica gel 60 (40-63 um). The silica gel pad was additionally washed by 100 ml of dichloromethane. The combined organic elute was evaporated to dryness. This procedure gave 32.4 g (99%) of 5-tert-butyl-6-isobutoxy-2-methyl-7-phenyl-1H-indene which was further used without an additional purification.

Anal. calc. for $C_{24}H_{30}O$: C, 86.18; H, 9.04. Found: C, 86.01; H, 9.20.

$^1$H NMR ($CDCl_3$): δ 7.45 (d, J=7.7 Hz, 2H, 2,6-H in Ph), 7.41-7.37 (m, 2H, 3,5-H in Ph), 7.30 (t, J=7.2 Hz, 1H, 4-H in Ph), 7.22 (s, 1H, 4-H in indenyl), 6.43 (m, 1H, 3-H in indenyl), 3.18 (d, J=6.5 Hz, 2H, $OCH_2CHMe_2$), 3.10 (s, 2H, 1-H in indenyl), 2.04 (s, 3H, 2-Me in indenyl), 1.61 (m, 1H, $OCH_2CHMe_2$), 1.44 (s, 9H, 5-$^t$Bu in indenyl), 0.64 (d, J=6.7 Hz, 6H, $OCH_2CHMe_2$).

(6-tert-Butyl-5-isobutoxy-2-methyl-4-phenyl-1H-inden-1-yl)(chloro)dimethylsilane

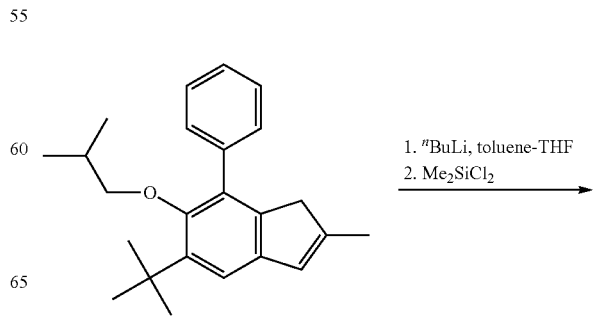

-continued

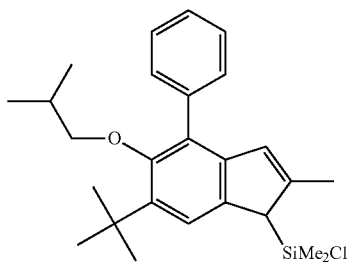

To a solution of 16.8 g (50.2 mmol) of 5-tert-butyl-6-isobutoxy-2-methyl-7-phenyl-1H-indene in 200 ml of toluene 20.1 ml (50.5 mmol) of 2.5 M $^n$BuLi in hexanes was added at room temperature. The formed viscous solution was stirred for 10 h, and then 10 ml of THF was added. The resulting mixture was stirred for 1 h at 65° C., then cooled to −20° C., and 32.5 g (252 mmol, 5 eq.) of dichlorodimethylsilane was added in one portion. This mixture was warmed to room temperature, refluxed for 0.5 h, and then filtered through glass frit (G3). The precipitate was additionally washed by 2×30 ml of toluene. The combined filtrate was evaporated to dryness to give 21.5 g (99%) of (6-tert-butyl-5-isobutoxy-2-methyl-4-phenyl-1H-inden-1-yl)(chloro)dimethylsilane which was further used without an additional purification.

Anal. calc. for $C_{26}H_{35}ClOSi$: C, 73.12; H, 8.26. Found: C, 73.49; H, 8.52.

$^1$H NMR (CDCl$_3$): δ 7.55-7.45 (m, 5H, 2,3,5,6-H in Ph and 7-H in indenyl), 7.38 (t, J=7.1 Hz, 1H, 4-H in Ph), 6.49 (s, 1H, 3-H in indenyl), 3.61 (s, 1H, 1-H in indenyl), 3.22 (m, 2H, OCH$_2$CHMe$_2$), 2.24 (s, 3H, 2-Me in indenyl), 1.73 (m, 1H, OCH$_2$CHMe$_2$), 1.51 (s, 9H, 6-$^t$Bu in indenyl), 0.73 (dd, J=13.3 Hz, J=6.6 Hz, 6H, OCH$_2$CHMe$_2$), 0.49 (s, 3H, SiMeMe'Cl), 0.23 (s, 3H, SiMeMe'Cl).

(6-tert-Butyl-5-isobutoxy-2-methyl-4-phenyl-1H-inden-1-yl)[4-(4-tert-butylphenyl)-2-methyl-1H-inden-1-yl]dimethylsilane

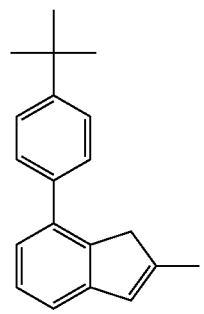

1. $^n$BuLi, Et$_2$O
2. CuCN
3.

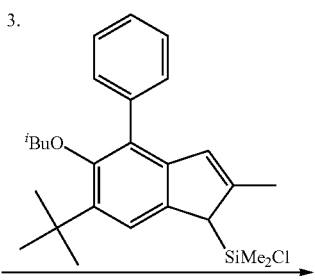

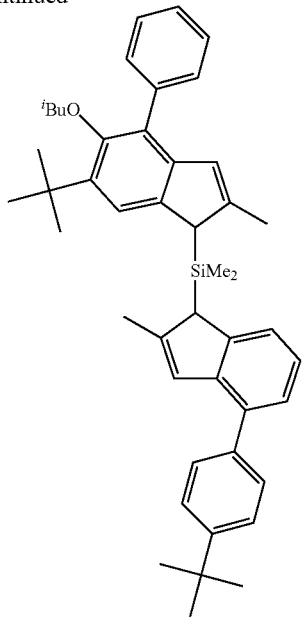

To a solution of 13.2 g (50.3 mmol) of 7-(4-tert-butylphenyl)-2-methyl-1H-indene in 200 ml of ether 20.1 ml (50.3 mmol) of 2.5 M $^n$BuLi in hexanes was added in one portion at −40° C. This mixture was stirred overnight at room temperature, then cooled to −40° C., and 200 mg of CuCN was added. The resulting mixture was stirred for 1 h at −20° C., then cooled to −40° C., and a solution of 21.5 g (50.2 mmol) of (6-tert-butyl-5-isobutoxy-2-methyl-4-phenyl-1H-inden-1-yl)(chloro)dimethylsilane in 200 ml of ether was added in one portion. Further on, this mixture was stirred overnight at ambient temperature, then 0.5 ml of water was added. This solution was filtered through a pad of silica gel 60 (40-63 um) which was additionally washed by 2×75 ml of dichloromethane. The combined elute was evaporated to dryness in vacuum. The residue was re-crystallized from 250 ml of hot n-hexane. Crystals precipitated at room temperature were collected, washed with 2×50 ml of n-hexane, and dried in vacuum. This procedure gave 11.4 g (35%) of anti-(6-tert-butyl-5-isobutoxy-2-methyl-4-phenyl-1H-inden-1-yl)[4-(4-tert-butylphenyl)-2-methyl-1H-inden-1-yl]dimethylsilane. The mother liquor was evaporated to dryness, and the products were isolated by flash-chromatography on silica gel 60 (40-63 um; eluent: hexanes-dichloromethane=10:1, vol., then 3:1, vol.). This procedure gave 11.6 g (35%) of (6-tert-butyl-5-isobutoxy-2-methyl-4-phenyl-1H-inden-1-yl)[4-(4-tert-butylphenyl)-2-methyl-1H-inden-1-yl]dimethylsilane as a ca. 2:1 mixture of syn- and anti-isomers. Thus, the overall yield of the title product was 70%. Assignment in NMR spectra was made using the following abbreviations: $L^1$ for 4-(4-tert-butylphenyl)-2-methyl-1H-inden-1-yl and $L^2$ for 6-tert-butyl-5-isobutoxy-2-methyl-4-phenyl-1H-inden-1-yl.

Anal. calc. for $C_{46}H_{56}OSi$: C, 84.61; H, 8.64. Found: C, 84.94; H, 8.73.

rac-compound: $^1$H NMR (CDCl$_3$): δ 7.51-7.46 (m, 6H, 2,3,5,6-H in Ph and 2,6-H in C$_6$H$_4$$^t$Bu), 7.42-7.39 (m, 2H, 7-H in $L^1$ and 7-H in $L^2$), 7.35-7.29 (m, 3H, 4-H in Ph, 3,5-H in C$_6$H$_4$$^t$Bu), 7.26 (d, J=7.5 Hz, 1H, 5-H in $L^1$), 7.14 (t, J=7.5 Hz, 1H, 6-H in $L^1$), 6.83 (s, 1H, 3-H in $L^1$), 6.44 (s, 1H, 3-H in $L^2$), 3.71 (s, 1H, 1-H in $L^1$), 3.67 (s, 1H, 1-H in $L^2$), 3.16 (m, 2H, OCH$_2$CHMe$_2$), 2.19 (s, 3H, 2-Me in $L^1$), 2.16 (s, 3H, 2-Me in $L^2$), 1.67 (sept, J=6.6 Hz, 1H, OCH$_2$CHMe$_2$), 1.43 (s, 9H, 6-'Bu in L²), 1.38 (s, 9H, 'Bu in C₆H₄'Bu), 0.69 (d, J=6.8 Hz, 3H, OCH₂CHMeMe'), 0.65 (d, J=6.8 Hz, 3H, OCH₂CHMeMe'), −0.18 (s, 6H, SiMe₂).

Anti- and syn-dimethylsilanediyl[2-methyl-4-(4-tert-butylphenyl)-inden-1-yl](2-methyl-4-phenyl-5-isobutoxy-6-tert-butyl-inden-1-yl)zirconium dichloride (Metallocene E9)

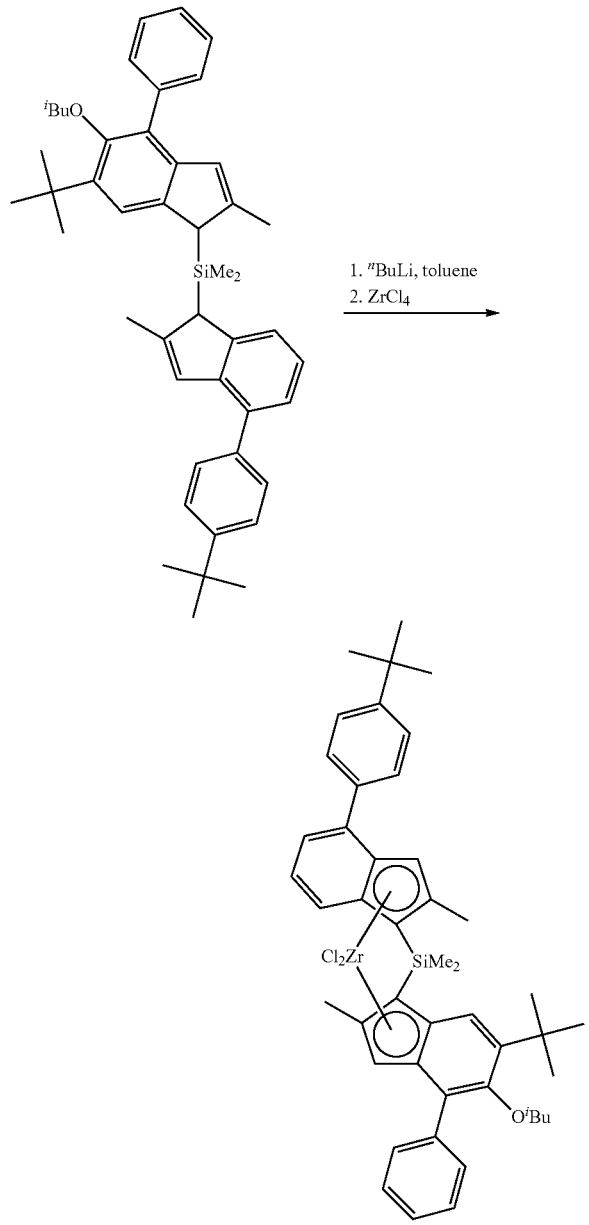

To a solution of 11.6 g (17.8 mmol) of (6-tert-butyl-5-isobutoxy-2-methyl-4-phenyl-1H-inden-1-yl) [4-(4-tert-butylphenyl)-2-methyl-1H-inden-1-yl]dimethylsilane in 200 ml of ether cooled to −30° C. 14.5 ml (36.3 mmol) of 2.5 M "BuLi in hexanes was added in one portion. This mixture was stirred overnight at room temperature, then cooled to −40° C., and 4.14 g (17.8 mmol) of ZrCl₄ was added. The reaction mixture was stirred for 24 h, then evaporated to dryness. The residue was dissolved in 300 ml of warm toluene, and the formed suspension was filtered through glass frit (G4) to give a solution which includes on the evidence of NMR spectroscopy a ca. 1 to 1 mixture of anti- and syn-zirconocenes. The filtrate was evaporated to 125 ml. Crystals precipitated at room temperature were collected, washed with 10 ml of toluene, 10 ml of n-hexane, and then dried in vacuum. This procedure gave 1.97 g (14%) of syn-zirconocene. The mother liquor was evaporated to dryness, and the residue was recrystallized from 80 ml of toluene. This procedure gave the precipitate A and mother liquor. On the evidence of NMR spectroscopy, this precipitate A consists of anti-complex contaminated with ca. 15% syn-metallocene. The mother liquor was evaporated to dryness, and the residue was recrystallized from 50 ml of toluene. This procedure gave some precipitate (consisting of syn-complex contaminated with several percents of anti-isomer) and mother liquor. This precipitate was recrystallyzed from 25 ml of toluene to give 1.34 g of pure syn-complex, and the mother liquor was evaporated to dryness, and the residue was recrystallized from 30 ml of toluene. The latter procedure gave a precipitate consisting of anti-complex contaminated with ca. 10% of syn-isomer. A mixture of this precipitate and precipitate A was recrystallized from 50 ml of a ca. 1 to 1 mixture of toluene and n-hexane to give 2.64 g of pure anti-complex. Thus, syn- and anti-metallocenes were isolated in 24 and 19% total yields, respectively. Assignment in NMR spectra was made using the following abbreviations: L¹ for 4-(4-tert-butylphenyl)-2-methyl-1H-inden-1-yl and L² for 6-tert-butyl-5-isobutoxy-2-methyl-4-phenyl-1H-inden-1-yl.

anti-Zirconocene.

Anal. calc. for C₄₆H₅₄Cl₂OSiZr: C, 67.95; H, 6.69. Found: C, 68.09; H, 6.57.

¹H NMR (CDCl₃): δ 7.63-7.52 (m, 6H, 2,6-H in Ph, 2,6-H in C₆H₄'Bu, 7-H in L¹ and 7-H in L²), 7.46 (d, J=8.1 Hz, 2H, 3,5-H in C₆H₄'Bu), 7.40-7.36 (m, 3H, 3,5-H in Ph and 5-H in L¹), 7.30 (m, 1H, 4-H in Ph), 7.10-7.06 (m, 1H, 6-H in L¹), 7.01 (s, 1H, 3-H in L¹), 6.56 (s, 1H, 3-H in L²), 3.40 (m, 1H, CHH'CHMe₂), 3.28-3.24 (m, 1H, CHH'CHMe₂), 2.24 (s, 3H, 2-Me in L¹), 2.17 (s, 3H, 2-Me in L²), 1.77-1.67 (m, 1H, CH₂CHMe₂), 1.40 (s, 9H, 'Bu in C₆H₄'Bu), 1.33-1.30 (m, 15H, 6-'Bu in L², SiMeMe' and SiMeMe'), 0.70 (d, J=6.6 Hz, 3H, CH₂CHMeMe'), 0.65 (d, J=6.6 Hz, 3H, CH₂CHMeMe').

syn-Zirconocene.

Anal. calc. for C₄₆H₅₄Cl₂OSiZr: C, 67.95; H, 6.69. Found: C, 68.21; H, 6.90.

¹H NMR (CDCl₃): δ 7.64 (d, J=8.6 Hz, 1H, 7-H in L¹), 7.58 (d, J=8.2 Hz, 2H, 2,6-H in C₆H₄'Bu), 7.55 (s, 1H, 7-H in L²), 7.50 (br. s, 2H, 2,6-H in Ph), 7.46 (d, J=8.2 Hz, 2H, 3,5-H in C₆H₄'Bu), 7.38 (br. s, 2H, 3,5-H in Ph), 7.30-2.27 (m, 1H, 4-H in Ph), 7.15 (d, J=7.0 Hz, 1H, 5-H in L¹), 6.91 (s, 1H, 3-H in L¹), 6.86 (dd, J=8.6 Hz, J=7.0 Hz, 1H, 6-H in L¹), 6.45 (s, 1H, 3-H in L²), 3.11 (d, J=6.9 Hz, 2H, CH₂CHMe₂), 2.43 (s, 3H, 2-Me in L¹), 2.37 (s, 3H, 2-Me in L²), 1.63-1.52 (m, 1H, CH₂CHMe₂), 1.44 (s, 3H, SiMeMe'), 1.35 (s, 9H, 'Bu in C₆H₄'Bu), 1.33 (s, 9H, 6-'Bu in L²), 1.22 (s, 3H, SiMeMe'), 0.61 (d, J=6.7 Hz, 3H, CH₂CHMeMe'), 0.55 (d, J=6.7 Hz, 3H, CH₂CHMeMe').

Preparation of the Solid Catalysts

Catalyst E1

Inside the glovebox, 80 µL of a dry and degassed mixture of perfluoroalkylethyl acrylate ester were mixed in a septum vial with 2 mL of a 30 wt-% solution of MAO in toluene and left to react overnight. The following day, 58.9 mg of the metallocene E1 of the invention (rac-anti-Me₂Si(2-Me-4-Ph-6- tBu-Ind)(2-Me-4-Ph-5-OMe-6-tBu-Ind)ZrCl$_2$) (0.076 mmol, 1 equivalent) were dissolved with 4 mL of the MAO solution in another septum bottle and left to stir inside the glovebox. After 60 minutes, the 4 mL of the MAO-metallocene solution and 1 mL of the perfluoroalkylethyl acrylate ester mixture in MAO solution were successively added into a 50 mL emulsification glass reactor containing 40 mL of hexadecafluoro-1,3-dimethylcyclohexane kept at −10° C. and equipped with an overhead stirrer (stirring speed=600 rpm). Total amount of MAO is 5 mL (300 equivalents). A red emulsion formed immediately and was stirred during 15 minutes at 0° C./600 rpm. Then the emulsion was transferred via a 2/4 teflon tube to 100 mL of hot hexadecafluoro-1,3-dimethylcyclohexane heated to 90° C., and stirred at 600 rpm until the transfer is completed. The speed was reduced to 300 rpm. After 15 minutes stirring, the oil bath was removed and the stirrer turned off. The catalyst was left to settle up on top of the hexadecafluoro-1,3-dimethylcyclohexane and after 35 minutes the solvent was siphoned off. The remaining red catalyst was dried during 2 hours at 50° C. over an argon flow. 0.62 g (catalyst E1) of a red free flowing powder was obtained.

Catalyst E2

Inside the glovebox, 80 μL of a dry and degassed mixture of perfluoroalkylethyl acrylate ester were mixed in a septum vial with 2 mL of a 30 wt-% solution of MAO in toluene and left to react overnight. The following day, 58.7 mg of the metallocene E2 of the invention (rac-anti-Me$_2$Si(2-Me-4-(p-tBuPh)-Ind)(2-Me-4-Ph-5-OMe-6-tBu-Ind)ZrCl$_2$) (0.076 mmol, 1 equivalent) were dissolved with 4 mL of the MAO solution in another septum bottle and left to stir inside the glovebox. After 60 minutes, the 4 mL of the MAO-metallocene solution and 1 mL of the perfluoroalkylethyl acrylate ester mixture in MAO solution were successively added into a 50 mL emulsification glass reactor containing 40 mL of hexadecafluoro-1,3-dimethylcyclohexane kept at −10° C. and equipped with an overhead stirrer (stirring speed=600 rpm). Total amount of MAO is 5 mL (300 equivalents). A red emulsion formed immediately and was stirred during 15 minutes at 0° C./600 rpm. Then the emulsion was transferred via a 2/4 teflon tube to 100 mL of hot hexadecafluoro-1,3-dimethylcyclohexane heated to 90° C., and stirred at 600 rpm until the transfer is completed. The speed was reduced to 300 rpm. After 15 minutes stirring, the oil bath was removed and the stirrer turned off. The catalyst was left to settle up on top of the hexadecafluoro-1,3-dimethylcyclohexane and after 35 minutes the solvent was siphoned off. The remaining red catalyst was dried during 2 hours at 50° C. over an argon flow. 0.52 g (catalyst E2) of a red free flowing powder was obtained.

Catalyst E3

Inside the glovebox, 80 μL of a dry and degassed mixture of perfluoroalkylethyl acrylate ester were mixed in a septum vial with 2 mL of a 30 wt-% solution of MAO in toluene and left to react overnight. The following day, 67.1 mg of the metallocene E3 of the invention (rac-anti-Me$_2$Si(2-Me-4-(3,5-di-tBuPh)-6-tBu-Ind)(2-Me-4-Ph-5-OMe-6-tBu-Ind)ZrCl$_2$) (0.076 mmol, 1 equivalent) were dissolved with 4 mL of the MAO solution in another septum bottle and left to stir inside the glovebox. After 60 minutes, the 4 mL of the MAO-metallocene solution and 1 mL of the perfluoroalkylethyl acrylate ester mixture in MAO solution were successively added into a 50 mL emulsification glass reactor containing 40 mL of hexadecafluoro-1,3-dimethylcyclohexane kept at −10° C. and equipped with an overhead stirrer (stirring speed=600 rpm). Total amount of MAO is 5 mL (300 equivalents). A red emulsion formed immediately and was stirred during 15 minutes at 0° C./600 rpm. Then the emulsion was transferred via a 2/4 teflon tube to 100 mL of hot hexadecafluoro-1,3-dimethylcyclohexane heated to 90° C., and stirred at 600 rpm until the transfer is completed. The speed was reduced to 300 rpm. After 15 minutes stirring, the oil bath was removed and the stirrer turned off. The catalyst was left to settle up on top of the hexadecafluoro-1,3-dimethylcyclohexane and after 35 minutes the solvent was siphoned off. The remaining red catalyst was dried during 2 hours at 50° C. over an argon flow. 0.67 g (catalyst E3) of a red free flowing powder was obtained.

Catalyst E5

Inside the glovebox, 80 μL of a dry and degassed mixture of perfluoroalkylethyl acrylate ester were mixed in a septum vial with 2 mL of a 30 wt-% solution of MAO in toluene and left to react overnight. The following day, 63.9 mg of the metallocene E5 of the invention (rac-anti-Me$_2$Si(2-Me-4-(3,5-tBu2Ph)-7-Me-Ind)(2-Me-4-Ph-5-OMe-6-tBu-Ind)ZrCl$_2$) (0.076 mmol, 1 equivalent) were dissolved with 4 mL of the MAO solution in another septum bottle and left to stir inside the glovebox. After 60 minutes, the 4 mL of the MAO-metallocene solution and 1 mL of the perfluoroalkylethyl acrylate ester mixture in MAO solution were successively added into a 50 mL emulsification glass reactor containing 40 mL of hexadecafluoro-1,3-dimethylcyclohexane kept at −10° C. and equipped with an overhead stirrer (stirring speed=600 rpm). Total amount of MAO is 5 mL (300 equivalents). A red emulsion formed immediately and was stirred during 15 minutes at 0° C./600 rpm. Then the emulsion was transferred via a 2/4 teflon tube to 100 mL of hot hexadecafluoro-1,3-dimethylcyclohexane heated to 90° C., and stirred at 600 rpm until the transfer is completed. The speed was reduced to 300 rpm. After 15 minutes stirring, the oil bath was removed and the stirrer turned off. The catalyst was left to settle up on top of the hexadecafluoro-1,3-dimethylcyclohexane and after 35 minutes the solvent was siphoned off. The remaining red catalyst was dried during 2 hours at 50° C. over an argon flow. 0.38 g (catalyst E5) of a red free flowing powder was obtained.

Catalyst E6

Inside the glovebox, 80 μL of a dry and degassed mixture of perfluoroalkylethyl acrylate ester were mixed in a septum vial with 2 mL of a 30 wt-% solution of MAO in toluene and left to react overnight. The following day, 65.2 mg of the metallocene E6 of the invention (rac-anti-Me$_2$Si(2-Me-4-(3,5-tBu2Ph)-7-OMe-Ind)(2-Me-4-Ph-5-OMe-6-tBu-Ind)ZrCl$_2$) (0.076 mmol, 1 equivalent) were dissolved with 4 mL of the MAO solution in another septum bottle and left to stir inside the glovebox. After 60 minutes, the 4 mL of the MAO-metallocene solution and 1 mL of the perfluoroalkylethyl acrylate ester mixture in MAO solution were successively added into a 50 mL emulsification glass reactor containing 40 mL of hexadecafluoro-1,3-dimethylcyclohexane kept at −10° C. and equipped with an overhead stirrer (stirring speed=600 rpm). Total amount of MAO is 5 mL (300 equivalents). A red emulsion formed immediately and was stirred during 15 minutes at 0° C./600 rpm. Then the emulsion was transferred via a 2/4 teflon tube to 100 mL of hot hexadecafluoro-1,3-dimethylcyclohexane heated to 90° C., and stirred at 600 rpm until the transfer is completed. The speed was reduced to 300 rpm. After 15 minutes stirring, the oil bath was removed and the stirrer turned off. The catalyst was left to settle up on top of the hexadecafluoro-1,3-dimethylcyclohexane and after 35 minutes the solvent was siphoned off. The remaining red catalyst was dried during 2 hours at 50° C. over an argon flow. 0.39 g (catalyst E6) of a red free flowing powder was obtained.

Catalyst E7

Inside the glovebox, 80 µL of a dry and degassed mixture of perfluoroalkylethyl acrylate ester were mixed in a septum vial with 2 mL of a 30 wt-% solution of MAO in toluene and left to react overnight. The following day, 66.3 mg of the metallocene E7 of the invention (rac-anti-Me$_2$Si(2-Me-4-(p-tBuPh)-Ind)(2-Me-4-(p-tBuPh)-5-OMe-6-tBu-Ind)ZrCl$_2$) (0.076 mmol, 1 equivalent) were dissolved with 4 mL of the MAO solution in another septum bottle and left to stir inside the glovebox. After 60 minutes, the 4 mL of the MAO-metallocene solution and 1 mL of the perfluoroalkylethyl acrylate ester mixture in MAO solution were successively added into a 50 mL emulsification glass reactor containing 40 mL of hexadecafluoro-1,3-dimethylcyclohexane kept at −10° C. and equipped with an overhead stirrer (stirring speed=600 rpm). Total amount of MAO is 5 mL (300 equivalents). A red emulsion formed immediately and was stirred during 15 minutes at 0° C./600 rpm. Then the emulsion was transferred via a 2/4 teflon tube to 100 mL of hot hexadecafluoro-1,3-dimethylcyclohexane heated to 90° C., and stirred at 600 rpm until the transfer is completed. The speed was reduced to 300 rpm. After 15 minutes stirring, the oil bath was removed and the stirrer turned off. The catalyst was left to settle up on top of the hexadecafluoro-1,3-dimethylcyclohexane and after 35 minutes the solvent was siphoned off. The remaining red catalyst was dried during 2 hours at 50° C. over an argon flow. 0.31 g (catalyst E7) of a red free flowing powder was obtained.

Catalyst E8

Inside the glovebox, 80 µL of a dry and degassed mixture of perfluoroalkylethyl acrylate ester were mixed in a septum vial with 2 mL of a 30 wt-% solution of MAO in toluene and left to react overnight. The following day, 67.1 mg of the metallocene E8 of the invention (rac-anti-Me$_2$Si(2-Me-4-(p-tBuPh)-Ind)(2-Me-4-(3,5-tBu2Ph)-5-OMe-6-tBu-Ind)ZrCl$_2$) (0.076 mmol, 1 equivalent) were dissolved with 4 mL of the MAO solution in another septum bottle and left to stir inside the glovebox. After 60 minutes, the 4 mL of the MAO-metallocene solution and 1 mL of the perfluoroalkylethyl acrylate ester mixture in MAO solution were successively added into a 50 mL emulsification glass reactor containing 40 mL of hexadecafluoro-1,3-dimethylcyclohexane kept at −10° C. and equipped with an overhead stirrer (stirring speed=600 rpm). Total amount of MAO is 5 mL (300 equivalents). A red emulsion formed immediately and was stirred during 15 minutes at 0° C./600 rpm. Then the emulsion was transferred via a 2/4 teflon tube to 100 mL of hot hexadecafluoro-1,3-dimethylcyclohexane heated to 90° C., and stirred at 600 rpm until the transfer is completed. The speed was reduced to 300 rpm. After 15 minutes stirring, the oil bath was removed and the stirrer turned off. The catalyst was left to settle up on top of the hexadecafluoro-1,3-dimethylcyclohexane and after 35 minutes the solvent was siphoned off. The remaining red catalyst was dried during 2 hours at 50° C. over an argon flow. 0.49 g (catalyst E8) of a red free flowing powder was obtained.

Catalyst E9

Inside the glovebox, 80 µL of a dry and degassed mixture of perfluoroalkylethyl acrylate ester were mixed in a septum vial with 2 mL of a 30 wt-% solution of MAO in toluene and left to react overnight. The following day, 61.7 mg of the metallocene E9 of the invention (rac-anti-Me$_2$Si(2-Me-4-(p-tBuPh)-Ind)(2-Me-4-Ph-5-OiBu-6-tBu-Ind)ZrCl$_2$) (0.076 mmol, 1 equivalent) were dissolved with 4 mL of the MAO solution in another septum bottle and left to stir inside the glovebox. After 60 minutes, the 4 mL of the MAO-metallocene solution and 1 mL of the perfluoroalkylethyl acrylate ester mixture in MAO solution were successively added into a 50 mL emulsification glass reactor containing 40 mL of hexadecafluoro-1,3-dimethylcyclohexane kept at −10° C. and equipped with an overhead stirrer (stirring speed=600 rpm). Total amount of MAO is 5 mL (300 equivalents). A red emulsion formed immediately and was stirred during 15 minutes at 0° C./600 rpm. Then the emulsion was transferred via a 2/4 teflon tube to 100 mL of hot hexadecafluoro-1,3-dimethylcyclohexane heated to 90° C., and stirred at 600 rpm until the transfer is completed. The speed was reduced to 300 rpm. After 15 minutes stirring, the oil bath was removed and the stirrer turned off. The catalyst was left to settle up on top of the hexadecafluoro-1,3-dimethylcyclohexane and after 35 minutes the solvent was siphoned off. The remaining red catalyst was dried during 2 hours at 50° C. over an argon flow. 0.33 g (catalyst E9) of a red free flowing powder was obtained.

Comparative Catalyst C1:

Comparative example catalyst C1 was synthesized according to the above described recipe with 78.2 mg of rac-methyl (cyclohexyl)silanediylbis[2-methyl-4-(4-tert-butylphenyl) indenyl]zirconium dichloride as the metallocene.

Comparative Catalyst C2:

Comparative example catalyst C2 was synthesized according to the above described recipe with 60.6 mg of rac-Me$_2$Si (2-Me-4-Ph-5-OMe-6-tBu-Ind)$_2$ZrCl$_2$ as the metallocene.

TABLE 1

| | Catalyst composition as determined by ICP | | |
| Cat. | Al (%) | Zr (%) | Al/Zr (molar) |
| --- | --- | --- | --- |
| E1 | 26.20 | 0.31 | 285 |
| E2 | 18.90 | 0.24 | 266 |
| E3 | 26.10 | 0.32 | 276 |
| E5 | 26.70 | 0.35 | 258 |
| E6 | 23.50 | 0.28 | 283 |
| E7 | 30.20 | 0.35 | 291 |
| E8 | 28.30 | 0.34 | 281 |
| E9 | 28.30 | 0.35 | 273 |
| C1 | 31.00 | 0.37 | 283 |
| C2 | 23.5 | 0.22 | 248 |

E1P, E2P, E3P and C1P: off-line prepolymerization of catalysts E1, E2, E3 and C1

The catalysts of the invention E1, E2 and E3 as well comparative catalyst C1 were pre-polymerised according to the following procedure: off-line prepolymerisation experiments were done in a 125 mL pressure reactor equipped with gas-feeding lines and an overhead stirrer. Dry and degassed hexadecafluoro-1,3-dimethylcyclohexane (15 mL) and the desired amount of the red catalyst to be pre-polymerised were loaded into the reactor inside a glovebox and the reactor was sealed. The reactor was then taken out from the glovebox and placed inside a water cooled bath. The overhead stirrer and the feeding lines were then connected. The feeding line was pressurized with hydrogen, and the experiment was started by opening the valve between the $H_2$ feed line and the reactor. At the same time propylene feed was started through the same $H_2$ feeding line in order to ensure that all the hydrogen would be fed into the reactor. The propylene feed was left open, and the monomer consumption was compensated by keeping the total pressure in the reactor constant (about 5 barg). The experiment was continued until a polymerisation time sufficient to provide the desired degree of polymerisation. The reactor was then taken back inside the glovebox before opening and the content was poured into a glass vessel. The hexadecafluoro-1,3-dimethylcyclohexane was evaporated until a constant weight was obtained to yield a pre-polymerised pink catalyst. The degree of polymerisation was determined gravimetrically and/or by analysis of the ash and/or aluminium content of the catalyst to be 3.5 for E1P, 4.6 for E2P, 2.9 for E3P and 3.1 for C1P.

Polymerisations:

Homopolymerisation of Propylene with Catalysts E1 to E3 and $C_2/C_3$ Random Copolymerisation with Catalysts E1 to E3 and E7

The polymerisations were performed in a 5 L reactor. 200 µl of triethylaluminum was fed as a scavenger in 5 mL of dry and degassed pentane. The desired amount of hydrogen was then loaded (measured in mmol) and 1100 g of liquid propylene was fed into the reactor. Desired amount of ethylene was fed into the reactor (random copolymerisations). The temperature was set to 30° C. The desired amount of catalyst in 5 mL of hexadecafluoro-1,3-dimethylcyclohexane was flushed into the reactor with a nitrogen overpressure. The temperature was then raised to 70° C. over a period of 15 minutes. The polymerisation was stopped after 30 minutes by venting the reactor and flushing with nitrogen before the polymer was collected. The catalyst activity was calculated on the basis of the 30 minutes period.

Homopolymerisation of Propylene with Catalysts E5 to E9

The polymerisations were performed in a 5 L reactor. 200 µl of triethylaluminum was fed as a scavenger in 5 mL of dry and degassed pentane. The desired amount of hydrogen was then loaded (measured in mmol) and 1100 g of liquid propylene was fed into the reactor. The temperature was set to 20° C. The desired amount of catalyst in 5 mL of hexadecafluoro-1,3-dimethylcyclohexane was flushed into the reactor with a nitrogen overpressure. After 5 minutes (prepolymerisation) the temperature was then raised to 70° C. over a period of 15 minutes. The polymerisation was stopped after 60 minutes by venting the reactor and flushing with nitrogen before the polymer was collected. The catalyst activity was calculated on the basis of the 60 minutes period.

Catalyst activity for catalysts E1-E3 and E5-E9 was determined according to:

Activity kg/g(cat)/h=amount of polymer produced in kg/(catalyst loading in grams×polymerization time in hours)

Polymerisation details and results are disclosed in Table 2 (Ex 1-26 and c-1-c-10) and Table 3 (Ex 27-34 and c-11-c-13)

Heterophasic Ethylene-Propylene Copolymerization with Catalyst E1P.

Heterophasic copolymer was prepared with catalyst E1P in a sequential bulk/gas phase process as follows: A 21.2 L autoclave with double helix stirrer containing ~0.4 barg propylene was filled with additional 5.18 kg propylene. After adding 0.2 NL $H_2$ and 0.97 mmol triethylaluminium (1 molar solution in hexane) using a stream of 248 g propylene, the solution was stirred at 250 rpm. After 20 min the reactor temperature was increased to 40° C. and 298 mg of the solid, pre-polymerized catalyst E1P was contacted with 5 ml perfluoro-1,3-dimethylcyclohexane under $N_2$ pressure (0.003 mol at ~10 barg) in a stainless-steel vial connected to the autoclave for 60 sec and flushed into the reactor with 494 g propylene. After that the stirring speed was increased to 350 rpm and the temperature in the reactor increased to 70° C. over ~13 min. This temperature was held for 30 min after achieving 68° C. After that the pressure was decreased to 1 bar-a via flashing. To achieve target conditions for gas phase of 15 bar-g at 60° C., ethylene and propylene are dosed in a ratio of C3/C2=1.26 g/g into the reactor until a total amount of 429 g over 8 min. 60° C. (temperature decreased during flashing because of vaporization enthalpy) was achieved 16 min after start of pressure increase and the total pressure was constantly held at 15 bar-g via dosing ethylene and propylene in a ratio of C3/C2=1.83 g/g. The polymerisation was stopped 67 min after start of pressure increase to 15 barg via flashing and cooling. The residence time used for calculation of catalyst activity in gas phase was 55.5 min (start after achieving of polymerisation temperature of 58° C. in gas phase).

After 3 times spilling the reactor with $N_2$ and one vacuum/$N_2$ cycle the product was taken out and dried overnight in a hood and additionally 2 hours in a vacuum drying oven at 60° C.

Heterophasic Ethylene-Propylene Copolymerization with Catalyst E2P

Heterophasic copolymer was prepared with catalyst E2P in a sequential bulk/gas phase process as follows: A 21.2 L autoclave with double helix stirrer containing ~0.5 barg propylene was filled with additional 3.97 kg propylene. After adding 0.2 NL hydrogen and 0.73 mmol triethylaluminium (1 molar solution in hexane) using a stream of 246 g propylene the solution was stirred at 250 rpm. After 20 min the reactor temperature was increased to 40° C. and 253 mg of the solid, pre-polymerized catalyst E2P (degree of polymerisation 4.6) was contacted with 5 ml perfluoro-1,3-dimethylcyclohexane under nitrogen-pressure (0.003 mol at ~10 bar-g) for 60 sec and spilled into the reactor with 243 g propylene. After that the stirring speed was increased to 350 rpm and the temperature in the reactor increased to 70° C. over ~17 min. This temperature was held for 30 mins after achieving 68° C. After that the pressure was decreased to 1.1 barg via flashing. To achieve target conditions for gas phase of ~15 barg at 60° C., ethylene and propylene are dosed in a ratio of C3/C2=1.23 g/g into the reactor until a total amount of 406 g over 8 min. 60° C. (temperature decreased during flashing because of vaporization enthalpy) was achieved 14 min after start of pressure increase and the total pressure was constantly held at 15 barg via dosing ethylene and propylene in a ratio of C3/C2=1.83 g/g. The polymerisation was stopped 41.5 min after start of pressure increase to 15 barg via flashing and cooling. The residence time used for calculation of catalyst activity in gas phase was 27.5 min (start after achieving of polymerisation temperature of 58° C. in gas phase).

After 3 times spilling the reactor with nitrogen and one vacuum/nitrogen cycle the product is taken out and dried overnight in a hood and additionally 2 hours in a vacuum drying oven at 60° C.

This polymerisation was repeated using different amount of catalyst and C3/C2 feeds.

Heterophasic Ethylene-Propylene Copolymerization with Catalyst E3P. Heterophasic copolymer was prepared with catalyst E3P in a sequential bulk/gas phase process as follows: A 21.2 L autoclave with double helix stirrer containing ~0.5 barg propylene was filled with additional 3.96 kg propylene. After adding 0.2 NL hydrogen and 0.73 mmol triethylaluminium (1 molar solution in hexane) using a stream of 247 g propylene the solution was stirred at 250 rpm. After 20 min the reactor temperature was increased to 40° C. and 212 mg of the solid, pre-polymerized catalyst E3P (degree of polymerisation 2.9) was contacted with 5 ml perfluoro-1,3-dimethylcyclohexane under nitrogen-pressure (0.003 mol at ~10 bar-g) for 60 sec and spilled into the reactor with 242 g propylene. After that the stirring speed was increased to 350 rpm and the temperature in the reactor increased to 70° C. over ~15 min. This temperature was held for 30 mins after achieving 68° C. After that the pressure was decreased to 0.9 bara via flashing. To achieve target conditions for gas phase of ~15 barg at 60° C., ethylene and propylene are dosed in a ratio of C3/C2=0.4 g/g into the reactor until a total amount of 351 g over 8 min. 60° C. (temperature decreased during flashing because of vaporization enthalpy) was achieved 18 min after start of pressure increase and the total pressure was constantly held at 15 barg via dosing ethylene and propylene in a ratio of C3/C2=1 g/g. The polymerisation was stopped 93 min after start of pressure increase to 15 barg via flashing and cooling. The residence time used for calculation of catalyst activity in gas phase was 82 min (start after achieving of polymerisation temperature of 58° C. in gas phase).

After 3 times spilling the reactor with nitrogen and one vacuum/nitrogen cycle the product is taken out and dried overnight in a hood and additionally 2 hours in a vacuum drying oven at 60° C.

Heterophasic Ethylene-Propylene Copolymerisation with C1P (Comparative)

Batch production of a heterophasic ethylene copolymer with pre-polymerized comparison catalyst C1P in bulk/gas phase process: A stirred autoclave (double helix stirrer) with a volume of 21.2 dm$^3$ containing ~0.5 barg propylene was filled with additional 5.18 kg propylene. After adding 0.2 ln hydrogen and 0.97 mmol triethylaluminium (1 molar solution in hexane) using a stream of 244 g propylene the solution was stirred at 250 rpm. After 20 min the reactor temperature was increased to 40° C. and 494 mg of the solid, pre-polymerized catalyst C1P was contacted with 5 ml perfluoro-1,3-dimethylcyclohexane under nitrogen pressure (0.003 mol at ~10 barg) for 60 sec and spilled into the reactor with 491 g propylene. After that the stirring speed was increased to 350 rpm and the temperature in the reactor increased to 70° C. over ~17 min. This temperature was held for 30 min after achieving 68° C. After that the pressure is decreased to 1.1 barg via flashing. To achieve target conditions for gas phase of 15 barg at 60° C. ethylene and propylene are dosed in a ratio of C3/C2=1.23 g/g into the reactor until a total amount of 401 g over 8 min. 60° C. (temperature decreased during flashing because of vaporization enthalpy) was achieved 19 min after start of pressure increase and the total pressure was constantly held at 15 barg via dosing ethylene and propylene in a ratio of C3/C2=1.83 g/g. The polymerisation was stopped 103 min after start of pressure increase to 15 barg via flashing and cooling. The residence time used for calculation of catalyst activity in gas phase was 90 min (start after achieving of polymerisation temperature of 58° C. in gas phase).

After 3 times spilling the reactor with nitrogen and one vacuum/nitrogen cycle the product was taken out and dried over night in a hood and additionally 2 hours in a vacuum drying oven at 60° C.

Catalyst activity for E1P and E2P and E3P was determined according to:

Activity kg/g(cat)/h={amount of polymer produced in kg/[(prepolymerized catalyst loading in grams)× polymerization time in hours]}×(1+prepolymerization degree).

Results of heterophasic polymerisations are summarised in Tables 4 and 5. (Ex 35-42, c-14 and c-15)

TABLE 2

Homopolymerisation of propylene

| Cat. | Ex | Catalyst (mg) | H$_2$ (mmol) | Polym time (min) | Polymer (g) | Activity$^{(1)}$ (kg/g/h) | Activity$^{(2)}$ (kg/g$_{Zr}$/h) | MFR$_2$ (g/10 min) | MFR$_{21}$ (g/10 min) | M$_w$ (kg/mol) | M$_w$/M$_n$ | T$_m$ (° C.) |
|---|---|---|---|---|---|---|---|---|---|---|---|---|
| E1 | 1 | 11.7 | 1.0 | 30 | 126.0 | 21.6 | 6970 | — | 2.6 | 957 | 2.1 | 142.2 |
|  | 2 | 4.6 | 6.0 | 30 | 113.0 | 49.3 | 15891 | — | 56.0 | 424 | 2.3 | 144.0 |
|  | 3 | 8.7 | 15.0 | 30 | 245.0 | 56.2 | 18139 | 6.9 | — | 244 | 2.2 | 143.5 |
|  | 4 | 6.6 | 25.0 | 30 | 198.0 | 60.0 | 19345 | 36.0 | — | 154 | 2.6 | 142.9 |
| E2 | 5 | 20.3 | 1.0 | 30 | 191 | 18.8 | 7820 | — | 1.6 | 994 | 2.4 | 148.2 |
|  | 6 | 4.9 | 6.0 | 30 | 127 | 51.8 | 21582 | — | 19.0 | 549 | 2.4 | 147.5 |
|  | 7 | 12.1 | 15.0 | 30 | 414 | 68.4 | 28512 | 2.4 | — | 305 | 2.5 | 149.1 |
|  | 8 | 6.8 | 25.0 | 30 | 250 | 73.5 | 30637 | 14.0 | — | 188 | 3.1 | 148.2 |
| E3 | 9 | 13.6 | 1.0 | 30 | 123 | 18.0 | 5630 | — | 3.4 | 853 | 2.6 | 144.9 |
|  | 10 | 10.3 | 6.0 | 30 | 253 | 49.2 | 15376 | — | 78.0 | 404 | 2.7 | 146.9 |
|  | 11 | 7.3 | 15.0 | 30 | 235 | 64.5 | 20146 | 13.0 | — | 204 | 3.0 | 146.9 |
| E5 | 12 | 9.7 | 1.0 | 60 | 211 | 21.8 | 6221 | — | 10.0 | 545 | 2.2 | 147.4 |
|  | 13 | 10.9 | 6.0 | 60 | 452 | 41.4 | 11843 | — | 95.0 | 321 | 2.4 | 148.2 |
|  | 14 | 9.3 | 15.0 | 60 | 481 | 51.8 | 14786 | 9.0 | — | 221 | 2.3 | 148.2 |
| E6 | 15 | 16.3 | 1.0 | 60 | 188 | 11.6 | 4126 | — | 21.0 | 508 | 2.7 | 148.5 |
|  | 16 | 8.2 | 6.0 | 60 | 210 | 25.6 | 9151 | — | 110.0 | 337 | 2.5 | 151.2 |
|  | 17 | 6.5 | 15.0 | 60 | 183 | 28.1 | 10027 | 14.0 | — | 199 | 2.6 | 150.2 |
| E7 | 18 | 9.8 | 1.0 | 60 | 239 | 24.4 | 6980 | — | 3.0 | 817 | 2.2 | 148.0 |
|  | 19 | 9.8 | 6.0 | 60 | 479 | 48.8 | 13956 | — | 28.0 | 472 | 2.2 | 149.4 |
|  | 20 | 6.1 | 15.0 | 60 | 394 | 64.6 | 18454 | 3.6 | — | 274 | 2.2 | 150.3 |
| E8 | 21 | 12.7 | 1.0 | 60 | 209 | 16.4 | 4838 | — | 5.4 | 711 | 2.7 | 151.5 |
|  | 22 | 10.0 | 6.0 | 60 | 309 | 30.9 | 9088 | — | 43.0 | 418 | 2.7 | 151.6 |
|  | 23 | 10.0 | 15.0 | 60 | 410 | 41.0 | 12068 | 5.0 | — | 270 | 2.6 | 152.3 |
| E9 | 24 | 9.7 | 1.0 | 60 | 189 | 19.5 | 5561 | — | 2.5 | 791 | 2.3 | 147.1 |
|  | 25 | 9.8 | 6.0 | 60 | 384 | 39.2 | 11198 | — | 27.0 | 485 | 2.1 | 147.2 |
|  | 26 | 9.7 | 15.0 | 60 | 425 | 43.8 | 12521 | 3.4 | — | 279 | 2.4 | 148.2 |

TABLE 2-continued

Homopolymerisation of propylene

| Cat. | Ex | Catalyst (mg) | H$_2$ (mmol) | Polym time (min) | Polymer (g) | Activity$^{(1)}$ (kg/g/h) | Activity$^{(2)}$ (kg/g$_{Zr}$/h) | MFR$_2$ (g/10 min) | MFR$_{21}$ (g/10 min) | M$_w$ (kg/mol) | M$_w$/M$_n$ | T$_m$ (° C.) |
|---|---|---|---|---|---|---|---|---|---|---|---|---|
| C1 | c-1 | 28.8 | 0.0 | 30 | 113 | 7.8 | 2121 | — | 5.9 | 757 | 2.3 | 149.2 |
|  | c-2 | 27.4 | 1.0 | 30 | 193 | 14.1 | 3807 | — | 12.5 | 665 | 2.5 | 149.4 |
|  | c-3 | 30.2 | 6.0 | 30 | 337 | 22.3 | 6032 | 1.3 | — | 416 | 2.1 | 150.6 |
|  | c-4 | 28.6 | 15.0 | 30 | 407 | 28.5 | 7692 | 12.3 | — | 222 | 2.4 | 151.0 |
|  | c-5 | 32.1 | 25.0 | 30 | 531 | 33.1 | 8942 | 32.8 | — | 168 | 2.3 | 150.9 |
|  | c-6 | 14.4 | 1.0 | 60 | 133 | 9.2 | 3173 | — | 10 | 560 | 2.7 | — |
|  | c-7 | 15.8 | 6.0 | 60 | 254 | 16.1 | 5541 | 1.8 | — | 312 | 2.5 | — |
|  | c-8 | 14.5 | 15.0 | 60 | 273 | 18.8 | 6495 | 15.0 | — | 202 | 2.5 | — |
| C2 | c-9 | 19.0 | 6.0 | 30 | 428 | 45.1 | 14079 | 0.33 | — | 524 | 2.6 | 143.3 |
|  | c-10 | 17.4 | 15.0 | 30 | 365 | 42.0 | 13111 | 3.9 | — | 275 | 3.3 | 144.4 |

$^{(1)}$Activity in kg of polymer per gram of catalyst per hour
$^{(2)}$Activity in kg of polymer per gram of Zirconium per hour

TABLE 3

C$_2$/C$_3$ random copolymerisation

| Cat | Ex | Catalyst (mg) | H$_2$ (mmol) | C$_2$ (g) | Polymer (g) | Activity (kg/g/h) | Activity (kg/g$_{Zr}$/h) | MFR$_2$ (g/10 min) | MFR$_{21}$ (g/10 min) | M$_w$ (kg/mol) | M$_w$/M$_n$ | FTIRC$_2$ (wt. %) | T$_m$ (° C.) |
|---|---|---|---|---|---|---|---|---|---|---|---|---|---|
| E1 | 27 | 5.4 | 6.0 | 7.1 | 129.0 | 47.8 | 15424 | — | 44.0 | 450 | 2.3 | 1.2 | 139.0 |
|  | 28 | 5.2 | 6.0 | 19.9 | 113.0 | 43.5 | 14032 | — | 65.0 | 422 | 2.2 | 2.2 | 131.6 |
| E2 | 29 | 5.1 | 6.0 | 19.9 | 149.0 | 58.5 | 24379 | — | 18.0 | 538 | 2.4 | 2.0 | 135.2 |
|  | 30 | 10.0 | 6.0 | 40.2 | 193.0 | 38.6 | 16092 | — | 19.0 | 516 | 2.4 | 3.1 | 124.2 |
|  | 31 | 15.0 | 6.0 | 49.9 | 236.0 | 31.4 | 13094 | — | 21.0 | 504 | 2.6 | 3.9 | 119.3 |
| E3 | 32 | 8.7 | 6.0 | 20.2 | 324.0 | 74.4 | 23240 | — | 66.0 | 395 | 2.5 | 1.9 | 133.7 |
|  | 33 | 8.9 | 6.0 | 30.0 | 261.0 | 58.7 | 18343 | — | 67.0 | 409 | 2.5 | 3.3 | 127.2 |
| E7 | 34 | 8.3 | 6.0 | 20.0 | 329.0 | 79.3 | 22657 | — | 24.0 | 482 | 2.2 | 1.4 | 136.5 |
| C1 | c-11 | 5.3 | 6.0 | 20.0 | 112.5 | 42.5 | 12129 | 2.50 | — | 324 | 2.2 | 1.4 | 138.4 |
|  | c-12 | 6.5 | 6.0 | 39.9 | 73.0 | 22.5 | 6418 | 3.40 | — | 288 | 2.1 | 3.0 | 128.6 |
|  | c-13 | 8.0 | 6.0 | 50.3 | 72.8 | 18.2 | 5200 | 3.80 | — | 276 | 2.2 | 4.0 | 122.4 |

TABLE 4

Heterophasic ethylene-polypropylene copolymerisations

| Ex | Cat. | Prepoly'd Catalyst amount (mg) | Total polymer yield (g) | Polym Yield in bulk (g) | Activity in bulk kgPP/(g cat*h) | C3/C2 in feed (transition gas phase) (g/g) | C3/C2 in feed (gas phase) (g/g) | Residence time (gas phase) (min) | Polym Yield in gas phase (g) | Activity in gas phase kg/g(cat)*h |
|---|---|---|---|---|---|---|---|---|---|---|
| c-14 | C1P | 494 | 915 | 601 | 10.0 | 1.23 | 1.83 | 90 | 314 | 1.74 |
| 35 | E1P | 298 | 1301 | 787 | 23.8 | 1.26 | 1.83 | 55.5 | 514 | 8.39 |
| 36 | E2P | 257 | 680 | 483 | 21.0 | 0.40 | 1.00 | 22.5 | 197 | 11.45 |
| 37 | E2P | 253 | 692 | 428 | 18.9 | 1.23 | 1.83 | 27.5 | 264 | 12.75 |
| 38 | E3P | 212 | 1100 | 762 | 28.0 | 0.4 | 1.00 | 82 | 338 | 4.6 |

(1) Activity in kg of polymer per gram of catalyst per hour

TABLE 5

Heterophasic ethylene-polypropylene copolymerisations-polymer properties

| Ex | Cat. | MFR$_2$ (g/10 min) | C2 in XS (IR) wt % | XS wt-% | IV(XS) dL/g | G'23° C. Mpa | Tg(EPR) | M$_w$ at the max of MWD curve of the C2C3 copolymer kg/mol | M$_w$ (XS) kg/mol |
|---|---|---|---|---|---|---|---|---|---|
| c-14 | C1P | 2.43 | 23.3 | 34.3 | 0.58 | 228 | −38.6 | 47 | 41 |
| 35 | E1P | 0.47 | 23 | 38 | 1.15 | 185 | −38 | 94 | 94 |
| 36 | E2P | 0.07 | 43.3 | 28.6 | 1.26 | 311 | −54 | 140 | 101 |
| 37 | E2P | 0.15 | 22.3 | 35 | 1.24 | 222 | −36 | 129 | 111 |
| 38 | E3P | 0.35 | 39.9 | 35.2 | 1.55 | 271 | −52 | 146 | 125 |

Comments

The polymerisation behaviour of catalysts E1 to E3 and E5 to E9 was assessed against reference catalysts C1 and C2 prepared similarly to catalysts E1-E3 and E5-E9 (see Table 1). The propylene polymerisation experiments carried out with the new metallocene catalysts clearly show that the catalysts of the invention E1 to E3 outperform both catalysts C1 and C2 in polymerisation activity and the catalysts of the invention E5 to E9 outperform catalyst C1 in polymerisation activity (see Table 2). Importantly, in the low MFR (higher molecular weight) range, catalysts E1 to E3 and E5 to E9 provide significantly higher activities than catalyst C1, while in the high MFR range (lower molecular weight), catalysts E1, E2 and E3 provide significantly higher activities than both catalysts C1 and C2 and catalysts E5 to E9 significantly higher activities than C1.

The second set of polymerisation experiments focused on investigating the ethylene response and molecular weight capability of catalysts E1 to E3 in random copolymerisation. The random copolymerisation behaviour of catalysts E1, E2 and E3 was assessed against catalyst C1 (Table 3). For similar ethylene incorporation, the catalysts of some examples show higher polymerisation activity with respect to catalyst C1. Importantly, the weight average molecular weight Mw does not show a strong negative correlation with increasing ethylene feed with catalysts E1, E2 and E3 as it is witnessed with catalyst C1. This indicates a reduced tendency of chain transfer to ethylene. Another significant difference is the superior conversion of ethylene with catalysts E1, E2 and E3. For the same ethylene content, catalyst E7 shows a better C2 randomization, as deduced by the lower melting point (compare c-11 to the Ex 34).

In gas phase copolymerization we obtain much higher activities and higher copolymer molecular weights with the catalysts of certain examples compared to the catalyst known in the art.

The invention claimed is:

1. A racemic complex of formula (I)

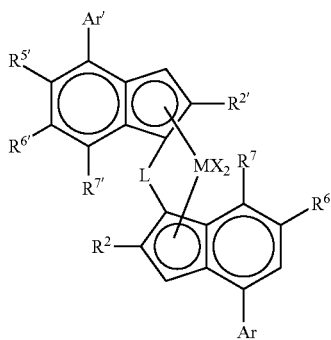

wherein
M is zirconium or hafnium;
each X is a sigma ligand;
L is a divalent bridge selected from —R'$_2$C—, —R'$_2$C—CR'$_2$—, —R'$_2$Si—, —R'$_2$Si—SiR'$_2$—, —R'$_2$Ge—, wherein each R' is independently a hydrogen atom, $C_{1-20}$-hydrocarbyl, tri($C_{1-20}$-alkyl)silyl, $C_{6-20}$-aryl, $C_{7-20}$-arylalkyl or $C_{7-20}$-alkylaryl;
$R^2$ and $R^{2'}$ are each independently a $C_{1-20}$ hydrocarbyl radical optionally containing one or more heteroatoms from groups 14-16;
$R^{5'}$ is Z'R$^{3'}$ wherein Z' is O or S; and R$^{3'}$ is a $C_{1-10}$ hydrocarbyl group optionally substituted by one or more halo groups;

$R^6$ and $R^{6'}$ are each independently hydrogen or a $C_{1-20}$ hydrocarbyl group optionally containing one or more heteroatoms from groups 14-16;
$R^7$ and $R^{7'}$ are each independently hydrogen or $C_{1-20}$ hydrocarbyl group optionally containing one or more heteroatoms from groups 14-16;
Ar is independently an aryl or heteroaryl group having up to 20 carbon atoms optionally substituted by one or more groups $R^1$;
Ar' is independently an aryl or heteroaryl group having up to 20 carbon atoms optionally substituted by one or more groups $R^1$;
each $R^1$ is a $C_{1-20}$ hydrocarbyl group or two $R^1$ groups on adjacent carbon atoms taken together to form a fused 5 or 6 membered non aromatic ring with the Ar group, said ring being itself optionally substituted with one or more groups $R^4$; and
each $R^4$ is a $C_{1-20}$ hydrocarbyl group.

2. The complex of claim 1 being a racemic anti isomer.

3. The complex of claim 1, in which $R^7$ and $R^{7'}$ are hydrogen and $R^2$ and $R^{2'}$ are the same.

4. The complex of claim 1, wherein Ar and Ar' are different.

5. The complex of claim 1 of formula (II') or (II);

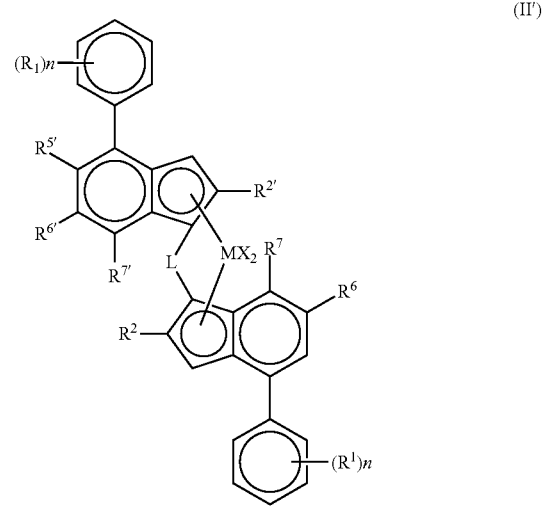

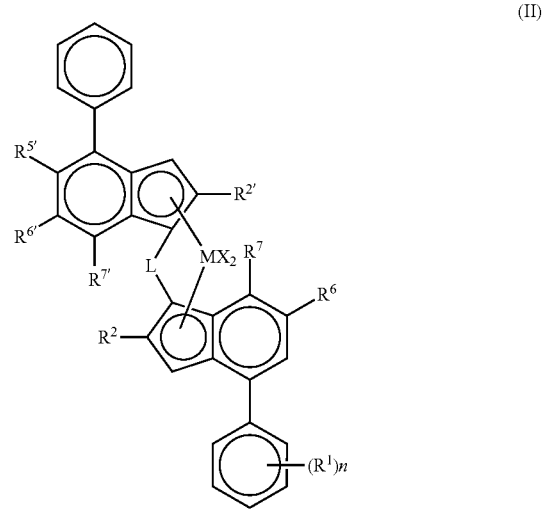

wherein
M is zirconium or hafnium;
each X is a sigma ligand;

L is a divalent bridge selected from —R'$_2$C—, —R'$_2$C—CR'$_2$—, —R'$_2$Si—, —R'$_2$Si—SiR'$_2$—, —R'$_2$Ge—, wherein each R' is independently a hydrogen atom, C$_{1-20}$ alkyl, C$_{3-10}$ cycloalkyl, tri(C$_{1-20}$-alkyl)silyl, C$_{6-20}$-aryl, C$_{7-20}$ arylalkyl or C$_{7-20}$ alkylaryl;
each R$^2$ or R$^{2'}$ is a C$_{1-10}$ alkyl group;
R$^{5'}$ is a Z'R$^{3'}$ group;
R$^6$ is hydrogen or a C$_{1-10}$ alkyl group;
R$^{6'}$ is a C$_{1-10}$ alkyl group or C$_{6-10}$ aryl group;
R$^7$ is hydrogen, a C$_{1-6}$ alkyl group or ZR$^3$ group;
R$^{7'}$ is hydrogen or a C$_{1-10}$ alkyl group;
Z and Z' are independently O or S;
R$^{3'}$ is a C$_{1-10}$ alkyl group, or a C$_{6-10}$ aryl group optionally substituted by one or more halo groups;
R$^3$ is a C$_{1-10}$-alkyl group;
n is 0 to 4, e.g. 0, 1 or 2;
and each R$^1$ is a C$_{1-20}$ hydrocarbyl group, e.g. C$_{1-10}$ alkyl group.

6. The complex of claim 1 of formula (III') or (III):

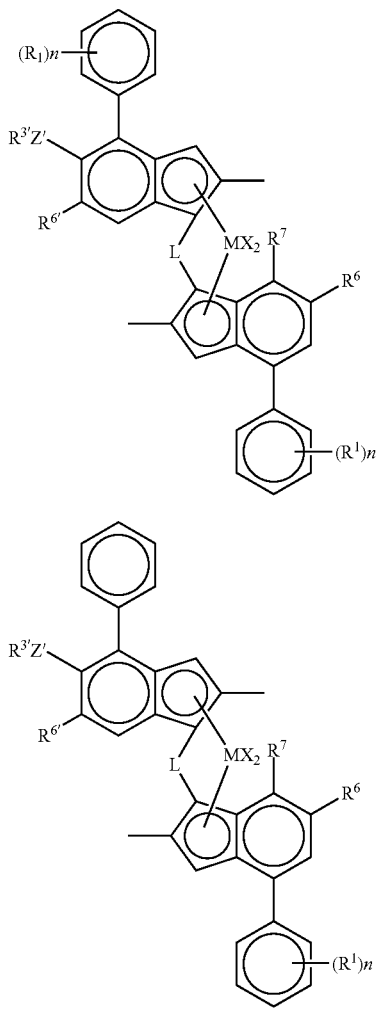

(III')

(III)

M is zirconium or hafnium;
each X is a sigma ligand;
L is a divalent bridge selected from —R'$_2$C— or —R'$_2$Si— wherein each R' is independently a hydrogen atom, C$_{1-20}$ alkyl or C$_{3-10}$ cycloalkyl;
R$^6$ is hydrogen or a C$_{1-10}$ alkyl group;
R$^{6'}$ is a C$_{1-10}$ alkyl group or C$_{6-10}$ aryl group;
R$^7$ is hydrogen, C$_{1-6}$ alkyl or OC$_{1-6}$ alkyl;
Z' is O or S;
R$^{3'}$ is a C$_{1-10}$ alkyl group, or C$_{6-10}$ aryl group optionally substituted by one or more halo groups;
n is 0 to 4, e.g. 0, 1 or 2; and
each R$^1$ is a C$_{1-10}$ alkyl group.

7. The complex of claim 1 of formula (IV') or (IV)

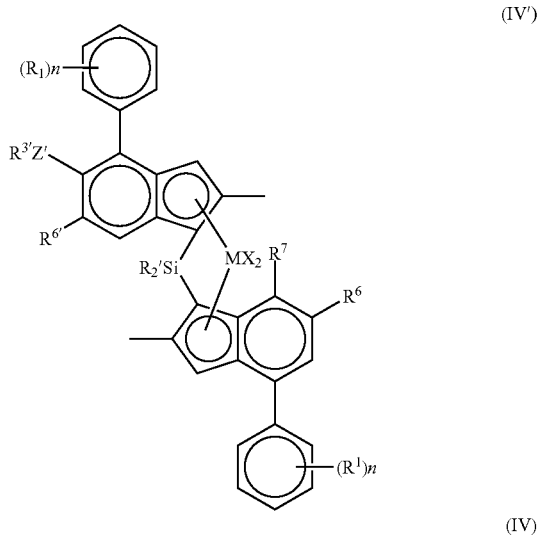

(IV')

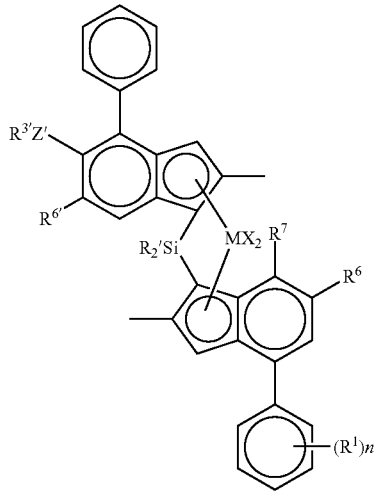

(IV)

M is zirconium or hafnium;
each X is a sigma ligand;
each R' is independently a hydrogen atom, C$_{1-20}$ alkyl or C$_{3-7}$ cycloalkyl;
R$^6$ is hydrogen or a C$_{1-10}$ alkyl group;
R$^{6'}$ is a C$_{1-10}$ alkyl group or C$_{6-10}$ aryl group;
R$^7$ is hydrogen, C$_{1-6}$ alkyl or OC$_{1-6}$ alkyl;
Z' is O or S;
R$^{3'}$ is a C$_{1-10}$ alkyl group, or C$_{6-10}$ aryl group optionally substituted by one or more halo groups;
n is 0, 1 to 2; and
each R$^1$ is a C$_{3-8}$ alkyl group.

8. The complex of claim 1 of formula (V) or (V')

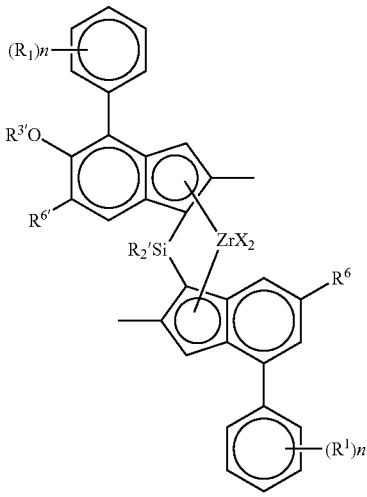 (V')

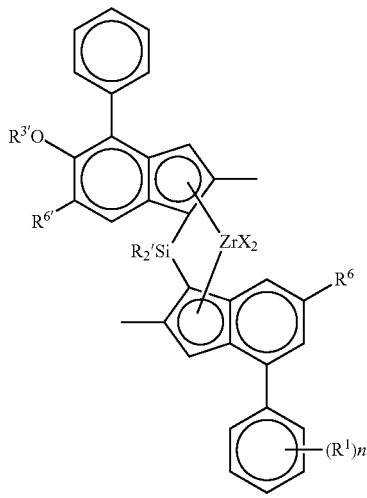 (V)

wherein each X is a sigma ligand;
R' is independently a $C_{1-6}$ alkyl or $C_{3-10}$ cycloalkyl;
$R^1$ is $C_{3-8}$ alkyl;
$R^6$ is hydrogen or a $C_{3-8}$ alkyl group;
$R^{6'}$ is a $C_{3-8}$ alkyl group or $C_{6-10}$ aryl group;
$R^{3'}$ is a $C_{1-6}$ alkyl group, or $C_{6-10}$ aryl group optionally substituted by one or more halo groups; and
n is 0, 1 or 2.

9. A catalyst comprising (i) a complex of formula (I) as claimed in claim 1 and (ii) a cocatalyst comprising a compound of a group 13 metal.

10. The catalyst of claim 9 obtainable by a process in which
   (a) a liquid/liquid emulsion system is formed, said liquid/liquid emulsion system comprising a solution of the catalyst components (i) and (ii) dispersed in a solvent so as to form dispersed droplets; and
   (b) solid particles are formed by solidifying said dispersed droplets.

11. A process for the manufacture of the catalyst as defined in claim 9, comprising obtaining a complex of formula (I) and a cocatalyst as defined in claim 9;
forming a liquid/liquid emulsion system, which comprises a solution of catalyst components (i) and (ii) dispersed in a solvent, and solidifying said dispersed droplets to form solid particles.

12. A process for the polymerisation of at least one olefin comprising reacting said at least one olefin with the catalyst as claimed in claim 9.

13. The complex of claim 5, wherein each X is independently a hydrogen atom, a halogen atom, $C_{1-6}$ alkoxy group, $C_{1-6}$ alkyl, phenyl or benzyl group.

14. The complex of claim 6, wherein each X is independently a hydrogen atom, a halogen atom, $C_{1-6}$ alkoxy group, $C_{1-6}$ alkyl, phenyl or benzyl group.

15. The complex of claim 7, wherein each X is independently a hydrogen atom, a halogen atom, $C_{1-6}$ alkoxy group, $C_{1-6}$ alkyl, phenyl or benzyl group.

16. The complex of claim 8, wherein each X is independently a hydrogen atom, a halogen atom, $C_{1-6}$ alkoxy group, $C_{1-6}$ alkyl, phenyl or benzyl group.

17. The catalyst of claim 9, wherein the cocatalyst is a compound of aluminum or boron.

18. The process of claim 12, wherein the olefin is propylene.

* * * * *